US012685766B2

(12) United States Patent
Talaat et al.

(10) Patent No.: US 12,685,766 B2
(45) Date of Patent: Jul. 21, 2026

(54) MODIFIED GENE VACCINES AGAINST AVIAN CORONAVIRUSES AND METHODS OF USING THE SAME

(71) Applicant: WISCONSIN ALUMNI RESEARCH FOUNDATION, Madison, WI (US)

(72) Inventors: Adel Talaat, Madison, WI (US); Shaswath Chandrasekar, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 620 days.

(21) Appl. No.: 18/058,513

(22) Filed: Nov. 23, 2022

(65) Prior Publication Data

US 2023/0158138 A1     May 25, 2023

Related U.S. Application Data

(60) Provisional application No. 63/282,482, filed on Nov. 23, 2021.

(51) Int. Cl.
| | |
|---|---|
| *A61P 31/14* | (2006.01) |
| *A61K 39/12* | (2006.01) |
| *A61K 39/215* | (2006.01) |
| *A61K 39/39* | (2006.01) |
| *C07K 14/005* | (2006.01) |
| *C12N 15/86* | (2006.01) |
| *A61K 39/00* | (2006.01) |

(52) U.S. Cl.
CPC ............ *A61K 39/215* (2013.01); *A61K 39/39* (2013.01); *A61P 31/14* (2018.01); *C12N 15/86* (2013.01); *A61K 2039/552* (2013.01); *A61K 2039/55577* (2013.01); *A61K 2039/55583* (2013.01); *C12N 2770/20022* (2013.01); *C12N 2770/20034* (2013.01); *C12N 2770/20043* (2013.01)

(58) Field of Classification Search
CPC ........ A61K 39/215; C12N 15/86; A61P 31/14
See application file for complete search history.

(56) References Cited

U.S. PATENT DOCUMENTS

| | | | |
|---|---|---|---|
| 7,094,412 B2 | 8/2006 | Howley et al. | |
| 7,189,536 B2 | 3/2007 | Chaplin et al. | |
| 11,771,761 B2 * | 10/2023 | Talaat .................... | A61K 39/39 424/278.1 |
| 2006/0073594 A1 | 4/2006 | Yao et al. | |
| 2009/0169636 A1 | 7/2009 | O'Hagan et al. | |
| 2012/0027806 A1 | 2/2012 | Ilyinskii et al. | |
| 2019/0046634 A1 | 2/2019 | van Santen et al. | |
| 2020/0390883 A1 | 12/2020 | Talaat et al. | |
| 2021/0138064 A1 | 5/2021 | Uchida | |
| 2022/0160822 A1 * | 5/2022 | Talaat .................... | A61K 47/36 |
| 2024/0091349 A1 * | 3/2024 | Talaat .................... | A61K 39/39 |

FOREIGN PATENT DOCUMENTS

| | | | | |
|---|---|---|---|---|
| CN | 110812475 A | * | 2/2020 | ............. A61K 39/00 |
| WO | 2012117045 A1 | | 9/2012 | |
| WO | 2020252263 A1 | | 12/2020 | |
| WO | 2022109484 A1 | | 5/2022 | |

OTHER PUBLICATIONS

QUIL-A, TradeMark Search, downloaded on Jul. 2, 2025. (Year: 2025).*
Phillips et al., Changes in nonstructural protein 3 are associated with attenuation in avian coronavirus infectious bronchitis virus. Virus Genes 44, 63-74 (2012) (Year: 2012).*
Ramakrishnan et al., Avian Infectious Bronchitis Virus. Recent Advances in Animal Virology. Jun. 6, 2019:301-19. (Year: 2019).*
Chandraseka, et al., A Novel Mucosal Adjuvant System for Immunization against Avian Coronavirus Causing Infectious Bronchitis. J Virol 94:19, pp. 1-14. (Year: 2020).*
Hoven et al., Surface-charged chitosan: Preparation and protein adsorption, Carbohydrate Polymers, vol. 68, Issue 1, 2007, pp. 44-53. (Year: 2007).*
GenBank, spike [infectious bronchitis vurs], accession GQ504723, obtained online at: https://www.ncbi.nlm.nih.gov/protein/ADP06492, downloaded on Jun. 30, 2025 (Year: 2012).*
GenBank, nucleocapsid [infectious bronchitis virus], accession GQ504724, obtained online at: https://www.ncbi.nlm.nih.gov/protein/ADP06497, downloaded on Jun. 30, 2025. (Year: 2012).*
Coleman et al. Purified coronavirus spike protein nanoparticles induce coronavirus neutralizing antibodies in mice, Vaccine, vol. 32, Issue 26, 2014, pp. 3169-3174. (Year: 2014).*
Eldemery et al., Protection against infectious bronchitis virus by spike ectodomain subunit vaccine. Vaccine. Oct. 13, 2017;35(43): 5864-5871. (Year: 2017).*
Kallel et al., Large-scale adenovirus and poxvirus-vectored vaccine manufacturing to enable clinical trials. Biotechnology Journal, 10: 741-747, (Year: 2015).*
Bande, Faruku, et al. "Progress and challenges toward the development of vaccines against avian infectious bronchitis." Journal of immunology research 2015.1 (2015): 424860.
Yilmaz, Huseyin, et al. "Production of recombinant n protein of infectious bronchitis virus using the baculovirus expression system and its assessment as a diagnostic antigen." Applied biochemistry and biotechnology 187.2 (2019): 506-517.
Extended European Search Report in European Application No. EP22899543.7.

(Continued)

*Primary Examiner* — Abigail Vanhorn
(74) *Attorney, Agent, or Firm* — Quarles & Brady LLP

(57) ABSTRACT

The present invention provides both QuilA-loaded chitosan (QAC)-encapsulated NA vaccine compositions and viral vaccine compositions that encode an Infectious Bronchitis Virus (IBV) spike (S) protein, an IBV nucleocapsid (N) protein, or both the S protein and the N protein. Additionally, the present invention provides methods in which the disclosed vaccines are administered to a subject to induce an immune response against IBV or to vaccinate the subject against IBV.

20 Claims, 8 Drawing Sheets

Specification includes a Sequence Listing.

(56)          References Cited

OTHER PUBLICATIONS

Hsueh, L. M. Huang, P. J. Chen, C. L. Kao, P. C. Yang, Chronological evolution of IgM, IgA, IgG and neutralisation antibodies after infection with SARS-associated coronavirus. Clin Microbiol Infect 10, 1062-1066 (2004).

Huang, J. Saravia, D. You, A. J. Shaw, S. A. Cormier, Impaired gamma delta T cellderived IL-17A and inflammasome activation during early respiratory syncytial virus infection in infants. Immunol Cell Biol 93, 126-135 (2015).

Ignjatovi-Ç, J. & Sapats, S. 2000. Avian infectious bronchitis virus. Revue scientifique et technique (International Office of Epizootics), 19, 493-508.

International Search Report and Written Opinion for corresponding PCT Application No. PCT/US2020/037438, mailed Nov. 4, 2020.

International Search Report and Written Opinion for corresponding PCT Application No. PCT/US2021/060600, mailed Apr. 18, 2022.

International Search Report and Written Opinion for corresponding PCT Application No. PCT/US2022/080415, mailed Feb. 28, 2023.

Jackwood, M. W., Hilt, D. A., Mccall, A. W., Polizzi, C. N., Mckinley, E. T. & Williams, S. M. 2009. Infectious bronchitis virus field vaccination coverage and persistence of Arkansas-type viruses in commercial broilers. Avian Dis, 53, 175-83.

Jordan, B. 2017. Vaccination against infectious bronchitis virus: A continuous challenge. Vet. Microbiol.

Kamlangdee, A., Kingstad-Bakke, B. & Osorio, J. E. 2016. Mosaic H5 Hemagglutinin Provides Broad Humoral and Cellular Immune Responses against Influenza Viruses. Journal of Virology, 90, 6771-6783.

Kamlangdee, A., Kingstad-Bakke, B., Anderson, T. K., Goldberg, T. L. & Osorio, J. E. 2014. Broad Protection against Avian Influenza Virus by Using a Modified Vaccinia Ankara Virus Expressing a Mosaic Hemagglutinin Gene. Journal of Virology, 88, 13300-13309.

Kapczynski, D. R. et al. Vaccine protection of chickens against antigenically diverse H5 highly pathogenic avian influenza isolates with a live HVT vector vaccine expressing the influenza hemagglutinin gene derived from a clade 2.2 avian influenza virus. Vaccine 33, 1197-1205, doi:10.1016/j.vaccine.2014.12.028 (2015).

Kapczynski, D. R., Hilt, D. A., Shapiro, D., Sellers, H. S. & Jackwood, M. W. 2003. Protection of chickens from infectious bronchitis by in ovo and intramuscular vaccination with a DNA vaccine expressing the S1 glycoprotein. Avian Dis, 47, 272-85.

Kardani, K., Bolhassani, A. & Shahbazi, S. 2016. Prime-boost vaccine strategy against viral infections: Mechanisms and benefits. Vaccine, 34, 413-423.

Kingstad-Bakke et al., Effective mosaic-based nanovaccines against avian influenza in poultry. Vaccine 37, 5051-5058 (2019).

Langenmayer, M. C., Lulf-Averhoff, A. T., Adam-Neumair, S., Sutter, G. & Volz, A. 2018. Tracking Modified Vaccinia Virus Ankara in the Chicken Embryo: In Vivo Tropism and Pathogenesis of Egg Infections. Viruses, 10.

Lee, C. W. & Jackwood, M. W. 2001. Origin and evolution of Georgia 98 (GA98), a new serotype of avian infectious bronchitis virus. Virus Research, 80, 33-39.

Liu, M. A. 2003. DNA vaccines: a review. J Intern Med, 253, 402-10. 19.

Liu, R., Americo, J. L., Cotter, C. A., Earl, P. L., Erez, N., Peng, C. & Moss, B. 2021. 472 One or two injections of MVA-vectored vaccine shields hACE2 transgenic mice from SARSCoV-2 upper and lower respiratory tract infection. Proc Natl Acad Sci U S A, 118.

InvivoGen, "Quil-A® Adjuvant", Version 24J30-NJ. (Year: 2024).

Lu, S. 2009. Heterologous prime-boost vaccination. Curr Opin Immunol, 21, 346-51.

Luo et al., Evaluation of Antibody-Dependent Enhancement of SARS-CoV Infection in Rhesus Macaques Immunized with an Inactivated SARS-CoV Vaccine. Virol Sin 33, 201-204 (2018).

Ma, X. T. Yao, Q. Peng, D. K. Chen, The protective and pathogenic roles of IL-17 in viral infections: friend or foe? Open Biol 9, 190109 (2019).

Maeto, C., et al., Novel mucosal DNA-MVA HIV vaccination in which DNA-IL-12 plus cholera toxin B subunit (CTB) cooperates to enhance cellular systemic and mucosal genital tract immunity. PLoS One, 2014. 9(9): p. e107524.

Manrique, M. et al. Nasal DNA-MVA SIV vaccination provides more significant protection from progression to AIDS than a similar intramuscular vaccination. Mucosal Immunol 2, 536-550, doi:10.1038/mi.2009.103 (2009).

McKay et al., Self-amplifying RN 5 A SARS-CoV-2 lipid nanoparticle vaccine candidate induces high neutralizing antibody titers in mice. Nat Commun 11, 3523 (2020).

Mckinley, E. T., Hilt, D. A. & Jackwood, M. W. 2008. Avian coronavirus infectious bronchitis attenuated live vaccines undergo selection of subpopulations and mutations following vaccination. Vaccine, 26, 1274-84.

Mubarak, W. Alturaiki, M. G. Hemida, Middle East Respiratory Syndrome Coronavirus (MERS-CoV): Infection, Immunological Response, and Vaccine Development. J Immunol Res 2019, 6491738 (2019).

Reed and Muench, 1938. "A Simple Method of Estimating Fifty Per Cent Endpoints", the American Journal of Hygiene, vol. 27, No. 3. National Center for Biotechnology Information. "PubChem Compound Summary for CI D 56841866, Qui I A" PubChem, https://pubchem.ncbi.nlm.nih.gov/compound/Quil-A. Accessed Nov. 22, 2024. (Year: 2012).

Novelli, J. L. Casanova, The role of IL-12, IL-23 and IFN-gamma in immunity to viruses. Cytokine Growth Factor Rev 15, 367-377 (2004).

Orr-Burks, N., et al., Immunoglobulin A as an early humoral responder after mucosal avian coronavirus vaccination. Avian Dis, 2014. 58(2): p. 279-86.

Oyewumi, M. O., Kumar, A. & Cui, Z. 2010. Nano-microparticles as immune adjuvants: correlating particle sizes and the resultant immune responses. Expert Rev Vaccines, 9, 1095-107.

Park, S. H., Yang, S. H., Lee, C. G., Youn, J. W., Chang, J. & Sung, Y. C. 2003. Efficient induction of T helper 1 CD4+ T-cell responses to hepatitis C virus core and E2 by a DNA prime-adenovirus boost. Vaccine, 21, 4555-64.

Paules, H. D. Marston, A. S. Fauci, Coronavirus Infections—More Than Just the Common Cold. JAMA, (2020).

Peng et al., Long-lived memory T lymphocyte responses against SARS coronavirus nucleocapsid protein in SARS-recovered patients. Virology 351, 466-475 (2006).

Peng, S., et al., Optimization of heterologous DNA-prime, protein boost regimens and site of vaccination to enhance therapeutic immunity against human papillomavirus-associated disease. Cell Biosci, 2016. 6: p. 16.

Premkumar, Lakshmanane, et al. "The Receptor Binding Domain of the Viral Spike Protein Is an Immunodominant and Highly Specific Target of Antibodies in SARS-CoV-2 Patients." Science Immunology, vol. 5, No. 48, Jun. 11, 2020.

Prévost et al., Cross-sectional evaluation of humoral responses against SARS-CoV-2 Spike. bioRxiv, 2020.2006.2008.140244 (2020).

Rajput, Z. I., Hu, S. H., Xiao, C. W. & Arijo, A. G. 2007. Adjuvant effects of saponins on animal immune responses. J Zhejiang Univ Sci B, 8, 153-61.

Riteau, A. Sher, Chitosan: An Adjuvant with an Unanticipated STING. Immunity 44, 522-524 (2016).

Routhu et al., 2021. A modified vaccinia Ankara vector-based vaccine protects macaques from SARS-CoV-2 infection, immune pathology, and dysfunction in the lungs. Immunity, 54, 542-556 e9.

Saade, F. & Petrovsky, N. Technologies for enhanced efficacy of DNA vaccines. Expert Rev Vaccines 11, 189-209, doi:10.1586/erv.11.188 (2012).

Schmidt, T., et al., Immunogenicity and reactogenicity of heterologous ChAdOx1 nCoV-19/mRNA vaccination. Nat Med, 2021.

Seow et al., Longitudinal evaluation and decline of antibody responses in SARS-CoV-2 infection. medRxiv, 2020.2007.2009.20148429 (2020).

(56)                References Cited

OTHER PUBLICATIONS

Shirvani, E. & Samal, S. K. 2020. Comparative Protective Efficacies of Novel Avian Paramyxovirus—Vectored Vaccines against Virulent Infectious Bronchitis Virus in Chickens. Viruses, 12.

Shirvani, E., et al., A Recombinant Newcastle Disease Virus (NDV) Expressing S Protein of Infectious Bronchitis Virus (IBV) Protects Chickens against IBV and NDV. Sci Rep, 2018. 8(1): p. 11951.

Siracusano, C. Pastori, L. Lopalco, Humoral Immune Responses in COVID-19 Patients: A Window on the State of the Art. Front Immunol 11, 1049 (2020).

Smith et al., Immunogenicity of a DNA vaccine candidate for COVID-19. Nature Communications 11, (2020).

Sogias, I. A., Williams, A. C. & Khutoryanskiy, V. V. 2008. Why is chitosan mucoadhesive? Biomacromolecules, 9, 1837-42.

Stading et al., Infectivity of attenuated poxvirus vaccine vectors and immunogenicity of a raccoonpox vectored rabies vaccine in the Brazilian Free-tailed bat (*Tadarida brasiliensis*). Vaccine 34, 5352-5358 (2016).

Sterlin et al., IgA dominates the early neutralizing antibody response to SARS-CoV-2. medRxiv, 2020.2006.2010.20126532 (2020).

Talaat, R. Lyons, S. A. Johnston, A combination vaccine confers full protection against co-infections with influenza, herpes simplex and respiratory syncytial viruses. Vaccine. 20, 538-544 (2001).

Tan, B., et al., Coadministration of chicken GM-CSF with a DNA vaccine expressing infectious bronchitis virus (IBV) S1 glycoprotein enhances the specific immune response and protects against IBV infection. Arch Virol, 2009. 154(7): p. 1117-24.

Tan, L., et al., Infectious bronchitis virus poly-epitope-based vaccine protects chickens from acute infection. Vaccine, 2016. 34(44): p. 5209-5216.

Tang et al., Lack of Peripheral Memory B Cell Responses in Recovered Patients with Severe Acute Respiratory Syndrome: A Six-Year Follow-Up Study. Journal of Immunology 186, 7264-7268 (2011).

Tang, M., et al., Enhancement of the immunogenicity of an infectious bronchitis virus DNA vaccine by a bicistronic plasmid encoding nucleocapsid protein and interleukin-2. J Virol Methods, 2008. 149(1): p. 42-8.

Tian, L., et al., The immunoreactivity of a chimeric multi-epitope DNA vaccine against IBV in chickens. Biochem Biophys Res Commun, 2008. 377(1): p. 221-5.

Tseng et al., Immunization with SARS coronavirus vaccines leads to pulmonary immunopathology on challenge with the SARS virus. PLoS One 7, e35421 (2012).

Valosky, H. Hishiki, T. E. Zaoutis, S. E. Coffin, Induction of mucosal B-cell memory by intranasal immunization of mice with respiratory syncytial virus. Clin Diagn Lab Immunol 12, 171-179 (2005).

Van Doremalen et al., ChAdOx1 nCoV-19 vaccination prevents SARS-CoV-2 pneumonia in rhesus macaques. bioRxiv, 2020.2005. 2013.093195 (2020).

Veits, J. et al. Protective efficacy of several vaccines against highly pathogenic H5N1 avian influenza virus under experimental conditions. Vaccine 26, 1688-1696, doi:10.1016/j.vaccine.2008.01.016 (2008).

Wan, Y., et al., Receptor recognition by novel coronavirus from Wuhan: An analysis based on decade-long structural studies of SARS. J Virol, 2020.

Wang et al., A critical role of IL-17 in modulating the B-cell response during H5N1 influenza virus infection. Cell Mol Immunol 8, 462-468 (2011).

Wang et al., IL-17A Promotes Pulmonary B-1a Cell Differentiation via Induction of Blimp-1 Expression during Influenza Virus Infection. PLoS Pathog 12, e1005367 (2016).

Wang, J. Shang, S. Jiang, L. Du, Subunit Vaccines Against Emerging Pathogenic Human Coronaviruses. Front Microbiol 11, 298 (2020).

Wolfel et al., Virological assessment of hospitalized patients with COVID-2019. Nature 581, 465-469 (2020).

Yan, F., et al., Protection of chickens against infectious bronchitis virus with a multivalent DNA vaccine and boosting with an inactivated vaccine. J Vet Sci, 2013. 14(1): p. 53-60.

Yang, T., et al., Multivalent DNA vaccine enhanced protection efficacy against infectious bronchitis virus in chickens. J Vet Med Sci, 2009. 71(12): p. 1585-90.

Yu et al., DNA vaccine protection against SARS-CoV-2 in rhesus macaques. Science 369, 806-811 (2020).

Zanetti, F. A., Del Medico Zajac, M. P., Taboga, O. A. & Calamante, G. 2012. Evaluation of modified vaccinia virus Ankara expressing VP2 protein of infectious bursal disease virus as an immunogen in chickens. J Vet Sci, 13, 199-201.

Zhang, G., et al., Animal coronaviruses and SARS-CoV-2. Transbound Emerg Dis, 2020.

Zhang, P., et al., Astragalus polysaccharides enhance the immune response to avian infectious bronchitis virus vaccination in chickens. Microb Pathog, 2017. 111: p. 81-85.

Zhang, S. Jiang, L. Du, Current advancements and potential strategies in the development of MERS-CoV vaccines. Expert Rev Vaccines 13, 761-774 (2014).

Zhao, P., et al., Immune responses against SARS-coronavirus nucleocapsid protein induced by DNA vaccine. Virology, 2005. 331(1): p. 128-35.

Zhou et al., Clinical course and risk factors for mortality of adult inpatients with COVID-19 in Wuhan, China: a retrospective cohort study. The Lancet 395, 1054-1062 (2020).

Abozeid, H. H. et al. Development of a recombinant Newcastle disease virus-vectored vaccine for infectious bronchitis virus variant strains circulating in Egypt. Vet Res 50, 12, doi:10.1186/s13567-019-0631-5 (2019).

Acharya et al., Interleukin-17A Promotes CD8+ T Cell Cytotoxicity To Facilitate West Nile Virus Clearance. J Virol 91, (2017).

Agriculture, U. S. D. O. 2021. Poultry—Production and Value 2020 Summary [Online]. Available: .nass.usda.gov/Publications/Todays_Reports/reports/plva0421.pdf [Accessed].

AgriLabs, First DNA vaccine licensed for chickens. New Vaccine Technology Offers Tremendous Promise in Animal Health, Nov. 13, 2017.

Alharbi, N. K. et al. ChAdOx1 and MVA based vaccine candidates against MERS-CoV elicit neutralising antibodies and cellular immune responses in mice. Vaccine 35, 3780-3788, doi:10.1016/j.vaccine. 2017.05.032 (2017).

Altenburg et al., Modified Vaccinia Virus Ankara (MVA) as Production Platform for Vaccines against Influenza and Other Viral Respiratory Diseases. Viruses-Basel 6, 2735-2761 (2014).

Anipindi et al., Estradiol Enhances CD4+ T-Cell Anti-Viral Immunity by Priming Vaginal DCs to Induce Th17 Responses via an IL-1-Dependent Pathway. PLoS Pathog 12, e1005589 (2016).

Arsad et al. Histopathologic Changes in Liver and Kidney Tissues from Male Sprague Dawley Rats Treated with Rhaphidophora Decursiva (Roxb.) Schott Extract. J Cytol Histol. 2014.

Bagri et al., Novel Role for Interleukin-17 in Enhancing Type 1 Helper T Cell Immunity in the Female Genital Tract following Mucosal Herpes Simplex Virus 2 Vaccination. J Virol 91, (2017).

Barhate et al. "Quillaja saponaria extract as mucosal adjuvant with chitosan functionalized gold nanoparticles for mucosal vaccine delivery: Stability and immunoefficiency studies" International Journal of Pharmaceutics, Jan. 30, 2013, No. 441, No. 1-2, pp. 636-642; abstract, p. 637, col. 2, para 1, p. 638, col. 2, para 4,.

Barros-Martins, J., et al., Immune responses against SARS-CoV-2 variants after heterologous and homologous ChAdOx1 nCoV-19/BNT162b2 vaccination. Nat Med, 2021.

Borges, G. Borchard, J. C. Verhoef, A. de Sousa, H. E. Junginger, Preparation of coated nanoparticles for a new mucosal vaccine delivery system. Int J Pharm 299, 155-166 (2005).

Boyd, A. C. et al. Towards a universal vaccine for avian influenza: protective efficacy of modified Vaccinia virus Ankara and Adenovirus vaccines expressing conserved influenza antigens in chickens challenged with low pathogenic avian influenza virus. Vaccine 31, 670-675, doi:10.1016/j.vaccine.2012.11.047 (2013).

Britton, P., Armesto, M., Cavanagh, D. & Keep, S. 2012. Modification of the avian coronavirus infectious bronchitis virus for vaccine development. Bioengineered Bugs, 3, 114-119.

(56)         References Cited

OTHER PUBLICATIONS

Brock A.Kingstad-Bakke, S. S. C., Yashdeepphanse, Kathleen A.Ross, Masatohatta, M. Suresh, Yoshihiro Kawaoka, Jorge E.Osorio, Balaji Narasimhan, Adel M.Talaat 2019. Effective mosaic-based nanovaccines against avian influenza in poultry. Vaccine.

Bros, D. H. A. M. 2018. DNA Vaccines—How Far From Clinical Use? Int J Mol Sci., 19.

Cai et al., Combinatorial Nano-Bio Interfaces. ACS Nano 12, 5078-5084 (2018).

Chandrasekar et al. A DNA Prime and MVA Boost Strategy Provides a Robust Immunity against Infectious Bronchitis Virus in Chickens, Vaccines. Jan. 30, 2023. vol. 11, No. 302. pp. 1-16.

Chandrasekar, S. S., Phanse, Y., Hildebrand, R. E., Hanafy, M., Wu, C. W., Hansen, C. H., Osorio, J. E., Suresh, M. & Talaat, A. M. 2021. Localized and Systemic Immune Responses against SARS397 CoV-2 Following Mucosal Immunization. Vaccines (Basel), 9.

Chandrasekar, S.S.P., Y.; Riel, M.; Hildebrand, R.E.; Hanafy, M.; Osorio, J.E.; Abdelgayed, S.S.; Talaat, A.M. , Systemic Neutralizing Antibodies and Local Immune Responses Are Critical for the Control of SARS-CoV-2. . Viruses, 2022.

Chandrashekar et al., SARS-CoV-2 infection protects against rechallenge in rhesus macaques. Science 369, 812-817 (2020).

Chao, O. Rotzschke, E. K. Tan, The role of IgA in COVID-19. Brain Behav Immun 87, 182-183 (2020).

Chhabra, R., Forrester, A., Lemiere, S., Awad, F., Chantrey, J. & Ganapathy, K. 2015. Mucosal, Cellular, and Humoral Immune Responses Induced by Different Live Infectious Bronchitis Virus Vaccination Regimes and Protection Conferred against Infectious Bronchitis Virus Q1 Strain. Clin Vaccine Immunol, 22, 1050-9.

Cook, J. K., Jackwood, M. & Jones, R. C. 2012. The long view: 40 years of infectious bronchitis research. Avian Pathol, 41, 239-50.

Corbett et al., Evaluation of the mRNA-1273 Vaccine against SARS-CoV-2 in Nonhuman Primates. N Engl J Med, (2020).

Corthesy, Multi-faceted functions of secretory IgA at mucosal surfaces. Frontiers in Immunology 4, (2013).

Crawford et al., Protocol and Reagents for Pseudotyping Lentiviral Particles with SARS-CoV-2 Spike Protein for Neutralization Assays. Viruses 12, (2020).

De Wit et al., SARS and MERS: recent insights into emerging coronaviruses. Nature Reviews Microbiology 14, (2016).

De Wit, J. J., Cook, J. K. A. & Van Der Heijden, H. M. J. F. 2010. Infectious bronchitis virus in Asia, Africa, Australia and Latin America—history, current situation and control measures. Brazilian Journal of Poultry Science, 12, 97-106.

Didierlaurent, A. M. et al., 2009. AS04, an aluminum salt- and TLR4 agonist-based adjuvant system, induces a transient localized innate immune response leading to enhanced adaptive immunity. J Immunol, 183, 6186-97.

Ducatez, M. F., Becker, J., Freudenstein, A., Delverdier, M., Delpont, M., Sutter, G., Guerin, J. L. & Volz, A. 2016. Low pathogenic avian influenza (H9N2) in chicken: Evaluation of an ancestral H9-MVA vaccine. Vet Microbiol, 189, 59-67.

Evans, J. T., Cluff, C. W., Johnson, D. A., Lacy, M. J., Persing, D. H. & Baldridge, J. R. 2003. Enhancement of antigen-specific immunity via the TLR4 ligands MPL adjuvant and Ribi.529. Expert Rev Vaccines, 2, 219-29.

Express Pharma et al., US FDA authorises phase 1 trial of ImmunityBio's COVID-19 vaccine candidate hAd5, expresspharma.in, Oct. 15, 2020, pp. 123-234 [online].

Falchieri, M., Lupini, C., Cecchinato, M., Catelli, E., Kontolaimou, M. & Naylor, C. J. 2013. Avian metapneumoviruses expressing Infectious Bronchitis virus genes are stable and induce protection. Vaccine, 31, 2565-71.

Fisher, B. S., Dambrauskas, N., Trakhimets, O., Andrade, D. V., Smedley, J., Sodora, D. L. & Sather, D. N. 2020. Oral Immunization with HIV-1 Envelope SOSIP trimers elicits systemic immune responses and cross-reactive anti-V1V2 antibodies in non-human primates. PLoS One, 15, e0233577. 18.

Fraga, A. P., Balestrin, E., Ikuta, N., Fonseca, A. S. K., Spilki, F. R., 425 Canal, C. Í. W. & Lunge, V. R. 2013. Emergence of a New Genotype of Avian Infectious Bronchitis Virus in Brazil. Avian Diseases, 57, 225-232.

Ganapathy, K., Cargill, P. W. & Jones, R. C. 2005. A comparison of methods of inducing lachrymation and tear collection in chickens for detection of virus-specific immuoglobulins after infection with infectious bronchitis virus. Avian Pathol, 34, 248-51.

Geilhausen, H.E., F.B. Ligon, and P. D. Lukert, The pathogenesis of virulent and avirulent avian infectious bronchitis virus. Archiv für die gesamte Virusforschung, 1973. 40(3-4): p. 285-290.

GenBank accession No. MN908947, (2020).

Graham, B. S., Mascola, J. R. & Fauci, A. S. 2018. Novel Vaccine Technologies: Essential Components of an Adequate Response to Emerging Viral Diseases. JAMA, 319, 1431-1432.

Gregg, K. A., Harberts, E., Gardner, F. M., Pelletier, M. R., Cayatte, C., Yu, L., Mccarthy, M. P., Marshall, J. D. & Ernst, R. K. 2017. Rationally Designed TLR4 Ligands for Vaccine Adjuvant Discovery. mBio, 8.

Guo, Z., et al., Priming with a DNA vaccine and boosting with an inactivated vaccine enhance the immune response against infectious bronchitis virus. J Virol Methods, 2010. 167(1): p. 84-9.

Harari, A., et al., An HIV-1 clade C DNA prime, NYVAC boost vaccine regimen induces reliable, polyfunctional, and long-lasting T cell responses. J Exp Med, 2008. 205(1): p. 63-77.

Hernandez, & Brown, D. T., Growth and Maintenance of Chick Embryo Fibroblasts (CEF). (John Wiley & Sons, Inc, Current Protocols in Microbiology, May 2010).

Hobernik et al. "DNA Vaccines—How far from Clinical Use?" International Journal of Molecular Sciences, vol. 19, No. 11, Nov. 15, 2018, p. 3605.

Hopkins Sr, Y. H. J. 1986. Reversion to virulence of chicken-passaged infectious bronchitis vaccine virus. Avian Diseases.

* cited by examiner

Fig. 8

MODIFIED GENE VACCINES AGAINST AVIAN CORONAVIRUSES AND METHODS OF USING THE SAME

STATEMENT REGARDING FEDERALLY SPONSORED RESEARCH

This invention was made with government support under 2016-67021-25042 and 2020-67021-31256 awarded by the USDA/NIFA. The government has certain rights in the invention.

CROSS-REFERENCE TO RELATED APPLICATIONS

This application is being filed electronically via Patent Center and includes an electronically submitted Sequence Listing in .xml format. The .xml file contains a sequence listing entitled "960296_04361" created on Sep. 4, 2024, and is 122,441 bytes in size. The Sequence Listing contained in this .xml file is part of the specification and is hereby incorporated by reference herein in its entirety.

SEQUENCE LISTING

This application is being filed electronically via Patent Center and includes an electronically submitted Sequence Listing in .xml format. The .xml file contains a sequence listing entitled "960296_04361" created on Sep. 4, 2024, and is 122,441 bytes in size. The Sequence Listing contained in this .xml file is part of the specification and is hereby incorporated by reference herein in its entirety.

BACKGROUND

Coronavirus infections, such as infection by infectious bronchitis virus (IBV) in poultry, cause significant health problems for avian subjects as well as economic losses to the poultry industry. A major hurdle to combat these infections is the diversity of viral antigens that can be present in a given outbreak. In addition, a critical failure in preparation for coronavirus infections in avian subjects is the absence of effective vaccines that can be delivered to thousands of animals at the same time. Consequently, there is a dire need for an objective vaccination method that effectively, yet parsimoniously, encompasses existing and emerging isolates of coronavirus, e.g., IBV, to protect against coronavirus infection in avian subjects.

SUMMARY

In a first aspect of the current disclosure, vaccine compositions are provided. In some embodiments, the vaccine compositions comprise a polynucleotide that encodes an infectious bronchitis virus (IBV) spike(S) protein, an IBV nucleocapsid (N) protein, or both the S protein and the N protein. The polynucleotide may be a DNA or RNA and maybe codon optimized for expression in the subject targeted for vaccination. The compositions may further comprise an adjuvant and the adjuvant may include disaggregated spherical nanostructures comprising Quil-A® and chitosan.

In another aspect of the current disclosure, vaccine compositions comprising a viral vector are provided. In some embodiments, the viral vector comprises a polynucleotide encoding an infectious bronchitis virus (IBV) (S) protein, an IBV nucleocapsid (N) protein, or both the S protein and the N protein.

In still another aspect, a vaccine composition comprising an infectious bronchitis virus (IBV) (S) protein, an IBV nucleocapsid (N) protein, or both the S protein and the N protein. The S and N proteins may include one or more of SEQ ID NOs: 11-17, 21, 23, 25, 27, 29, 31, 33, 10, 18, 35, and 37. The vaccine compositions may further comprise an adjuvant such as the Quil-A®-chitosan adjuvant.

In another aspect of the current disclosure, methods of inducing an immune response against infectious bronchitis virus (IBV) in a subject are provided. In some embodiments, the method comprises: administering the vaccine compositions of current disclosure in an amount effective to induce the immune response against at least one IBV antigen in the subject.

In another aspect of the current disclosure, methods of inducing an immune response against infectious bronchitis virus (IBV) in a subject are provided. In some embodiments, the method comprises: administering a first vaccine composition comprising a polynucleotide that encodes an infectious bronchitis virus (IBV) spike(S) protein, an IBV nucleocapsid (N) protein, or both the S protein and the N protein and a viral vector comprising a polynucleotide encoding an infectious bronchitis virus (IBV) (S) protein, an IBV nucleocapsid (N) protein, or both the S protein and the N protein, wherein administration of the first vaccine composition and the second vaccine composition induces the immune response against at least one IBV antigen in the subject. The first and second vaccine compositions may be administered at separate times with at least two weeks separating the two administrations. In one embodiment the first vaccine composition comprising a polynucleotide is administered prior to the second vaccine composition comprising a viral vector expressing a polypeptide encoded by the polynucleotide.

BRIEF DESCRIPTION OF THE DRAWINGS

Figure 8:
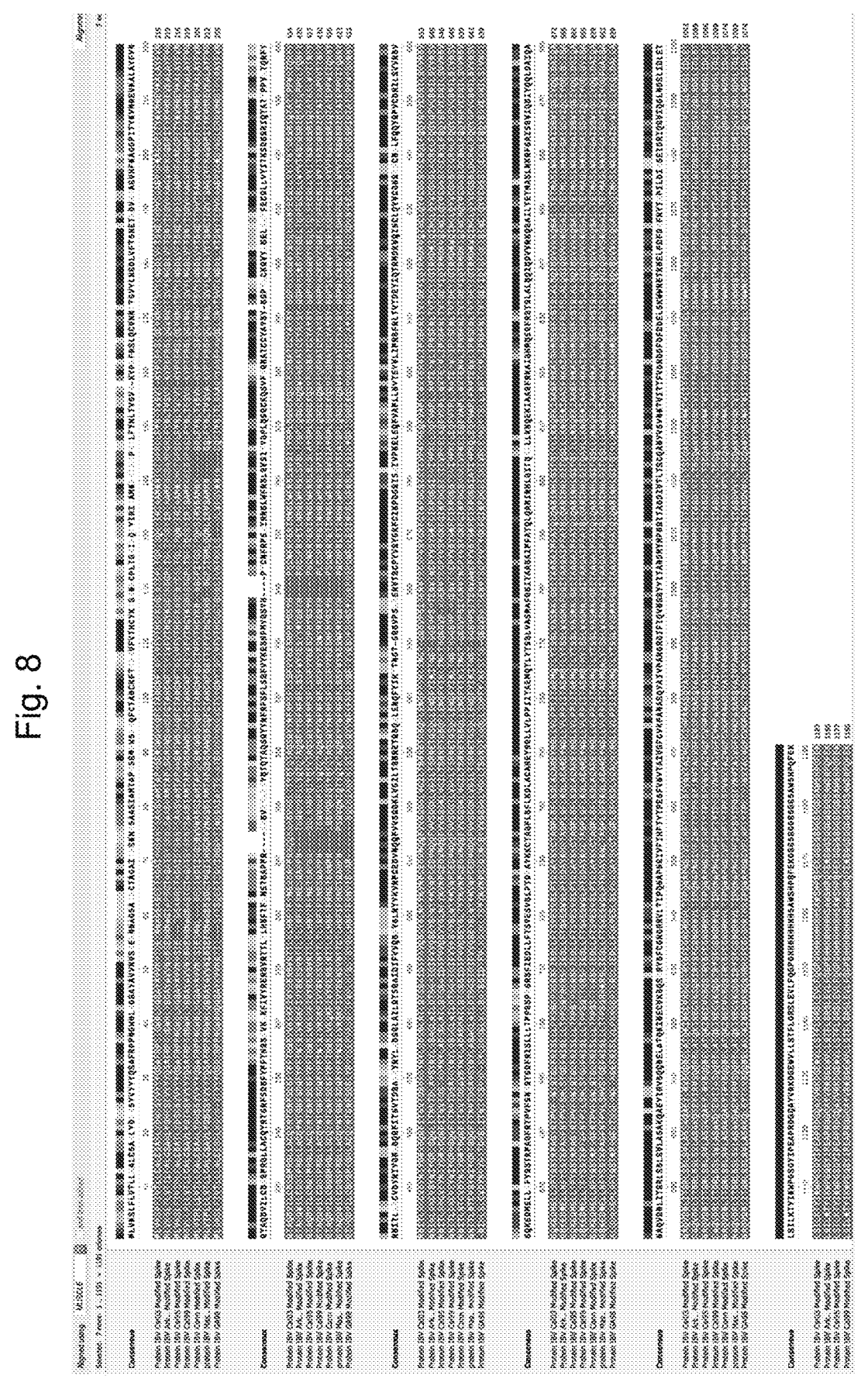

FIG. 8. Alignment of 7 IBV S protein amino acid sequences. Sequences correspond to, from top to bottom, SEQ ID NOs: 39-45.

DETAILED DESCRIPTION

Figure 1:
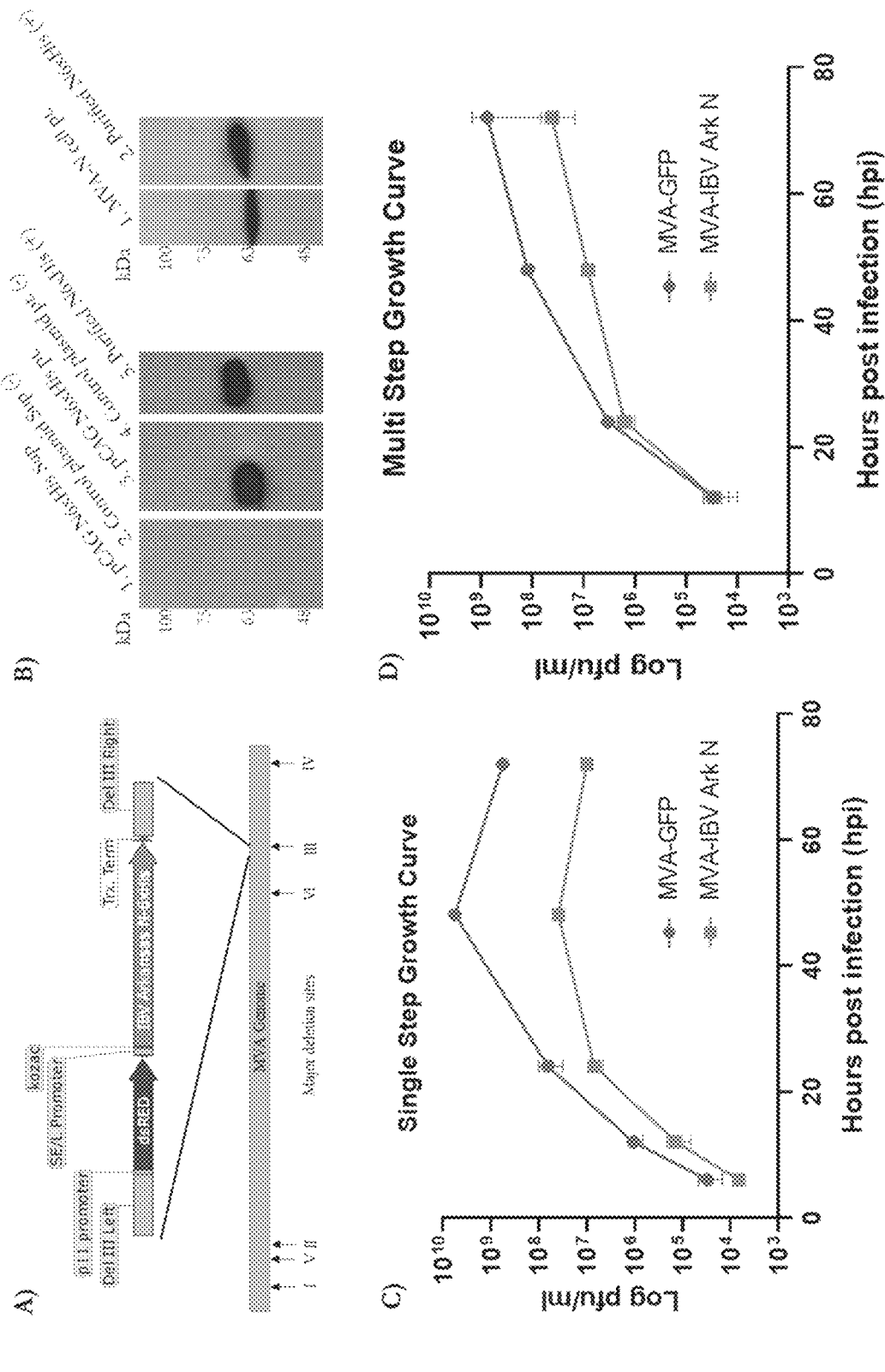
FIG. 1. Design and characterization of MVA-IBV vaccine constructs. a) MVA vaccine construct expressing N protein with the addition of C-terminal 6× His tag. Gene map was generated using Snapgene software. b) Western blot analysis with anti 6×His-HRP antibody for pCAG-N plasmid (left) and MVA-N (right) confirming expression of N protein from vaccine constructs. Lanes are as follows: Left, supernatant (lane 2) CEF cells transfected with control plasmid, supernatant (lane 1) CEF cells transfected with pCAG-N plasmid. Cell pellet (lane 4) CEF cells transfected with control plasmid, cell pellet (lane 3) CEF cells transfected with pCAG-N plasmid and control purified N6×His protein (lane 5). Right, cell pellet (lane 1) from CEF cells infected with MVA-TrN and control purified N6×His protein (lane 2). Cell pellet (lane 2) from CEF cells infected with MVA-N. c) Single step and d) Multi step growth curve of parental MVA-GFP and recombinant MVA-N vaccine vectors.

The present invention provides nucleic acid-based vaccine compositions (DNA vaccines), protein subunit based vaccines and viral vaccine compositions encoding an infectious bronchitis virus (IBV) spike(S) protein, an IBV nucleocapsid (N) protein, or both the S protein and the N protein. Further, the present invention provides methods in which the disclosed vaccines are administered to a subject to induce an immune response directed against IBV.
Compositions:

In a first aspect, the present invention provides vaccine compositions. In some embodiments, the vaccine composition comprises a polynucleotide that encodes an infectious bronchitis virus (IBV) spike(S) protein, an IBV nucleocapsid (N) protein, or both the S protein and the N protein. Alternatively, the compositions may comprise a viral vector encoding an infectious bronchitis virus (IBV) spike(S) protein, an IBV nucleocapsid (N) protein, or both the S protein and the N protein. AS another alternative, protein subunit vaccine compositions comprising an infectious bronchitis virus (IBV) spike(S) protein, an IBV nucleocapsid (N) protein, or both the S protein and the N protein are also provided. The nucleic acids encoding the proteins may be RNA or DNA and may be codon optimized for expression in the subject targeted for vaccination. The S and N proteins and nucleic acids encoding the same may be modified to allow for increased inducement of the immune response after administration.

As used herein, the terms "DNA vaccine," "nucleic acid vaccine," "NA vaccine" and "plasmid vaccine" are used interchangeably to refer to a polynucleotide encoding at least one antigen. Following immunization, a subject's cells take up the polynucleotide and express the encoded antigen from it, inducing an immune response against the antigen. NA vaccines offers several potential advantages over traditional vaccine strategies, including the stimulation of both B- and T-cell responses, improved storage stability, the absence of any infectious agent, and the relative ease of large-scale manufacture. However, NA vaccines also come with several challenges, including in vivo degradation of the construct by DNases or RNases, inefficient uptake by antigen presenting cells, and low immunogenicity. See, for example, P. Cai, X. Zhang, M. Wang, Y. L. Wu, X. Chen, Combinatorial Nano-Bio Interfaces. ACS Nano 12, 5078-5084 (2018); and D. H. a. M. Bros, DNA Vaccines—How Far From Clinical Use? Int J Mol Sci. 19, (2018), both of which are incorporated by reference herein. Nucleic acid-based vaccines generally contain additional elements in addition to the polynucleotide encoding the antigen such as a promoter functional in cells of the subject to be immunized or may be altered to offer increased stability or resistance to degradation in the host cell.

As used herein, "antigen" refers to a substance that induces a targeted immune response in a subject. For example, in some embodiments, the compositions disclosed herein comprise one or more polynucleotides that encode an infectious bronchitis virus (IBV) spike(S) protein, an IBV nucleocapsid (N) protein, or both the S protein and the N protein. Therefore, in the foregoing example, the antigens are the IBV S and N proteins that are encoded by the one or more polynucleotides. In some embodiments, the S proteins are encoded by one or more of the group consisting of SEQ ID NOs: 1-7, 22, 24, 26, 28, 30, 32, and 34. The S proteins encoded by these polynucleotides are provided as SEQ ID NOs: 11-17, 21, 23, 25, 27, 29, 31, and 33, and any polynucleotide encoding SEQ ID NO: 11-17, 21, 23, 25, 27, 29, 31, and 33, is included, as the coding sequence for the proteins may be optimized for expression in particular cell types. In some embodiments, the N proteins are encoded by one or more of SEQ ID NOs: 8, 9, 36 and 38. The N proteins encoded by these polynucleotides are provided as SEQ ID NOs: 10, 18, 35, and 37, respectively, and any polynucleotide encoding SEQ ID NO: 10, 18, 35, or 37 is also encompassed herein. The polynucleotides provided herein may be altered to optimize codon usage for maximal expression in a particular host such as a poultry. Thus, the sequences provided herein also include sequences with 70%, 75%, 80%, 85%, 90%, 92%, 94%, 95%, 96%, 97%, 98%, or 99% identity to the sequences of SEQ ID NO: 1-9, 22, 24, 26, 28, 30, 32, 34, 36, and 38. The proteins encoded by the polynucleotides may also encompass changes especially as these proteins are known to exist in various isoforms and be antigenically diverse in outbreaks of IBV. The sequences provided herein also include sequences with 70%, 75%, 80%, 85%, 90%, 92%, 94%, 95%, 96%, 97%, 98%, or 99% identity to the amino acid sequences of SEQ ID NO: 10-18, 21, 23, 25, 27, 29, 31, 33, 35 or 37. In some embodiments, the polynucleotide encodes both the S and N proteins on a single molecule. As such, in some embodiments, the polynucleotide comprises sequences linking the S and N proteins. The N and S sequences may be linked via a polynucleotide of any length but should be in frame or contain independent regulatory regions such as an internal ribosome entry site to allow for expression of both proteins from the polynucleotide.

As used herein, a "fragment" is a portion of an amino acid sequence which is identical in sequence to, but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. A fragment may include an N-terminal truncation, a C-terminal truncation, or both N-terminal and C-terminal truncations relative to the full-length reference polypeptide.

The term "recombinant" when used with reference, e.g., to a cell, or nucleic acid, protein, expression cassette, or vector, indicates that the cell, nucleic acid, protein, expression cassette, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, have higher than normal expression, are under-expressed, or not expressed at all.

The polynucleotide vaccine compositions provided herein may be DNA or RNA and may include regulatory regions to allow for transcription and/or translation of the polynucleotides into polypeptides once in a cell of a vaccinated subject. The polynucleotides may be operably linked to promoters that are capable of recruiting transcriptional machinery in target cells of the vaccinated subject, e.g., cells of the upper respiratory tract, or, in some embodiments, any somatic cell of the subject.

However, as discussed above, NA vaccines can suffer from several drawbacks including in vivo degradation of the construct by DNases or RNases, inefficient uptake by antigen presenting cells, and low immunogenicity. In some embodiments, the vaccine composition further comprises an adjuvant. In some embodiments, the adjuvant comprises disaggregated spherical nanostructures comprising Quil-AR and chitosan, which are present at a ratio between 1:15 and 1:100. As used herein, the term "adjuvant" or "vaccine adjuvant" refers to any substance that enhances the immune response to an antigen. The inventors envision that the use of articulate delivery systems, such as QuilA-loaded Chitosan (QAC) nanoparticles used with the present invention, may overcome these challenges by facilitating a prolonged release of active plasmid. See, for example, S. S. Chandrasekar, B. A. Kingstad-Bakke, C. W. Wu, M. Suresh, A. M. Talaat, A Novel Mucosal Adjuvant System for the Immunization Against Avian Coronavirus Causing Infectious Bronchitis. J Virol, (2020), which is incorporated by reference herein. An exemplary adjuvant used with the vaccine compositions disclosed herein is a Quil-AR chitosan (QAC) complex, in which Quil-AR and chitosan are combined to form distinct disaggregated spherical nanostructures. The QAC complexes are loaded with one or more payload molecules (in this case, the antigen-encoding polynucleotide) with which the QAC complex stimulates an immune response. The QAC complex adjuvant was previously described in International Application No. PCT/US2020/037438, which is incorporated by reference, and Chandrasekar et al. 2020, supra. Advantageously, QAC-adjuvanted vaccines appear to target local mucosal immunity, which results in a more effective immune response to IBV given that airway epithelium T cells and IgA humoral responses have been shown to be critical for restricting respiratory viral pathogens. See, for example, N. v. D.

Emmie de Wit, Darryl Falzarano and Vincent J. Munster, SARS and MERS: recent insights into emerging coronaviruses. Nature Reviews Microbiology 14, (2016), which is incorporated by reference herein.

"Quil-AR" refers to the powdered saponin fraction isolated from extract of the bark of *Quillaja saponaria* trees. Quil-AR is commercially available, for example from Desert King sold under the product name Vet-Sap™.

"Chitosan" refers to a linear polysaccharide composed of randomly distributed β-linked D-glucosamine and N-acetyl-D-glucosamine. Chitosan can be obtained from the chitin shells of shrimp and other crustaceans by treatment of the shells with an alkaline substance. Chitosan is a non-toxic, naturally occurring cationic polymer that readily complexes with DNA and negatively charged proteins that is biocompatible and biodegradable. Compositions incorporating chitosan have sustained release kinetics and are immunomodulatory, enhancing the T-cell response. In some embodiments, chitosan is deacetylated chitosan, for example deacetylated chitosan (>75%). Deacetylated chitosan is available commercially from Sigma (C3646). Higher deacetylation percentages, for example about 90%, will meditate stronger binding with nucleic acids resulting in slower release kinetics from the nanoparticle structures of the QAC complex. In some embodiments, the chitosan is at least 70%, 75%, 80%, 85%, 90%, or 95% deacetylated. In some embodiments, the chitosan is between about 60% and about 90% deacetylated.

In some embodiments, the chitosan is functionalized. Chitosan may be functionalized with negatively charged sulfonate groups by reaction of the amino group of chitosan with 5-formyl-2-furan sulfonic acid (FFSA) followed by treatment using sodium borohydride to form a negatively charged chitosan surface. Use of the negatively charged chitosan in the formation of the QAC complex will generally be favorable for loading of positively charged payload molecules.

The QAC complex is loaded with the antigen-encoding polynucleotide by mixing a solution of Quil-A® and polynucleotide into a solution of chitosan to form a final mixed solution containing a QAC-polynucleotide complex. In the final mixed solution, the Quil-AR and the chitosan are present at a ratio of between 1:15 to 1:100. In some embodiments, the Quil-A® and the chitosan are present at a ratio of about 1:20 (e.g., 1:15, 1:16, 1:17, 1:18, 1:19, 1:20, 1:21, 1:22, 1:23, 1:24, or 1:25) in the final mixed solution. In some embodiments, in the final solution Quil-A® is at a concentration of 0.001% and chitosan is at a concentration between about 0.02% and about 0.1%.

In some embodiments, the QAC complex nanostructures are less 100 nm in diameter when measured in the absence of any payload molecules. For example, the nanostructures may be between about 5 nm and about 100 nm, between about 10 nm and about 95 nm, between about 15 nm an about 90 nm, between about 20 nm and about 90 nm, or between about 25 nm and about 85 nm in the absence of a payload molecule. The QAC complex may be loaded with one or more payload molecules such as the polynucleotides described herein encoding an IBV spike(S) protein, an IBV nucleocapsid (N) protein, or both the S protein and the N protein. The nucleotide-QAC complex may be between about 20 nm and about 1000 nm in diameter. The specific size of the nucleotide-QAC complex will vary depending on the size and amount of payload in the nanostructure. As used herein, "disaggregated," refers to the formation of discrete observable particles as opposed to aggregated non-discrete assemblies with non-distinct boundaries and "spherical"

means roughly spherical in nature and is not meant to be a precise definition of the structure.

Though the QAC adjuvant strategy significantly improves the immunogenicity and protective immune response generated by the NA vaccine compositions of the current disclosure, the inventors hypothesized that a heterologous vaccine approach may further increase the effectiveness of the compositions. As used herein, "heterologous vaccine approach" refers to practice of inducing a first immune response with a first vaccine composition, then inducing a second immune response with a second different vaccine composition. Accordingly, a "heterologous vaccine" may also refer to the "second different vaccine composition" in the preceding example.

Therefore, in a second aspect, vaccine compositions comprising a viral vector are provided. In some embodiments, the viral vector comprises a polynucleotide encoding an infectious bronchitis virus (IBV) (S) protein, an IBV nucleocapsid (N) protein, or both the S protein and the N protein.

As used herein, a "viral vector" refers to a virus or viral particle that comprises a polynucleotide encoding at least one antigen. The viral vector delivers the polynucleotide into a subject's cells. Within the cell, the polynucleotide is transcribed and translated, producing the encoded antigen. Depending on the cell that is expressing the viral antigen, the antigen may be presented on major histocompatibility complex I or II (MHC-I or MHC-II). Thus, the adaptive immune system, e.g., T and B cells, may recognize the antigen and become activated. The viral vectors may be used to induce an immune response to the S or N protein of IBV. The viral vectors of the present invention are "recombinant viruses," in which foreign genetic material encoding an antigenic protein (i.e., from infectious bronchitis virus) has been inserted into the viral genome.

The viral vectors may be a weakened or killed version of a virus. For example, the viral vector can be based on an attenuated virus, which does not replicate or exhibits very little replication in a host but is able to introduce and express a foreign gene in infected cells. As used herein, an "attenuated virus" is a strain of a virus whose pathogenicity has been reduced compared to its natural counterpart. A virus may be attenuated using serial passaging, plaque purification, or other means. The viruses used herein may be viral like particles (VLP) that are not capable of replication in the subject but do carry the antigenic proteins.

In some embodiments, the viral vector is selected from an adeno-associated virus or a poxvirus. Suitable poxviruses for use with the present invention include, without limitation, canary poxvirus, raccoon poxvirus, vaccinia virus, fowl poxvirus, turkey herpes virus (HVT), and myxoma virus (MYXV). Poxviruses are advantageous for transferring genetic material into new hosts due to their relatively large genome size (approximately 150-200 kb) and because of their ability to replicate in the infected cell's cytoplasm rather than the nucleus, thereby minimizing the risk of integrating genetic material into the genome of the host cell. Of the poxviruses, the vaccinia and variola species are the two that are most studied. Vaccinia virus is highly immunogenic, provoking strong B-cell (humoral) and T-cell mediated (cellular) immune responses against its encoded gene products. Of these viruses, the modified vaccinia virus Ankara (MVA) is particularly safe, as it has diminished virulence while maintaining good immunogenicity. Thus, in some embodiments, the viral vector is a modified vaccinia Ankara (MVA) virus. Exemplary MVA virus strains include MVA 572, MVA 575, and MVA-BN, which have been deposited at the European Collection of Animal Cell Cultures (ECACC), Salisbury (UK) with the deposition numbers ECACC V94012707, ECACC V00120707 and ECACC V00083008, respectively, and are described in U.S. Pat. Nos. 7,094,412 and 7,189,536, incorporated herein by reference in their entireties.

In yet another embodiment, a vaccine composition including IBV spike(S) protein, an IBV nucleocapsid (N) protein, or both the S protein and the N protein is provided. These proteins may be modified from those found natively in the IBV virus such that the protein subunit vaccine composition comprising these proteins induces an immune response in a subject after administration of the vaccine composition.

Both the NA vaccine compositions and the viral vaccine compositions of the present invention comprise a polynucleotide encoding an IBV spike(S) protein, an IBV nucleocapsid (N) protein, or both the S protein and the N protein. The protein subunit vaccine compositions provided herein comprise the IBV S protein, the N protein or a combination thereof. The vaccine compositions may also include more than one of the S proteins or N proteins or nucleic acids encoding more than one S protein or more than one N protein provided herein. Such vaccine compositions would be considered as multivalent vaccine compositions and any combination of S and N protein may be combined and th combination may vary depending on the circulating IBV virus in a particular area or at a particular point in time.

IBV S protein is the major antigen against which neutralizing and protective antibodies are produced. The S protein is partially or completely cleaved into the amino-terminal S1 and into the carboxy-terminal S2 subunits post translationally by a host furin-like protease. Furthermore, the S1 subunit is highly variable among different isolates of IBV and is responsible for viral attachment to host cell and contains major neutralizing epitopes. In some embodiments, the compositions of the current disclosure comprise polynucleotides encoding the S protein selected from the group consisting of SEQ ID NOs: 1-7, 22, 24, 26, 28, 30, 32, and 34 (DNA) or SEQ ID NOs: 11-17, 21, 23, 25, 27, 29, 31, and 33 (amino acid), sequences with 90% or more identity to SEQ ID NO: 1-7, 22, 24, 26, 28, 30, 32, and 34 or SEQ ID NOs: 11-17, 21, 23, 25, 27, 29, 31, and 33 or fragments or portions thereof. The S2 subunit is highly conserved among IBV strains and contributes to viral fusion activity and elicits some minor but broadly reactive neutralizing antibodies. See, for example, Shirvani et al., "A Recombinant Newcastle Disease Virus (NDV) Expressing S Protein of Infectious Bronchitis Virus (IBV) Protects Chickens against IBV and NDV", Scientific Reports volume 8, Article number: 11951 (2018), incorporated by reference herein in its entirety.

IBV N protein is associated with the RNA genome and forms the ribonucleoprotein. In some embodiments of the disclosed compositions, the N protein is encoded by a sequence selected from the group consisting of SEQ ID NOs: 8, 9, 36, and 38 (DNA) or SEQ ID NOs: 10, 18, 35, and 37 (amino acid), sequences with 90% or more identity to SEQ ID NO: 8-9, 36, and 38, SEQ ID NO: 10, 18, 35, and 37 or fragments or portions thereof.

The compositions of the current disclosure are administered, in some embodiments, intranasally, intramuscularly, or are administered in ovo. In some embodiments, the compositions are administered to greater than one subject at a time through means known in the art, for example, through mass intranasal administration of a group of animals. In some embodiments, the compositions of the current disclosure are administered by aerosol delivery to a flock of birds, for example, chickens.

The vaccine compositions of the present invention may be used as a prophylactic, e.g., to prevent or ameliorate the effects of a future infection by IBV, or may be used as a therapeutic, e.g., to treat IBV. The vaccines provided herein are expected to induce and enhance the immune response of the subject to IBV. The immune response enhanced is suitably a polyfunctional response. As used herein, a "polyfunctional response" refers to an immune response comprising both B and T cells directed to the pathogen.

The vaccine compositions may further comprise other suitable agents or ingredients. Suitable agents may include a suitable carrier or vehicle for delivery. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories may be found in the U.S. Pharmacopeia National Formulary, 1857-1859, (1990).

The vaccine formulation may be separated into vials or other suitable containers. The vaccine formulation herein described may then be packaged in individual or multi-dose ampoules or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user and administered to a patient.

Methods:

In another aspect of the current disclosure, methods of inducing an immune response against infectious bronchitis virus (IBV) in a subject are provided. In some embodiments, the method comprises: administering a first vaccine composition and administering a second vaccine composition wherein administration of the first vaccine composition and the second vaccine composition induces the immune response against at least one IBV antigen in the subject. In some embodiments, a first vaccine compositions comprises a polynucleotide that encodes an infectious bronchitis virus (IBV) spike(S) protein, an IBV nucleocapsid (N) protein, or both the S protein and the N protein. In some embodiments, the vaccine composition further comprises an adjuvant. In some embodiments, the adjuvant comprises disaggregated spherical nanostructures comprising Quil-AR and chitosan, and wherein the Quil-AR and chitosan are present at a ratio between 1:15 and 1:100. In some embodiments, the chitosan is functionalized by treatment with 5-formyl-2-furan sulfonic acid and sodium borohydride, such that the chitosan surface is negatively charged. In some embodiments, the vaccine composition comprises spherical nanostructures between about 5 nm and about 100 nm in diameter in the absence of a payload molecule.

The vaccine composition may be a polynucleotide. In some embodiments, the S protein is encoded by one or more of the group consisting of SEQ ID NO: 1-7, 22, 24, 26, 28, 30, 32, and 34 or a sequence capable of encoding at least one of SEQ ID NO: 11-17, 21, 23, 25, 27, 29, 31, and 33. In some embodiments, the N protein is encoded by SEQ ID NO:8, 9, 36 or 38, or a sequence capable of encoding at least one of SEQ ID NO: 10, 18, 35, or 37. In some embodiments, the polynucleotide encodes both an S protein and an N protein.

In some embodiments, the vaccine composition comprises a viral vector. In some embodiments, the viral vector comprises a polynucleotide encoding an infectious bronchitis virus (IBV) (S) protein, an IBV nucleocapsid (N) protein, or both the S protein and the N protein. In some embodiments, the viral vector is selected from an adeno-associated virus or a poxvirus. In some embodiments, the viral vector is a modified vaccinia Ankara (MVA) virus or turkey herpes virus (HVT). In some embodiments, the sequence encoding the S protein comprises one or more of the group consisting of SEQ ID NO:1-7, 22, 24, 26, 28, 30, 32, and 34 or a sequence encoding SEQ ID NO: 11-17, 21, 23, 25, 27, 29, 31. In some embodiments, the sequence encoding the N protein comprises SEQ ID NO:8, 9, 36 or 38 or a sequence encoding SEQ ID NO: 10, 18, 35, or 37. In some embodiments, the viral vector encodes both the S protein and the N protein.

In other embodiments, the vaccine composition comprises a protein subunit vaccine composition. The protein subunits in the vaccine composition may include one or more of a IBV S protein or an IBV N protein or portion thereof. The vaccine compositions may further comprise an adjuvant and the adjuvant may be a Quil-A® chitosan adjuvant. In one embodiment the the vaccine composition may include both an S protein and an N protein or combinations of more than one S protein and more than on N protein. The S protein may be selected from SEQ ID NO: 11-17, 21, 23, 25, 27, 29, 31 or combinations thereof. The N protein may be selected from SEQ ID NO: 10, 18, 35, or 37 or combinations thereof.

The methods of the current disclosure comprise administration of vaccine composition that elicits an immune response against IBV. The timing of the administration of the vaccine compositions may be varied. Accordingly, in some embodiments, administration of the second vaccine composition occurs at least three weeks after administration of the first vaccine composition. In some embodiments, administration of the second vaccine composition occurs at least six weeks after administration of the first vaccine composition. A hallmark of the QAC adjuvant system is slow release of payload with continual priming of the immune system. Thus, the inventors hypothesize that release of DNA payload can be sustained up to six weeks after which another immunization will further boost immune responses.

The inventors disclose herein that heterologous vaccine strategies for eliciting an immune response against IBV are highly successful. Therefore, in some embodiments, the first vaccine composition comprises a NA vaccine composition, and the second vaccine composition comprises a viral vector or protein subunit vaccine composition.

The methods of the current disclosure comprise administering two vaccine compositions. In some embodiments, both the administration events comprise administering the vaccine compositions via the same route. In other embodiments, the first and second vaccine compositions are administered via different routes. For example, in some embodiments, the vaccine compositions are administered intranasally, intramuscularly, or administered in ovo. Thus, in some embodiments, the first vaccine composition is administered in ovo and the second vaccine composition is administered intranasally. In some embodiments, the first vaccine composition is administered in ovo and the second vaccine composition is administered in ovo. In some embodiments, the first vaccine composition is administered in ovo and the second vaccine composition is administered intramuscularly. In some embodiments, the first vaccine composition is administered intranasally and the second vaccine composition is administered intranasally. In some embodiments, the first vaccine composition is administered intranasally and the second vaccine composition is administered intramuscularly. In some embodiments, the first vaccine composition is administered intramuscularly and the second vaccine composition is administered intramuscularly. In some embodiments, the first vaccine composition is administered intramuscularly and the second vaccine composition is administered intranasally.

As used herein, "subject" refers to avian and non-avian animals. An "avian subject" may be any member of the class Aves including, but not limited to, chickens, turkeys, ducks, or other fowl. The term "poultry" refers generally to any avian subject that is agriculturally relevant, e.g., chickens, ducks, ostriches, guinea fowl, turkeys, quail, pheasants, Muscovy ducks, and the like. The term "subject" does not denote a particular age or sex. In one embodiment, the subject is a chicken. In a preferred embodiment, the chicken is at risk of being infected IBV.

The phrase "amount effective to induce the immune response," as used herein, refers to an amount of a vaccine composition that would induce a humoral immune response against at least one IBV antigen (e.g., the spike or nucleocapsid protein encoded by the disclosed vaccines) and suitably also induces a polyfunctional T cell response as well. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with the virus. The protective immunity conferred by a vaccine may also be evaluated by measuring, e.g., clinical signs such as mortality, morbidity, temperature, overall physical condition, overall health, and the performance of the subject. The amount of a vaccine that is therapeutically effective may vary depending on the particular strain of virus used, the antigen used in the vaccine, the species of the subject, the condition of the subject (e.g., age, body weight, gender, health), and should be determined by a veterinarian or physician. The therapeutically effective amount may be administered in one or more doses and is preferably in the range of about 0.01-10 mL, most preferably 0.05-1 mL, containing 1-200 micrograms, most preferably 1-100 micrograms of vaccine formulation/dose.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

While some claims provided herein are directed to methods of treating a subject, both human and non-human subjects are envisioned. In addition, use of the compositions provided herein as medicaments for uses in therapy or for treating disease are also provided herein. Use of the compositions provided herein in the manufacture of a medicament for the treatment of a disease or condition are also encompassed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1—Heterologous and Homologous DNA Confer Protection Against Avian Coronavirus Infectious bronchitis (IB) is an acute respiratory disease of chicken caused by the avian coronavirus, Infectious Bronchitis Virus (IBV). Modified Live Virus (MLV) vaccines commercially used can revert to virulence in the field, recombine with circulating serotypes and can cause tissue damage in vaccinated birds. Previously, we showed that a mucosal adjuvant system, QuilA-loaded Chitosan (QAC) nanoparticles encapsulating plasmid vaccine encoding for IBV Nucleocapsid (N) is protective against IBV. Here, we report a heterologous strategy using QAC encapsulated plasmid vaccine followed by a Modified Vaccinia Ankara (MVA) expressing the same IBV N antigen. Heterologous vaccination led to the development of robust T-cell responses. Heterologous vaccine immunized birds had reduced clinical severity and >2-fold reduction viral burden in lachrymal fluid and tracheal swabs post-challenge in contrast to homologous MVA vaccination where no protection was observed. Outcomes of this study indicate that the heterologous vaccine strategy is more immunogenic and protective than homologous vaccination.

Coronaviruses (CoVs) are enveloped, large viruses with a positive-sense, single-strand, RNA genome ranging from 27-31 Kb in length. They are broadly classified into four genera: Alphacoronavirus, Betacoronavirus, Gammacoronavirus, and Deltacoronavirus [1]. CoVs can infect a wide range of hosts, including humans, poultry, mice, pigs, cats, camels, bats, etc. CoVs infections usually cause acute diseases, primarily in the respiratory and gastrointestinal tract [1]. Human CoVs like OC43, 229E, HKU1, and NL63 cause mild respiratory disease. Other CoVs like SARS-COV-2, SARS, MERS in humans, and Avian CoV like Infectious Bronchitis Virus (IBV) in chickens can cause more acute severe respiratory disease [1-3]. IBV is classified within the genus gammacoronavirus encoding for major structural proteins, spike glycoprotein (S), envelope (E), membrane (M), and nucleocapsid (N) [4] and is the etiological agent of infectious bronchitis in chickens. In a typical infectious bronchitis infection, chickens develop respiratory signs, including sneezing, tracheal rales, nasal discharge, and labored breathing[5]. Mortality associated with infectious bronchitis is low; however, concomitant secondary bacterial infections can increase mortality[3]. Infectious bronchitis has a significant economic impact on the commercial US poultry industry, valued at over $35 billion in the US [6]. Infectious bronchitis infections in broilers can lead to reduced weight gain, and low feed conversion and infections in layers can lead to a drop in egg production and quality[7]. Typically, losses of around $450,000 per week can be expected due to IB outbreaks in facilities producing about 1 million broilers per week, which is unsustainable in the poultry industry characterized by low-profit margins[8]. IBV control currently revolves around extensive vaccination and acceptable flock management practices like optimal stocking densities, house temperature, water and air quality, etc., to prevent increased mortality due to secondary bacterial infections. Modified live virus (MLV) and inactivated vaccines are the leading vaccine types used against IB. Although effective, MLVs have an inferior safety profile. MLVs have a propensity to persist, revert to virulence in the field, and readily recombine with other circulating serotypes, leading to novel serotypes' emergence due to single mutations as a consequence of lack of polymerase proof-reading activity [9-11]. The emergence of GA98 serotype has been linked to the extensive use of DE072 vaccine [12]. Moreover, current vaccines do not cross-protect against multiple circulating serotypes because of variations in the S protein [13-15]. Unfortunately, safer inactivated vaccines are poorly immunogenic underscoring the need to develop an effective and safe vaccine for IBV control [8].

Experimental plasmid DNA vaccines have been developed against multiple poultry pathogens, and most recently, conditional approval for a DNA vaccine against H5 avian flu was given [16]. Varying protection levels are observed with experimental plasmid DNA vaccines expressing IBV S1, N, and M genes delivered via the intramuscular, intranasal and in ovo routes[17-25]. DNA vaccines offer several advantages over traditional vaccine approaches; they are safe, thermostable, comparatively inexpensive, and can be rapidly developed in the face of a novel serotype field outbreak [26]. A significant problem with DNA vaccines is their low immunogenicity owing to in vivo degradation leading to reduced cellular uptake and bioavailability. Vaccine hostile surfaces like the nasal mucosa can degrade DNA vaccine before target immune cell uptake[27, 28]. Nanoparticle adjuvant systems like QAC can protect against DNA degradation and boost immune responses observed with DNA vaccines as described by our group previously for the intranasal delivery of DNA immunogens[29, 30].

Similarly, viral vector vaccines against IBV based on Newcastle disease virus, Herpesvirus of turkeys and avian metapneumovirus backbones have been developed with great promise [31, 32]. However, none of them have been licensed for use owing to limited efficacy and regulatory concerns. The heterologous vaccine has been evaluated against viral pathogens like HIV-1, HPV, HCV, and Influenza [33-36]. Although the concept of heterologous vaccine for the poultry industry refers to a broadly cross-protective vaccine, for the purpose of this paper the heterologous vaccination refers to the concept of using a different vaccine platform for boosting from the vaccine that was used for priming. Particularly in this study, we evaluated DNA priming followed by viral vector boosting in comparison to viral vector homologous priming and boosting. The efficacy of heterologous vaccine strategies has been shown with different routes and viral vectors for boosting like vaccinia (e.g, Modified Vaccinia Ankara-MVA), adeno, and VSV (Vesicular Stomatitis Virus) [35]. Heterologous vaccination compared to homologous immunization can lead to a 4 to 10 fold increase in T-cell responses[35]. Previously, we have shown that a heterologous vaccination involving QAC encapsulated plasmid DNA priming followed by MVA boosting was shown to be immunogenic and protective against SARS-COV-2 challenge in transgenic mice[37, 38]. Although the heterologous vaccine approach has been characterized and extensively evaluated for human viral pathogens, not much work has been done in the context of viral poultry pathogens.

We have previously shown that a two-dose QAC encapsulated plasmid DNA (pQAC-N) encoding the N protein was protective against IBV challenge to levels seen with MLV vaccination[30]. We hypothesized that a heterologous vaccine strategy with pQAC-N prime followed by an MVA viral vector boost expressing the N protein (MVA-N) would also protect immunized chicks against IBV challenge similar to our findings with human coronavirus, SARS-CoV-2 [37, 38]. The prime/boost of the experimental vaccines were delivered via the intranasal route and hereafter referred to as either heterologous vaccine or pQAC/MVA-N. Our results indicate that pQAC/MVA-N vaccine elicits a robust IBV specific CD8+ and TCRγδ+ T-cells which protect vaccinated birds against IBV challenge. Levels of protection in vaccinated birds were higher when compared to homologous 2×MVA-N vaccine. Our data demonstrate that intranasal immunization with pQAC/MVA-N protected vaccinated birds with a significant reduction in clinical signs and viral load in trachea and lachrymal fluid to levels on par with commercial MLV vaccinated birds. Also, addition of another adjuvant MPLA (Synthetic Monophosphoryl Lipid A), did not significantly improve protection observed with pQAC/MVA-N.

Materials and Methods

Ethics Statement

All the animals used in this study were cared for in accordance with established guidelines, and the experimental protocols were approved by the Institutional Animal Care and Use Committee (IACUC) of the University of Wisconsin at Madison.
Cells and Viruses Chicken Embryonic Fibroblasts (CEF) were prepared from 9-day-old specific pathogen free (SPF) white leghorn eggs (Charles River Laboratories, Inc., WA, USA) as described previously[39] and used for confirming expression of IBV Ark NoxHis protein from vaccine constructs. The cells were cultured in DMEM (Dulbecco's Modified Eagle Medium) at 37° C., 5% CO2 atmosphere in plastic flasks with ventilated caps. The virulent IBV Arkansas DPI strain (a kind gift from Dr. Ladman and Dr. Gelb) was propagated in 9-day old SPF ECEs and allantoic fluid harvested four days after infection. The stock virus titer was determined using RT-qPCR (see below) and also titrated and expressed as 50% embryo infectious dose (EID$_{50}$)[40]. IBV S1 gene sequence of Ark DPI challenge isolate is AF006624.
Preparation of IBV Vaccine Constructs pCAG-N encoding IBV Arkansas N protein was constructed and loaded into QAC nanoparticles as described previously[30]. To confirm insertion of genes in the correct orientation, DNA sequencing was performed at the UW-Madison Biotechnology Center with an ABI Prism 3730XL DNA analyzer using BigDye terminators (Applied Biosystems, CA). To confirm expression of N protein, CEF cells seeded in 6-well format was transfected with an optimized ratio of DNA (4 ug): TransIT PRO transfection reagent (2 ul) according to manufacturer's instructions (Mirus Bio, WI, USA). Three days post transfection, cells and supernatant (separately) were harvested for western blot analysis. The MVA expressing N was generated as described before in CEF cells[41]. The cell and supernatant fractions were boiled in Laemmli sample buffer (BioRad, Hercules, CA, USA) and resolved on a 4-20% SDS-PAGE gel by electrophoresis using a Mini-PROTEAN 3 system (BIO-RAD, CA). Polyacrylamide gels were electroblotted onto nitrocellulose membranes using a Turboblot® system. Membranes were blocked in 5% (W/V) skim milk and probed with polyclonal anti-6×His HRP antibody (ThermoFisher Scientific, MA1-21315-HRP). Membranes were developed using a solid phase 3, 30, 5, 50-tetramethylbenzidine (TMB) substrate system.
Vaccine Efficacy Study.

The protective efficacy of pQAC/MVA-N construct was evaluated in 1-day-old white leghorn SPF chicks (Charles River Laboratories). A total of 40 chicks was divided equally into 4 groups (N=10 each) and used for the efficacy study, first 2 groups were inoculated with PBS (negative control) or commercial Arkansas MLV (Mildvac-Ark®, Merck Animal Health USA, positive control) via direct intranasal instillations (dose according to manufacturer's instructions). The other groups were either vaccinated with MVA-N (10$^8$ pfu/bird) at day −1 and followed by a booster dose at day −14 via intranasal (IN) route or pQAC-N (100 ug/bird) at day −1 and followed by a booster MVA-N (10$^8$ pfu/bird) dose at day −14 via intranasal (IN) route. Birds were challenged with a dose of 6.5E9 genome copy no or 10$^{6.5}$ EID$_{50}$/bird of virulent IBV Arkansas DPI strain via direct intranasal instillations at day −21 of age. The challenge dose was determined in an independent infection experiment wherein the challenge dose resulted in discernable clinical signs as early as 3 dpc and peak viral load replication was observed at 6 dpc. At 10, 20 dpv & 3 days post challenge (DPC) serum and lachrymal fluid samples were harvested for ELISA and at 6 DPC for viral load estimation (see below). Lachrymation was induced by placing sodium chloride (salt) crystals on the eyes and lachrymal fluid were collected using micropipettes [42]. Clinical severity was noted every day post challenge for 8 days, as described before [31]. The severity scores of clinical signs of IBV were as follows; 0=normal, 1=Infrequent sneezing (single event during observation), 2=frequent sneezing (more than one event during observation), 1=mild rales, 2=severe rales, 2=presence of nasal exudate. The severity scores of IBV clinical signs, described in the figure legends were recorded once a day for each chicken for 8 days after challenge. Lachrymal fluid and tracheal swabs harvested at 6 dpc was analyzed for viral RNA using IBV N gene specific qRT-PCR. A similar experimental design was used to test the efficacy of the pmQAC/MVA-N vaccine candidate in a follow-up trial. 10 ug MPLA/bird (PHAD®, Avanti® Polar Lipids) was added to QAC-pCAG-N formulation before IN inoculation and followed by a booster MVA-N (10$^8$ pfu/bird) dose at day −14 via intranasal (IN) route. Birds were challenged with a dose of 6.5E9 genome copy no or 10$^{6.5}$ EID$_{50}$/bird of virulent IBV Arkansas DPI strain via direct intranasal instillations at day −21 of age. Vaccine efficacy read outs including viral shedding and clinical severity scoring as detailed for the previous primary trial were evaluated.
IBV Specific ELISA Sera and lachrymal fluid from different time-points were screened for humoral response against IBV Arkansas serotype. In order to measure IgY and IgA antibody levels in plasma and lachrymal fluid of chicken respectively, an IBV-specific enzyme-linked immunosorbent assay (ELISA) was developed as described previously with modifications [43]. Briefly, ELISA plates were coated with inactivated IBV Arkansas (100 ng/well, IgY) or IBV Arkansas S1 and N6×His protein (50 ng total/well, IgA) diluted in carbonate/bicarbonate buffer, pH 9.6 and incubated overnight at 4 C followed by blocking with 5% Skim milk to reduce background. A 50 ul of diluted serum (1/200) or lachrymal fluid (1/50) harvested at different time-points from immunized chickens was added to the wells and incubated at 37 C for 1 hour. Post washing (PBS-TritonX 100, 0.1%), either HRP conjugated anti-chicken IgY (NBP1-74778, NOVUS Bio) or anti-chicken IgA (NB7284, NOVUS Bio) at dilutions of 1/1000 was added to the wells and incubated at 37° C. for 1 hr. Post washing, 50 ul of TMB substrate solution was added and incubated for 20 minutes or until color developed. The reaction was stopped by the addition of IM sulphuric acid and plates are read at 450 nm. To generate standard curves, sera and lachrymal fluid from severely IBV infected chickens from previous experiments was used. Two-fold serial dilutions was assigned and arbitrary value and used for analysis.
Flow Cytometric Assessment of IBV Specific Proliferation In a separate follow-up study, 16 chicks were divided equally into 4 groups (N=10 each) and used for the flow cytometric assessment, first 2 groups were inoculated with PBS (negative control) or commercial Arkansas MLV (Mildvac-Ark®, Merck Animal Health USA, positive control) via direct intranasal instillations (dose according to manufacturer's instructions). The other groups were either vaccinated with MVA-N (10$^8$ pfu/bird) at day −1 and followed by a booster dose at day −14 via intranasal (IN) route or pQAC-N (100 ug/bird) at day −1 and followed by a booster MVA-N (10$^8$ pfu/bird) dose at day −14 via intranasal (IN) route. All chicks were euthanized at 20 dpv and single cell suspensions from lungs were prepared using standard techniques and used for T-cell proliferation assay. Briefly, lungs were excised and placed in a gentleMACS dissociator M tube (Miltenyi 130-093-236) with 5 mL collagenase B (2 mg/ml, Roche). Lung tissue was processed using the gentleMACS dissociator followed by incubation for 30 min at 37° C. with gentle shaking. Single-cell suspensions lung were prepared by gently squeezing through a 70-mm cell strainer (Falcon) after lysing RBCs using 1×BD Biosciences BD Pharm Lyse™. Total of $10^7$ cells/ml were stained with CellTrace™ Violet Cell Proliferation dye (Thermo Scientific C34557) according to manufacturer's instructions and 100 ul of cells plated/well in RPMI 1640 with 10% chicken immune serum. After overnight incubation at 41° C., 5% $CO_2$. cells were stimulated with 130 ng of IBV Arkansas N6×His protein complexed with chitosan per well in 100 ul of RPMI 1640 with 10% chicken immune serum. Four days post stimulation, cells were stained for surface markers, CD4-AF647 (clone CT-4), CD8α-FITC (clone 3-298) together and TCRγ8-FITC (clone TCR-1) independently for flow cytometry analysis. All antibodies were purchased from SouthernBiotech (Birmingham, AL, USA). All samples were acquired on an BD LSR Fortessa flow cytometer. Data were analyzed with FlowJo software (BD Biosciences). The strategy for gating on proliferating CD4+ and CD8a+ T cells was debris exclusion on the Forward Scatter (FSC)-Side Scatter (SSC) dot plot followed by exclusion of dead cells by fixable viability dye eFluor 780 (Invitrogen™, #65-0865-14) staining. Out of the live cells, total proliferated cells were gated positive using a histogram plot with ef450 on the x-axis (for CellTrace™ Violet). Finally, CD4 cells were gated positive at the AF647 axis and CD8a cells were gated positive at the FITC axis in a FITC-AF647 dot plot. A similar approach was used for identifying proliferating TCRγδ+ T-cells. The output, stimulation index (SI) is the ratio of % proliferating cells post stimulation to the % proliferating cells in unstimulated condition. The chicks from different groups used here were part of another bigger study and the data for only the control groups (PBS and MLV) have already been published[30].

Viral Load Measurement

RNA was extracted from lachrymal fluid (10 μl) or Tracheal swabs (100 μl) collected from chickens using Zymo Direct-Zol™ RNA mini prep kit (Zymo Research, CA, USA) according to manufacturer's instructions. RT-qPCR was conducted in two steps: cDNA synthesis (Invitrogen™ SuperScript™ III First-Strand Synthesis System) and qPCR reactions. cDNA synthesis was performed with 0.5 μl (50 ng/μl) random hexamers, 0.5 μl of 10 mM dNTPs, and 4 μl RNA and heated at 65° C. for 5 min and chilled on ice followed by addition of 1 μl of 10× RT buffer, 1 μl of 0.1 M DTT, 1 μl of 25 mM MgCl2, 0.5 μl of RNaseOUT and 0.5 μl of SuperScript III enzyme in final volume of 10 μl. The reaction conditions include 25° C. for 5 min, 50° C. for 60 min and 70° C. for 15 min. SYBR green RT-qPCR was performed using an IBV N gene specific primer pair set forward primer: 5' ATGCTCAACCTAGTCCCTAGCA 3' (SEQ ID NO: 46) and reverse primer: 5' TCAAACTGCG-GATCATCACGT 3' (SEQ ID NO: 47) amplifying 128 nt of N gene of IBV Arkansas DPI. PCRs were performed using a StepOnePlus™ Real-Time PCR System (Applied Biosystems, Foster City, CA, U.S.A) under the following conditions: one cycle 95 C for 2 min followed by 40 cycles of 95 C for 3 sec and 60 C for 30 sec. Each 20 μl reaction was carried out using 1 μl of diluted cDNA (1/10), 10 μl of GoTaq® qPCR mastermix (Promega), 2 μl of forward and reverse primers and 7 μl of nuclease free water. A serial 10-fold dilution of pCAG-IBV Ark N6×His plasmid was used to establish the standard curve. Temperature melt curve analysis was used to confirm the specificity of the product.

The challenge dose as estimated with the above-described method was 6.5E9 genome copy no which roughly translated to $10^{6.5}$ $EID_{50}$.

Statistical Analysis

Statistical analyses were performed using GraphPad software (La Jolla, CA). Cellular immune assays, clinical severity scoring, viral loads were compared using an ordinary one-way ANOVA test with multiple comparisons where *, $P<0.05$; , $P<0.01$; *, $P<0.001$; ****, $P<0.0001$ were considered significantly different among groups. Antibody titers were compared using a two-way ANOVA test where *, $P<0.05$; , $P<0.01$; *, $P<0.001$; ****, $P<0.0001$ were considered significantly different among groups.

Results:

Design and Construction of MVA-IBV Constructs

The expression of recombinant N from the plasmid DNA vaccine (pCAG-N) was confirmed using western blot analysis on cells and supernatant harvested from transfected chicken embryonic fibroblast (CEF) cells (FIG. 1B). The SE/L promoter controls the expression of the recombinant N-6×His protein in the MVA vaccine candidate (MVA-N, FIG. 1A). As observed with pCAG-N construct, expression of N-6×His antigen was also confirmed using western blot analysis with anti-6×His antibody staining in the cell pellets from MVA-N infected CEF cells (FIG. 1B). To characterize and understand if the expression of IBV N-6×His protein affects MVA replication in cell culture, we evaluated the growth kinetics of MVA-N and parental MVA-GFP in permissive CEF cells. CEF cells were either infected at a MOI of 1 (single step) or 0.1 (multi-step) and viral titers subsequently determined on CEF cells (FIGS. 1C and 1D). MVA-N replicated at rates similar to parental MVA-GFP, although the final titers of the recombinant MVA were about 100-fold lower than that of the parental virus (FIGS. 1C and 1D).

Heterologous Vaccine Strategy Elicits Robust Localized T-Cell Responses

Figure 2:
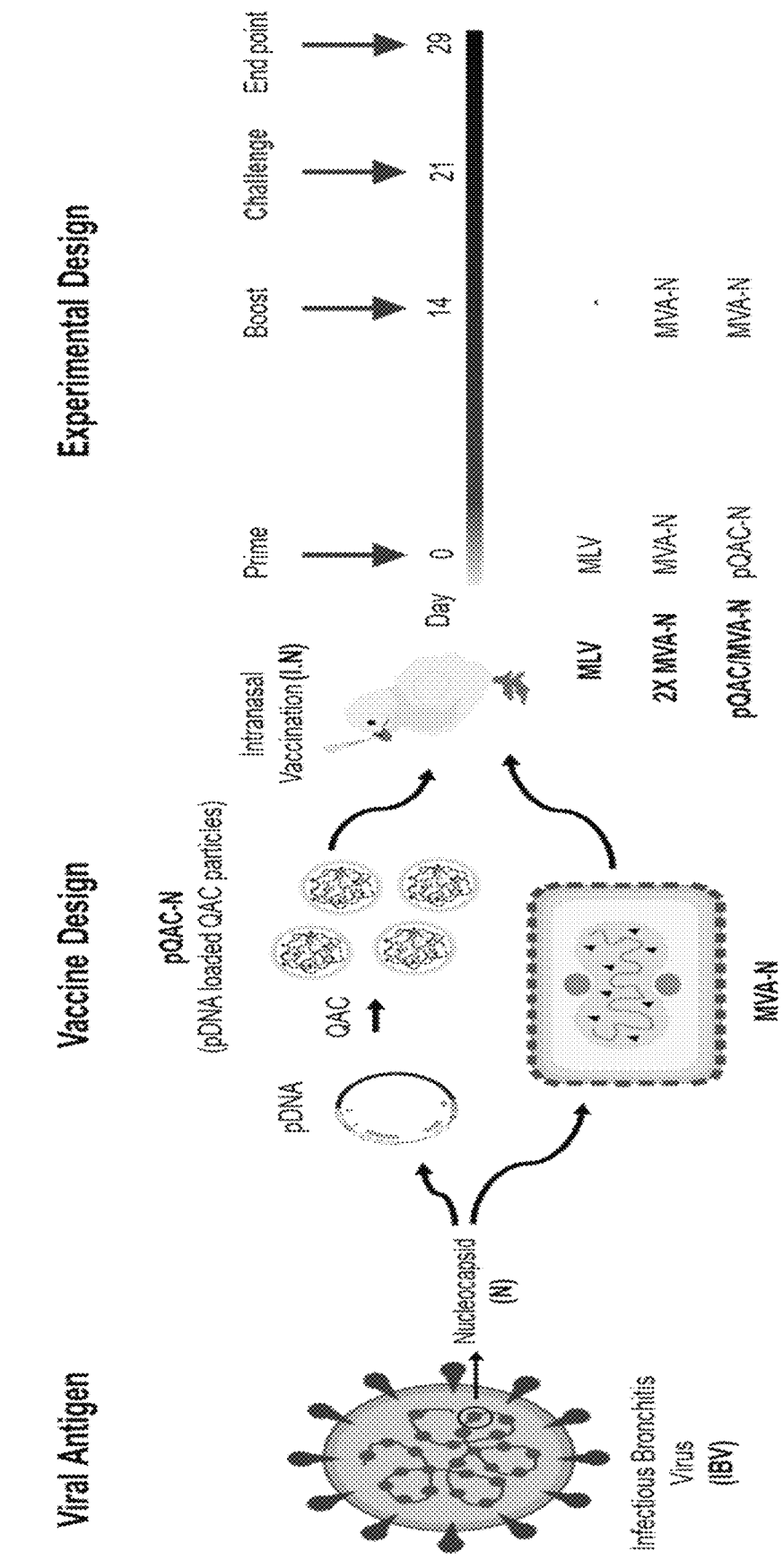
FIG. 2. Vaccine experimental design. Experimental design of IBV immunization and challenge studies. Outline for vaccine construct and immunization protocol using groups of white leghorn SPF birds vaccinated with 2 doses of MVA-N (IN) or pQAC-CoV (I.N) at day −0 followed by boost with MVA-CoV (IN) day −14. Control groups include unvaccinated PBS group and commercial MLV vaccination at day −0 (IN).
Figure 3:
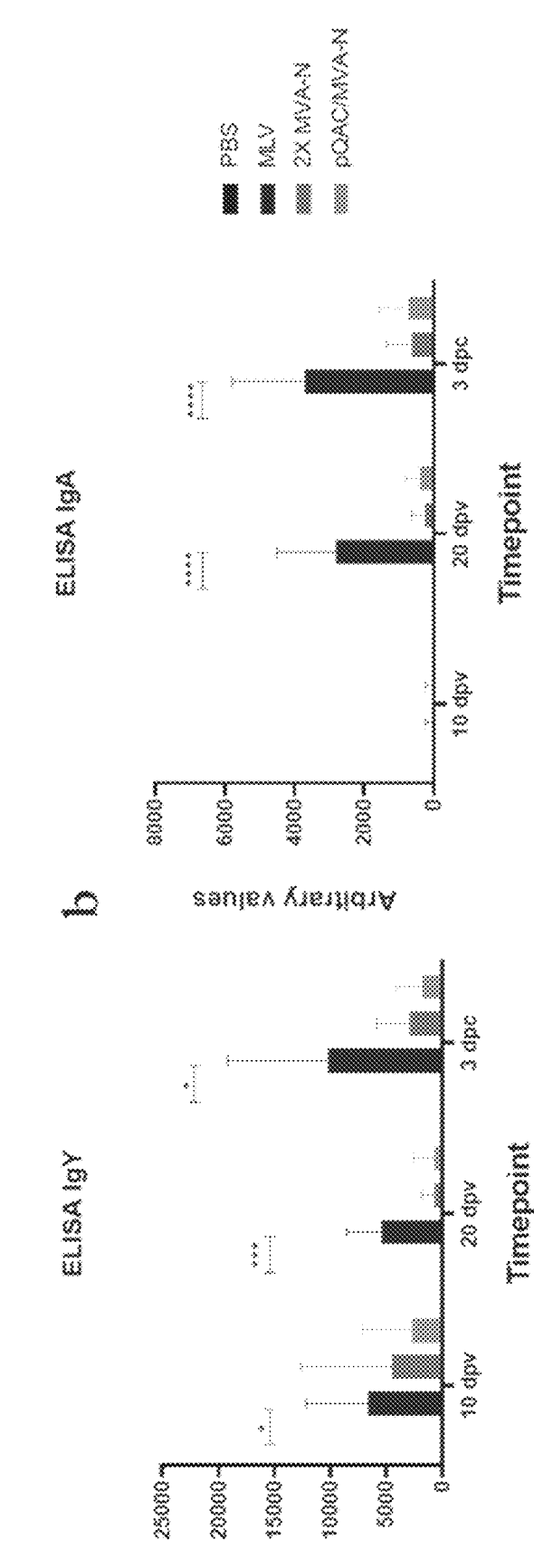
FIG. 3. Humoral responses in vaccinated SPF chicks. IBV specific a) IgY in serum and b) IgA in lachrymal fluid, significance (*, P<0.05; *, P<0.001; **, P<0.0001) was determined by two-way ANOVA. Data show means±SEM.

We have previously reported the safety, and protective efficacy of QAC complexed pCAG-N DNA vaccine (pQAC-N) in chickens against IBV Arkansas challenge although no humoral responses were observed [30]. We hypothesized that a heterologous mucosal strategy of priming with pQAC-N followed by boosting with MVA-N would offer a similar or better level of protection than observed with 2-dose intranasal (IN) pQAC-N vaccination with complementing humoral responses. We examined the ability of our experimental vaccines to elicit local and systemic IBV-specific immune responses following IN immunization (FIG. 2). Lachrymal fluid samples and serum harvested at different time points, 10, 20 days post-vaccination (dpv, pre-challenge) and three days post-challenge (dpc) were examined for IBV specific IgA (lachrymal fluid, local) and IgY (serum, systemic) using ELISA. IBV specific IgA and IgY were significantly higher in the MLV groups when compared to the unvaccinated PBS group (FIGS. 3A and 3B). Although detectable at multiple time points, both IgA and IgY levels were not significantly high in birds vaccinated with either the homologous or heterologous vaccine strategy (FIGS. 3A and 3B).

We next evaluated the ability of the experimental vaccines to elicit local (lung) IBV N specific cellular immune responses. Antigen-specific T-cell proliferation assay based on CellTrace™ Violet Cell dye staining of lung cells to trace proliferating T cells was used as described previously[30]. The stimulation index (SI), which is the fold increase in stimulated to unstimulated cells was calculated. Total lung cells from pQAC/MVA-N vaccinated birds had significantly higher proliferation in response to N antigen stimulation which was higher than the control and 2×MVA-N groups (FIG. 4A). An increase in the stimulation of proliferating TCRγδ+ and CD8+ T-cells was observed in pQAC/MVA-N vaccinated birds in comparison to control birds (FIGS. 4C & 4D) while CD4+ T-cell proliferation was higher in MLV vaccinated birds (FIG. 4B), albeit non-significant. These results highlight the ability of the heterologous pQAC/MVA-N vaccine strategy to elicit robust IBV-specific immune responses.

Heterologous Vaccine is More Effective than the Homologous Vaccine Strategy.

Figure 4:
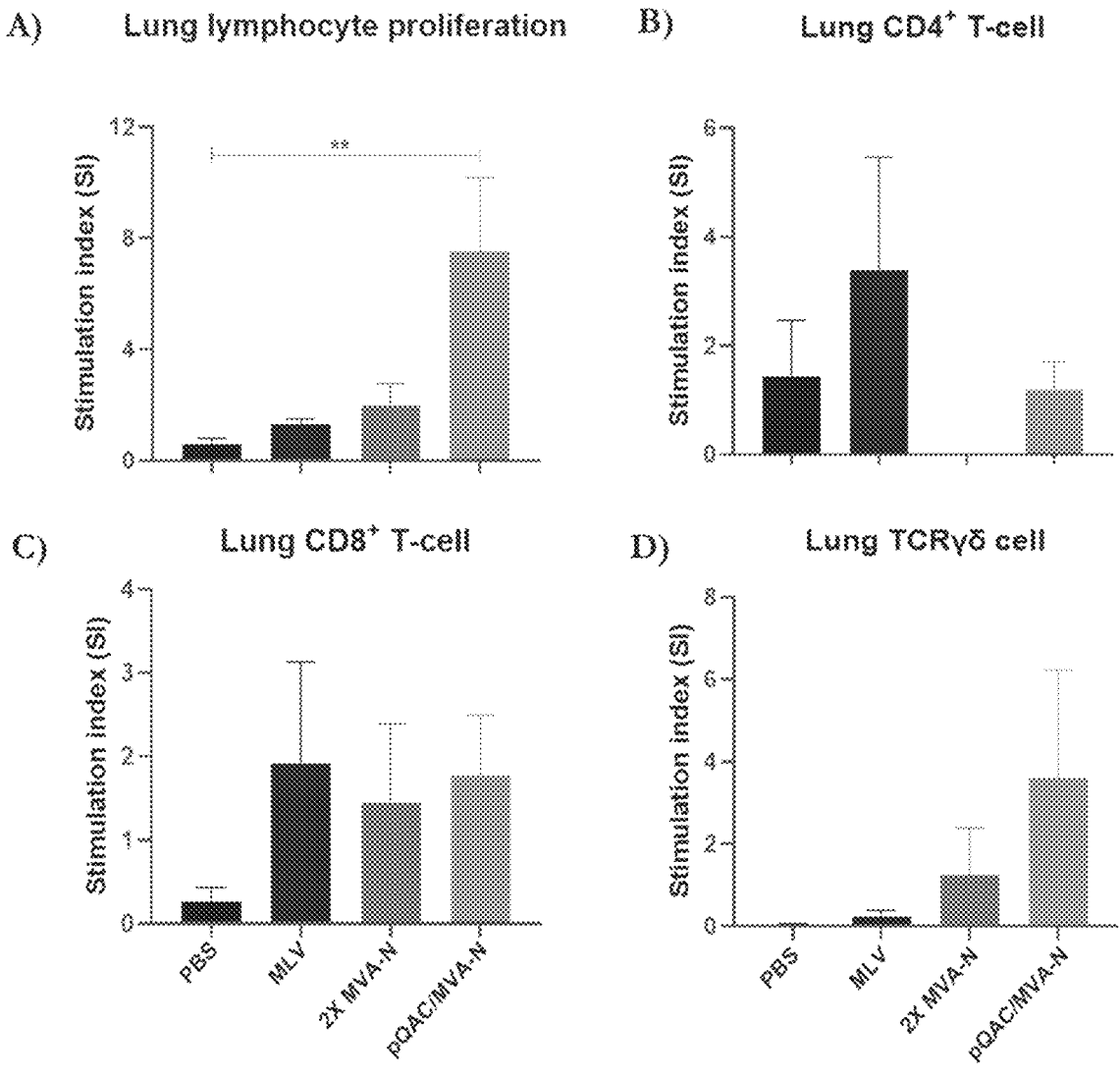
FIG. 4. Localized T-cell immune responses in vaccinated chicks. Lung cell proliferative capacity measured by Cell-Trace Violet dye dilution in unvaccinated, MLV, 2×MVA-N and pQAC/MVA-N vaccinated chickens. Proliferation was measured in a) total lung cells, (b) CD4+, (c) CD8+ and (d) TCRγδ+ lung T cells after 4 days in culture post antigen stimulation. Non-significance, ns or significance (*, P<0.05; **, P<0.01) was determined by one-way ANOVA with multiple comparisons. Data show means±SEM.
Figure 5:
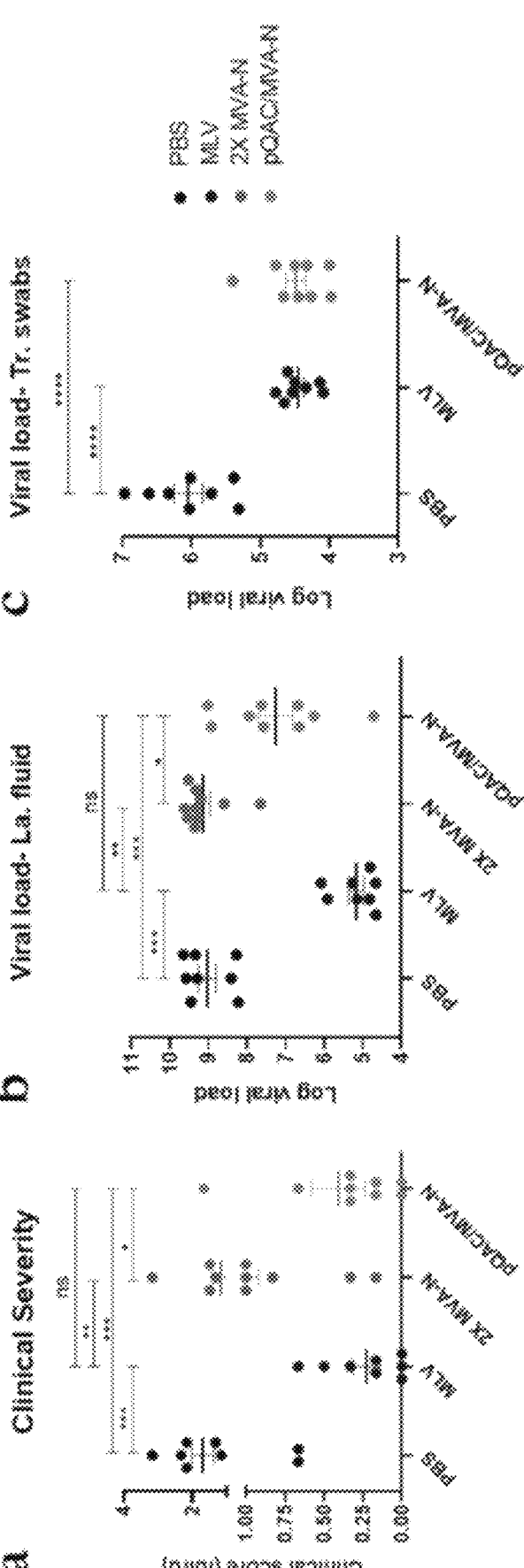
FIG. 5. Increased protection with heterologous vaccine strategy against IBV. a) Clinical sign severity represented as average score/bird over 8 days post challenge in each group. b) IBV log viral load/10 ul lachrymal fluid at 6 days post challenge. c) IBV log viral load in tracheal swab at 6 days post challenge. Non-significance, ns or significance (*, P<0.001; **, P<0.0001) was determined by one-way ANOVA with multiple comparisons. Data show means±SEM.

Twenty-one days post initial vaccination (21 dpv) and seven days post final boost, immunized birds were challenged with a virulent strain of IBV Arkansas DPI Serotype via the intranasal route to evaluate vaccine efficacy. Immunization with homologous 2×MVA-N did not confer any protection against the challenge; no reduction in clinical severity was observed (FIG. 5A). In contrast, immunization with heterologous pQAC/MVA-N and MLV resulted in a significant reduction in clinical severity with the birds asymptomatic when compared to unvaccinated PBS group birds (FIG. 5A). Viral RNA in lachrymal fluid and tracheal swabs were evaluated using qRT-PCR. Only the best performing experimental vaccine group as determined by viral shedding in lachrymal fluid along with the control groups was taken for quantifying viral shedding in the tracheal swabs. A significant reduction in viral load was observed both in the lachrymal fluid and swabs of pQAC/MVA-N vaccinated birds in comparison to the unvaccinated and 2×MVA-N vaccinated birds (FIG. 5B). More importantly, reduction in viral load in tracheal swabs was comparable to levels seen in commercial MLV vaccinated birds (FIG. 5C). In contrast, no reduction in viral load was observed in 2×MVA-N vaccinated birds, which correlated well with clinical severity scoring (FIGS. 5A and 5B). Vaccination with the heterologous pQAC/MVA-N confers protection against IBV challenge significantly higher than the homologous 2×MVA-N (FIG. 5B). This protection might be attributed to the induction of CD8+ and TCRy8+ memory T-cell responses (FIG. 4).

Impact of MPLA Addition on IBV Vaccine Protection.

Figure 6:
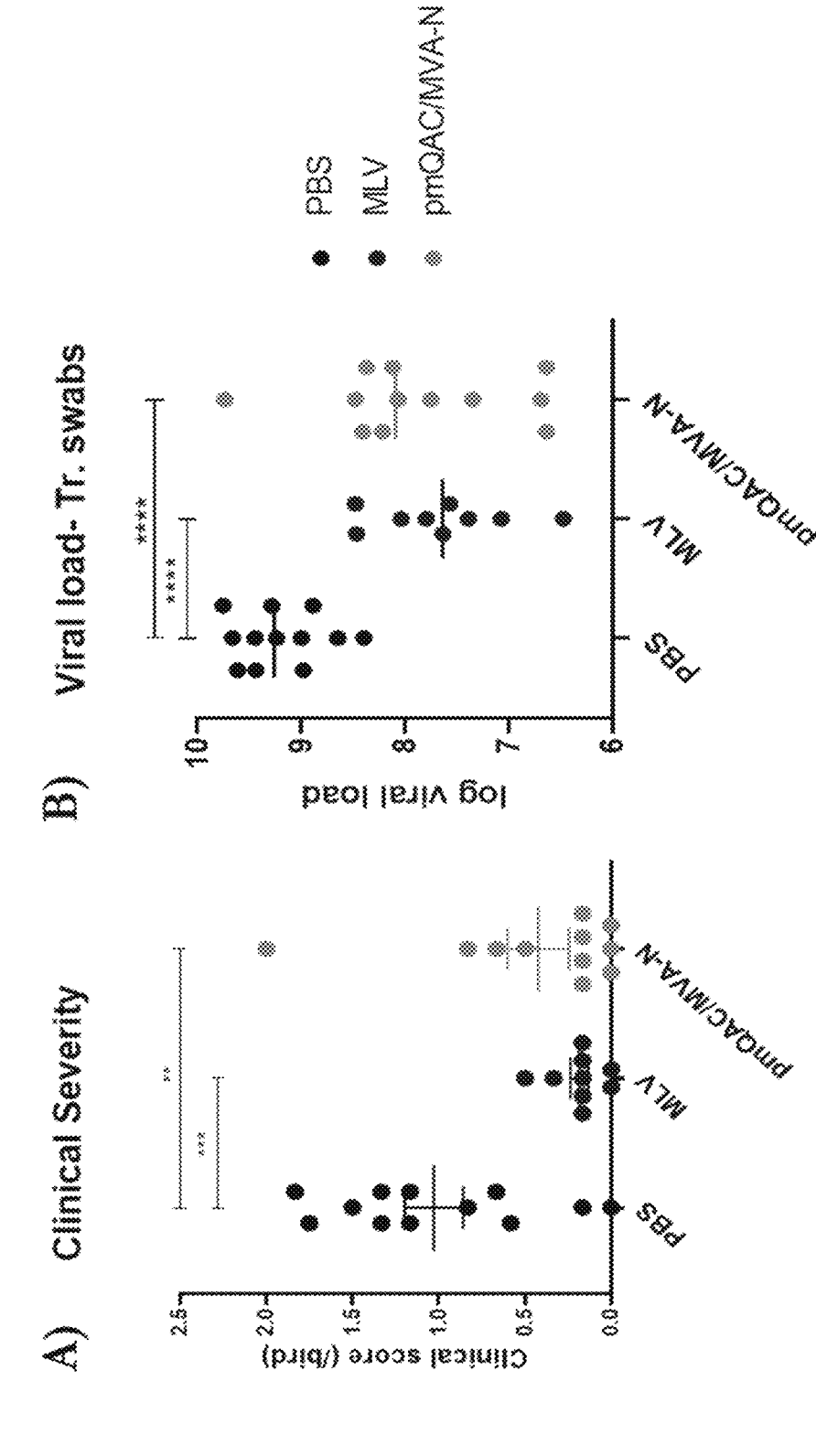
FIG. 6. Protective efficacy of the MPLA-QAC triple adjuvant system. a) Clinical sign severity represented as average score/bird over 8 days post challenge in each group. b) IBV log viral load in tracheal swab at 6 days post challenge Significance (*, P<0.001; **, P<0.0001) was determined by one-way ANOVA with multiple comparisons. Data show means±SEM.
Figure 7:
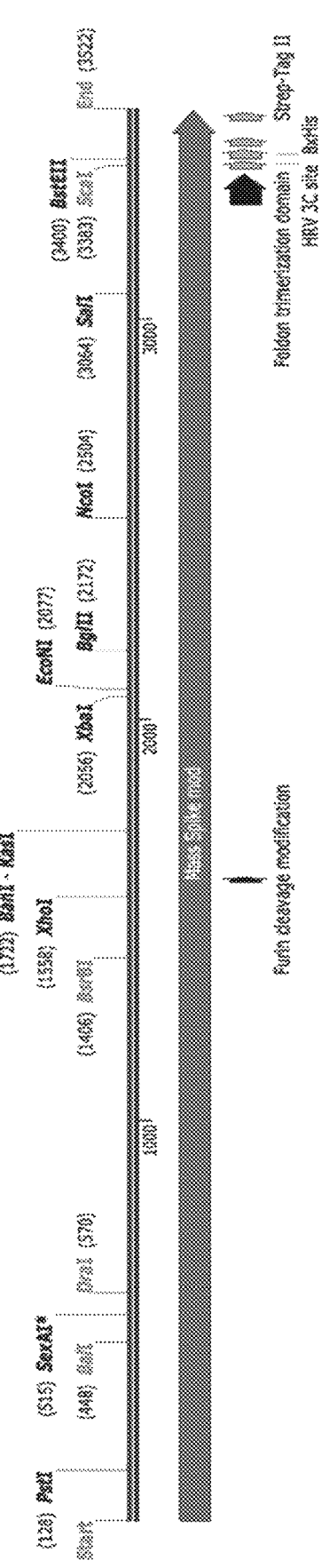
FIG. 7. Shows a map of the Mass41 S antigen with the modified 7 features (codon optimization is not shown with an arrow). All of the other sequences below have the same features.

MPLA is a potent mucosal adjuvant and TLR 4 ligand that stimulates expression of inflammatory-related genes, important of viral control in poultry. We hypothesized that inclusion of MPLA in addition to Quil-A® and Chitosan would further improve protection observed with pQAC/MVA-N vaccination. To investigate this, we immunized SPF birds with a triple adjuvant system (MPLA+QAC) loaded with pCAG-N plasmid at day −1 followed by MVA-N immunization (pmQAC/MVA-N) at day −14 similar to the pQAC/MVA-N group in the previous trial. Reduction in clinical severity and viral burden in tracheal swabs was observed comparable to the MLV group (FIGS. 6A-B). Protective efficacy of pmQAC/MVA-N was very similar to and not significantly different from pQAC/MVA-N (FIGS. 6A-B). Our results indicate that addition of MPLA does not improve vaccine performance. Overall, these results highlight the ability of the heterologous vaccine strategy to elicit potent IBV specific T-cell responses and protect vaccinated birds against virulent IBV challenge.

Discussion

Many experimental viral vectored vaccines primarily based on Newcastle Disease Virus (NDV) have been developed against IBV [31, 44, 45]. Recombinant NDV encoding for IBV Spike protects against homologous challenge and resulted in a reduction of clinical severity and viral shedding

[31, 45]. Recombinant MVA based vaccines have been developed for use in chickens against Infectious Bursal Disease Virus (IBDV) and Influenza[46-48]. The heterologous vaccine strategy involving a DNA prime followed by a viral vector booster dose has been evaluated against multiple human and animal viruses with modest success[37, 38, 49-51]. Intranasally administered vaccines are highly favorable for mass vaccinations in the field. Unfortunately, mucosal surfaces are vaccine hostile leading to poor immunogen uptake and bioavailability, rapid degradation and weak immune responses[27]. In a previous study, we demonstrated the ability of a nano adjuvant system, QAC to facilitate the intranasal delivery of DNA immunogens leading to a protection against IBV in poultry and SARS-COV-2 in transgenic mice [30, 37, 38]. In this study we evaluated the efficacy of an intranasally delivered heterologous QAC complexed DNA prime-MVA boost vaccine strategy. To our knowledge, the use of heterologous and MVA based vaccine strategies against IBV infection in chickens have not been extensively studied.

DNA viral vectors like MVA can accommodate and stably express multiple foreign immunogens, making them ideal candidates for vaccine use. In our hands, although the recombinant MVA-N had similar replication rates in cell-culture when compared to the parental MVA-GFP, the titers were 100-fold lower, albeit non-significant. This could mean that constitutive expression of IBV N-6×His protein potentially weakened the MVA vector replication in permissive CEF cells. The safety and efficacy of MVA-based vaccines in chicken hosts have been well documented[52-54]. Experimental MVA-hemagglutinin based influenza vaccines protects chickens against both lethal high- and low-pathogenicity avian influenza[52, 53]. Furthermore, the safety and replication of MVA in chicken embryos have been extensively characterized with no embryonic death observed even after in ovo inoculation[54]. We have previously shown that QAC based DNA vaccines are well tolerated by chicken hosts when administered via the IN and in ovo routes. Similarly, we observed that chickens intranasally administered MVA-N and pQAC/MVA-N did not show any signs of respiratory distress, in appetence or depression pre-challenge.

Very few studies have investigated the efficacy of MVA based vaccines in poultry. Ocular administration of MVA based flu vaccine protects birds against avian influenza challenge[47]. Mixing and matching viral vector and nucleic acid SARS-COV-2-vaccines also boost the immunogenicity of homologous vaccines[55, 56]. In our hands, the heterologous DNA prime followed by MVA boost was more immunogenic and protective than the homologous MVA vaccination. Reduction in clinical severity and viral burden both in lachrymal fluid and tracheal swabs were observed to levels comparable with MLV vaccination. The protection is most likely due to the induction of local lymphocyte responses by the pQAC-N priming followed by the expansion of T-cells facilitated by the MVA-N boost. We observed a similar phenomenon with our QAC-based COVID-19 vaccines in mice, where the heterologous DNA/MVA vaccine was more immunogenic than the homologous vaccine strategy[37, 38].

In a previous study we showed that 2 doses of pQAC-N vaccine protected vaccinated SPF and commercial birds against IBV challenge comparable to protection observed with MLV[30]. A robust T-cell immune response without a complementing humoral response was induced post vaccination with 2×pQAC-N. We hypothesized that boosting with MVA viral vector instead of DNA vaccine would further expand CD4+ T-cells leading to an induction of complementing humoral responses. We observed that immunization with MVA-N, both in the homologous and heterologous group did not lead to significant induction of both IgY and IgA as assayed using IBV specific binding ELISA. Instead, low level IBV-specific IgA and IgY was observed in the experimental vaccine groups at 3 dpc, indicating presence of an anamnestic response with pQAC—N based vaccines. In contrast, significant induction of humoral responses was observed with commercial MLV vaccine. Irrespective of the vaccine platform used, homologous MVA and heterologous DNA/MVA used in this study and homologous DNA used in the previous study, significant induction of N specific humoral responses are not observed[30]. The absence of humoral responses could be a consequence of using the N immunogen exclusively and not the vaccine platform itself. The N protein here will be intracellularly expressed in cells that take up the vaccine and not secreted. Moreover, it is unlikely that antibodies generated against N will be neutralizing given the intra-virion nature of the protein. With mouse hepatitis virus (MHV), a CoV infecting mice, N specific antibodies fail to neutralize MHV in cell culture[57].

Previously, sequential immunization approach of DNA prime-viral vector boost has led to the initial induction of cell-mediated immune (CMI) responses followed by MVA boost which expands induced CD8+ T-cells and Th1 T-cells [58]. We have previously shown that the potency of unadjuvanted plasmid DNA vaccine was enhanced by QAC nanoparticle formulation leading to induction of robust CD8+ and TCRγδ+ T-cells, potentially a hallmark of the QAC adjuvant system[30]. Similarly, lung cells harvested from pQAC/MVA-N immunized chickens responded well to IBV-N antigen recall stimulation. Furthermore, higher stimulation of TCRγδ+ and CD8+ T-cells was observed in pQAC/MVA-N immunized chickens, albeit non-significant. Although no significance was observed in T-cell specific responses, statistically higher proliferation was observed with total lung cells. This could mean that there are other lymphocytes (non TCRγδ+, CD8+ or CD4+ T-cells) in the lungs responding to IBV antigen that were not specifically evaluated in this study. We believe that an MVA boost after DNA prime further expanded the lung lymphocytes elicited by the initial DNA vaccination leading to protection. These results are in accordance with our previous data where a similar heterologous DNA/MVA vaccine elicited better local type-1 and type-17 T-cell responses in mice not observed with the homologous vaccine strategy[38]. Further studies are still warranted to evaluate the exact mechanism of action for the pQAC/MVA-N vaccine.

To further improve on the efficacy of the pQAC/MVA-N vaccine we added MPLA to our QAC vaccine formulation. MPLA is a synthetic low toxic form of LPS can engage with TLR4 (toll-like receptor) leading to an enhanced Th1 response[59]. MPLA is the only licensed TLR agonist approved for human use and is currently used as part of AS04 adjuvant in hepatitis B and human papillomavirus vaccines[60, 61]. Engagement of TLRs by agonists like lipopolysaccharides (LPS), Poly I:C and CpG dinucleotides leads to a cascade of intracellular signaling leading to induction of factors and cytokines which enhance immunity [62]. The new tri-adjuvant system based heterologous vaccine dubbed pmQAC/MVA-N with MPLA did not significantly improve protection observed with pQAC/MVA-N when administered intranasally.

Results presented here highlight the utility of a nanoadjuvant complexed DNA prime/viral vector boost vaccine strategy against IBV in chickens which reduces clinical severity and viral load in trachea and lachrymal fluid. The heterologous vaccine strategy outperformed the homologous MVA/MVA immunization and resulted in the induction of local-IBV specific T-cells in the lungs. Moreover, the protection observed with the heterologous vaccine strategy was very comparable with the commercial MLV vaccine's efficacy.

In general, CD8+ T-cells are important for early protection against IBV infection but CD4+ T-cells and systemic humoral responses are needed for sterilizing long term immunity[63]. We did not observe IBV specific antibody responses with the heterologous vaccine. The use of additional adjuvants and a secreted IBV S protein as an additional immunogen to the pQAC/MVA-N formulation could help in generating a complementing humoral immune response [64]. 2-dose vaccine regimens like the heterologous vaccine strategy described here might also have poor field applicability. Single dose vaccines administered at day −1 are preferred for poultry considering the need for early protection against IBV and the short lifespan of broilers in the poultry industry. Many experimental MVA based vaccines for use in humans are currently undergoing clincal trials. Therefore, use of MVA in poultry might confer people coming in contact with vaccinated birds with pre-existing immunity against the viral vector limiting the efficacy of subsequent human MVA based vaccines. That being said, the utility of this heterologous vaccine platform can be extended for use against other respiratory coronaviruses which necessitate robust local immune responses for protection. As highlighted with the ongoing COVID-19 pandemic, mix and match heterologous vaccines can not only improve immunogenicity, but also help in mitigating global vaccine supply chain shortages.

REFERENCES

1. Zhang, G., et al., *Animal coronaviruses and SARS-COV-2*. Transbound Emerg Dis, 2020.
2. Wan, Y., et al., *Receptor recognition by novel coronavirus from Wuhan: An analysis based on decade-long structural studies of SARS*. J Virol, 2020.
3. Ignjatovi-ç, J. and S. Sapats, *Avian infectious bronchitis virus*. Revue scientifique et technique (International Office of Epizootics), 2000. 19(2): p. 493-508.
4. Britton, P., et al., *Modification of the avian coronavirus infectious bronchitis virus for vaccine development*. Bioengineered Bugs, 2012. 3(2): p. 114-119.
5. Geilhausen, H. E., F. B. Ligon, and P. D. Lukert, *The pathogenesis of virulent and avirulent avian infectious bronchitis virus*. Archiv für die gesamte Virusforschung, 1973. 40(3-4): p. 285-290.
6. Agriculture, U. S. D.o. *Poultry—Production and Value 2020 Summary*. 2021; Available from: www.nass.usda-.gov/Publications/Todays_Reports/reports/plva0421.pdf.
7. Geilhausen, H. E., F. B. Ligon, and P. D. Lukert, *The pathogenesis of virulent and avirulent avian infectious bronchitis virus*. Archiv fr die gesamte Virusforschung, 1973. 40(3-4): p. 285-290.
8. Jordan, B., *Vaccination against infectious bronchitis virus: A continuous challenge*. Vet. Microbiol., 2017.
9. Jackwood, M. W., et al., *Infectious bronchitis virus field vaccination coverage and persistence of Arkansas-type viruses in commercial broilers*. Avian Dis, 2009. 53(2): p. 175-83.
10. Hopkins S R, Y. H. J., *Reversion to virulence of chicken-passaged infectious bronchitis vaccine virus*. Avian Diseases, 1986.

11. Mckinley, E. T., D. A. Hilt, and M. W. Jackwood, *Avian coronavirus infectious bronchitis attenuated live vaccines undergo selection of subpopulations and mutations following vaccination.* Vaccine, 2008. 26(10): p. 1274-84.

12. Lee, C. W. and M. W. Jackwood, *Origin and evolution of Georgia 98 (GA98), a new serotype of avian infectious bronchitis virus.* Virus Research, 2001. 80(1-2): p. 33-39.

13. Cook, J. K., M. Jackwood, and R. C. Jones, *The long view: 40 years of infectious bronchitis research.* Avian Pathol, 2012. 41(3): p. 239-50.

14. Fraga, A. P., et al., *Emergence of a New Genotype of Avian Infectious Bronchitis Virus in Brazil.* Avian Diseases, 2013. 57(2): p. 225-232.

15. de Wit, J. J., J. K. A. Cook, and H. M. J. F. van der Heijden, *Infectious bronchitis virus in Asia, Africa, Australia and Latin America—history, current situation and control measures.* Brazilian Journal of Poultry Science, 2010. 12(2): p. 97-106.

16. AgriLabs, *First DNA vaccine licensed for chickens.* 2017.

17. Zhang, P., et al., *Astragalus polysaccharides enhance the immune response to avian infectious bronchitis virus vaccination in chickens.* Microb Pathog, 2017. 111: p. 81-85.

18. Kapczynski, D. R., et al., *Protection of chickens from infectious bronchitis by in ovo and intramuscular vaccination with a DNA vaccine expressing the SI glycoprotein.* Avian Dis, 2003. 47(2): p. 272-85.

19. Guo, Z., et al., *Priming with a DNA vaccine and boosting with an inactivated vaccine enhance the immune response against infectious bronchitis virus.* J Virol Methods, 2010. 167(1): p. 84-9.

20. Tan, L., et al., *Infectious bronchitis virus poly-epitope-based vaccine protects chickens from acute infection.* Vaccine, 2016. 34(44): p. 5209-5216.

21. Tian, L., et al., *The immunoreactivity of a chimeric multi-epitope DNA vaccine against IBV in chickens.* Biochem Biophys Res Commun, 2008. 377(1): p. 221-5.

22. Tang, M., et al., *Enhancement of the immunogenicity of an infectious bronchitis virus DNA vaccine by a bicistronic plasmid encoding nucleocapsid protein and interleukin-2.* J Virol Methods, 2008. 149(1): p. 42-8.

23. Tan, B., et al., *Coadministration of chicken GM-CSF with a DNA vaccine expressing infectious bronchitis virus (IBV) SI glycoprotein enhances the specific immune response and protects against IBV infection.* Arch Virol, 2009. 154(7): p. 1117-24.

24. Yan, F., et al., *Protection of chickens against infectious bronchitis virus with a multivalent DNA vaccine and boosting with an inactivated vaccine.* J Vet Sci, 2013. 14(1): p. 53-60.

25. Yang, T., et al., *Multivalent DNA vaccine enhanced protection efficacy against infectious bronchitis virus in chickens.* J Vet Med Sci, 2009. 71(12): p. 1585-90.

26. Liu, M. A., *DNA vaccines: a review.* J Intern Med, 2003. 253(4): p. 402-10.

27 Borges, O., et al., *Preparation of coated nanoparticles for a new mucosal vaccine delivery system.* Int J Pharm, 2005. 299(1-2): p. 155-66.

28 Brock A. Kingstad-Bakke, S. S. C., YashdeepPhanse, Kathleen A. Ross, MasatoHatta, M. Suresh, Yoshihiro Kawaoka, Jorge E. Osorio, Balaji Narasimhan, Adel M. Talaat, *Effective mosaic-based nanovaccines against avian influenza in poultry.* Vaccine, 2019.

29. Oyewumi, M. O., A. Kumar, and Z. Cui, *Nano-microparticles as immune adjuvants: correlating particle sizes and the resultant immune responses.* Expert Rev Vaccines, 2010. 9(9): p. 1095-107.

30. Chandrasekar, S. S., et al., *A Novel Mucosal Adjuvant System for the Immunization Against Avian Coronavirus Causing Infectious Bronchitis.* J Virol, 2020.

31. Shirvani, E., et al., *A Recombinant Newcastle Disease Virus (NDV) Expressing S Protein of Infectious Bronchitis Virus (IBV) Protects Chickens against IBV and NDV.* Sci Rep, 2018. 8(1): p. 11951.

32. Falchieri, M., et al., *Avian metapneumoviruses expressing Infectious Bronchitis virus genes are stable and induce protection.* Vaccine, 2013. 31(22): p. 2565-71.

33. Harari, A., et al., *An HIV-1 clade C DNA prime, NYVAC boost vaccine regimen induces reliable, polyfunctional, and long-lasting T cell responses.* J Exp Med, 2008. 205(1): p. 63-77.

34. Park, S. H., et al., *Efficient induction of T helper 1 CD4+ T-cell responses to hepatitis C virus core and E2 by a DNA prime-adenovirus boost.* Vaccine, 2003. 21(31): p. 4555-64.

35. Lu, S., *Heterologous prime-boost vaccination.* Curr Opin Immunol, 2009. 21(3): p. 346-51.

36 Peng, S., et al., *Optimization of heterologous DNA-prime, protein boost regimens and site of vaccination to enhance therapeutic immunity against human papillomavirus-associated disease.* Cell Biosci, 2016. 6: p. 16.

37. Chandrasekar, S. S. P., Y.; Riel, M.; Hildebrand, R. E.; Hanafy, M.; Osorio, J. E.; Abdelgayed, S. S.; Talaat, A. M., *Systemic Neutralizing Antibodies and Local Immune Responses Are Critical for the Control of SARS-Cov-2.* Viruses, 2022.

38. Chandrasekar, S. S., et al., *Localized and Systemic Immune Responses against SARS-COV-2 Following Mucosal Immunization.* Vaccines (Basel), 2021. 9(2).

39. Hernandez, R., & Brown, D. T., *Growth and Maintenance of Chick Embryo Fibroblasts (CEF).* May 2010, Current Protocols in Microbiology: John Wiley & Sons, Inc.

40. MUENCH, L. J. R. A. H., *A SIMPLE METHOD OF ESTIMATING FIFTY PERCENT ENDPOINTS.* THE AMERICAN JOURNAL OF HYGIENE, 1938. 27.

41. Stading, B. R., et al., *Infectivity of attenuated poxvirus vaccine vectors and immunogenicity of a raccoonpox vectored rabies vaccine in the Brazilian Free-tailed bat (Tadarida brasiliensis).* Vaccine, 2016. 34(44): p. 5352-5358.

42. Ganapathy, K., P. W. Cargill, and R. C. Jones, *A comparison of methods of inducing lachrymation and tear collection in chickens for detection of virus-specific immuoglobulins after infection with infectious bronchitis virus.* Avian Pathol, 2005. 34(3): p. 248-51.

43. Orr-Burks, N., et al., *Immunoglobulin A as an early humoral responder after mucosal avian coronavirus vaccination.* Avian Dis, 2014. 58(2): p. 279-86.

44. Shirvani, E. and S. K. Samal, *Comparative Protective Efficacies of Novel Avian Paramyxovirus-Vectored Vaccines against Virulent Infectious Bronchitis Virus in Chickens.* Viruses, 2020. 12(7).

45 Abozeid, H. H., et al., *Development of a recombinant Newcastle disease virus-vectored vaccine for infectious bronchitis virus variant strains circulating in Egypt.* Vet Res, 2019. 50(1): p. 12.

46. Boyd, A. C., et al., *Towards a universal vaccine for avian influenza: protective efficacy of modified Vaccinia virus Ankara and Adenovirus vaccines expressing conserved* influenza antigens in chickens challenged with low pathogenic avian influenza virus. Vaccine, 2013. 31(4): p. 670-5.

47 Ducatez, M. F., et al., Low pathogenic avian influenza (H9N2) in chicken: Evaluation of an ancestral H9-MVA vaccine. Vet Microbiol, 2016. 189: p. 59-67.

48. Zanetti, F. A., et al., Evaluation of modified vaccinia virus Ankara expressing VP2 protein of infectious bursal disease virus as an immunogen in chickens. J Vet Sci, 2012. 13(2): p. 199-201.

49. Alharbi, N. K., et al., ChAdOx1 and MVA based vaccine candidates against MERS-CoV elicit neutralising antibodies and cellular immune responses in mice. Vaccine, 2017. 35(30): p. 3780-3788.

50. Maeto, C., et al., Novel mucosal DNA-MVA HIV vaccination in which DNA-IL-12 plus cholera toxin B subunit (CTB) cooperates to enhance cellular systemic and mucosal genital tract immunity. PLOS One, 2014. 9(9): p. e107524.

51. Manrique, M., et al., Nasal DNA-MVA SIV vaccination provides more significant protection from progression to AIDS than a similar intramuscular vaccination. Mucosal Immunol, 2009. 2(6): p. 536-50.

52. Veits, J., et al., Protective efficacy of several vaccines against highly pathogenic H5N1 avian influenza virus under experimental conditions. Vaccine, 2008. 26(13): p. 1688-96.

53 Kapczynski, D. R., et al., Vaccine protection of chickens against antigenically diverse H5 highly pathogenic avian influenza isolates with a live HVT vector vaccine expressing the influenza hemagglutinin gene derived from a clade 2.2 avian influenza virus. Vaccine, 2015. 33(9): p. 1197-205.

54. Langenmayer, M. C., et al., Tracking Modified Vaccinia Virus Ankara in the Chicken Embryo: In Vivo Tropism and Pathogenesis of Egg Infections. Viruses, 2018. 10(9).

55. Barros-Martins, J., et al., Immune responses against SARS-COV-2 variants after heterologous and homologous ChAdOx1 nCOV-19 BNT162b2 vaccination. Nat Med, 2021.

56. Schmidt, T., et al., Immunogenicity and reactogenicity of heterologous ChAdOx1 nCOV-19 mRNA vaccination. Nat Med, 2021.

57. Zhao, P., et al., Immune responses against SARS-coronavirus nucleocapsid protein induced by DNA vaccine. Virology, 2005. 331(1): p. 128-35.

58 Kardani, K., A. Bolhassani, and S. Shahbazi, Prime-boost vaccine strategy against viral infections: Mechanisms and benefits. Vaccine, 2016. 34(4): p. 413-423.

59. Fisher, B. S., et al., Oral Immunization with HIV-1 Envelope SOSIP trimers elicits systemic immune responses and cross-reactive anti-VIV2 antibodies in non-human primates. PLOS One, 2020. 15(5): p. e0233577.

60. Didierlaurent, A. M., et al., AS04, an aluminum salt-and TLR4 agonist-based adjuvant system, induces a transient localized innate immune response leading to enhanced adaptive immunity. J Immunol, 2009. 183(10): p. 6186-97.

61. Evans, J. T., et al., Enhancement of antigen-specific immunity via the TLR4 ligands MPL adjuvant and Ribi.529. Expert Rev Vaccines, 2003. 2(2): p. 219-29.

62. Gregg, K. A., et al., Rationally Designed TLR4 Ligands for Vaccine Adjuvant Discovery. mBio, 2017. 8(3).

63. Chhabra, R., et al., Mucosal, Cellular, and Humoral Immune Responses Induced by Different Live Infectious Bronchitis Virus Vaccination Regimes and Protection Conferred against Infectious Bronchitis Virus Q1 Strain. Clin Vaccine Immunol, 2015. 22(9): p. 1050-9.

64. Yu, J., et al., DNA vaccine protection against SARS-COV-2 in rhesus macaques. Science, 2020. 369(6505): p. 806-811.

What is claimed:

1. A vaccine composition comprising a polynucleotide that encodes an infectious bronchitis virus (IBV) spike(S) protein, an IBV nucleocapsid (N) protein, or both the S protein and the N protein, wherein the sequence encoding the S protein comprises one of SEQ ID NOs: 22, 24, 26, 28, 30, or 32 or a sequence with at least 90% identity to one of one of SEQ ID NOs: 22, 24, 26, 28, 30, or 32 and, wherein the sequence encoding the N protein comprises one of SEQ ID NOs: 36 or 38 or a sequence with at least 90% identity to one of SEQ ID NOs: 36 or 38.

2. The vaccine composition of claim 1, further comprising an adjuvant.

3. The vaccine composition of claim 2, wherein the adjuvant comprises disaggregated spherical nanostructures comprising a saponin fraction isolated from an extract of the bark of *Quillaja saponaria* (Quil A) and chitosan, and wherein the Quil A and chitosan are present at a ratio between 1:15 and 1:100.

4. The vaccine composition of claim 3, wherein the chitosan is functionalized by treatment with 5-formyl-2-furan sulfonic acid and sodium borohydride, such that the chitosan surface is negatively charged.

5. A method of inducing an immune response against infectious bronchitis virus (IBV) in a subject, the method comprising:
   (a) administering a first vaccine composition comprising the vaccine composition of claim 1 in an amount effective to induce the immune response against at least one IBV antigen in the subject; and
   (b) administering a second vaccine composition comprising a protein, nucleic acid or viral vectored vaccine composition, the second vaccine composition comprising a polynucleotide encoding an IBV S protein, an IBV N protein, or both or comprising an IBV polypeptide selected from an IBV S protein, an IBV N protein or both, wherein administration of the first vaccine composition and the second vaccine composition induces the immune response against IBV in the subject, wherein administration of the second vaccine composition occurs at least two weeks after administration of the first vaccine composition, and wherein both the first vaccine composition and the second vaccine composition are administered by a route selected from intranasal, intramuscular, oral, or in ovo, and wherein the first vaccine composition and the second vaccine composition are administered via the same route or different routes.

6. The method of claim 5, wherein the first vaccine composition and the second vaccine composition are administered intranasally.

7. The method of claim 5, wherein the subject is an avian subject.

8. The method of claim 7, wherein the avian subject is a chicken.

9. The method of claim 5, wherein the second vaccine composition comprises a protein comprising an infectious bronchitis virus (IBV) (S) protein, an IBV nucleocapsid (N) protein, or both the S protein and the N protein.

10. A method comprising administering the vaccine composition of claim 1 to a subject.

11. The method of claim 10, wherein the subject is an avian subject.

12. The method of claim 10, wherein the vaccine composition is administered intranasally to the subject.

13. A vaccine composition comprising a viral vector comprising an infectious bronchitis virus (IBV) (S) protein, an IBV nucleocapsid (N) protein, or both the S protein and the N protein, wherein the viral vector further comprises a polynucleotide encoding the S protein, the N protein or both the S protein and the N protein, and wherein the sequence encoding the S protein comprises one of SEQ ID NOs: 22, 24, 26, 28, 30, or 32 or a sequence with at least 90% identity to one of one of SEQ ID NOs: 22, 24, 26, 28, 30, or 32 and, wherein the sequence encoding the N protein comprises one of SEQ ID NOs: 36 or 38 or a sequence with at least 90% identity to one of SEQ ID NOs: 36 or 38.

14. The vaccine composition of claim 13, wherein the viral vector is selected from an adeno-associated virus or a poxvirus.

15. The vaccine composition of claim 13, further comprising an adjuvant.

16. The vaccine composition of claim 15, wherein the adjuvant comprises disaggregated spherical nanostructures comprising a saponin fraction isolated from an extract of the bark of *Quillaja saponaria* (Quil A) and chitosan, and wherein the (Quil A) and chitosan are present at a ratio between 1:15 and 1:100.

17. The vaccine composition of claim 16, wherein the chitosan is functionalized by treatment with 5-formyl-2-furan sulfonic acid and sodium borohydride, such that the chitosan surface is negatively charged.

18. A method comprising administering the vaccine composition of claim 13 to a subject.

19. The method of claim 18, wherein the subject is an avian subject.

20. The method of claim 18, wherein the vaccine composition is administered intranasally to the subject.

* * * * *

```
SEQUENCE LISTING

Sequence total quantity: 47
SEQ ID NO: 1           moltype = DNA  length = 3522
FEATURE                Location/Qualifiers
source                 1..3522
                       mol_type = other DNA
                       organism = Infectious Bronchitis Virus
SEQUENCE: 1
atgcttgtga cgcctctgct gctggtgact ttgctgtgtg ccctctgctc cgccgtcctg  60
tacgatagct cttcatatgt gtactattat cagagcgcct tccggccacc taacggttgg  120
catctgcagg gtggcgcgta tgccgttgtc aatatctctt cagaatttaa taatgcaggg  180
tccagtagcg gttgcacggt cgggatcatc cacggtggcc gcgtggtgaa cgcctcttca  240
attgccatga ctgctccatc ttccggcatg gcctggtcct cttcccaatt ctgtactgct  300
cactgtaact ttagcgacac aaccgtcttt gttacacatt gttacaaaca tggtggctgt  360
cccattaccg gaatgttgca acaaaatctt atccgggtga gcgcaatgaa gaacggtcaa  420
ctcttttaca atttgacggt gtctgtggcc aagtacccaa cgtttcgcag ctttcagtgt  480
gtcaacaacc tcacatccgt ctacctcaat ggagacctgg tgtataccag taacgagacc  540
attgatgtta cttcagcagg agtctacttt aaagcaggtg gccccattac atataaggtt  600
atgcgggaag tcaaagcttt ggcatatttc gtcaatggca ctgctcagga cgttatcctt  660
tgtgatggat ccccaagggg tttgctggct tgtcaataca acaccgggaa cttttcagac  720
ggattttacc catttactaa tagttctttg gttaaacaga aattcattgt gtaccgggag  780
aactccgtta ataccacatg tactctgcac aactttatct tccacaacga aacaggcgcg  840
aatcctaatc caagcggtgt acagaatatt caaacctatc agacgaaaac ggcccagtca  900
ggatactaca attttaactt tagctttctc agcagctttg tgtataaaga aagcaatttc  960
atgtatgggt cctaccatcc ctcttgtaat tttcgactgg aaacgattaa taacgggttg  1020
tggttcaatt ctctcagtgt cagcattgcc tatggaccac tccaaggcgg ctgcaagcag  1080
tccgttttca aggggagagc aacatgttgt tacgcttact cttacggcgg cccatccctg  1140
tgcaaaggtg tgtactccgg agagttggat cataactttg aatgcgggct tctggtttac  1200
gttactaagt ccggcggcag caggatacaa acggctacag aaccacccgt cattacccaa  1260
aacaactaca ataatatcac actcaacacg tgtgtagatt ataacatcta cgggcggaca  1320
ggtcagggct tcatcacgaa tgtcaccgat tccgcggttt catataatta cctggccgat  1380
gcaggacttg cgattttgga cacgagcggg tccatagata tatttgtcgt gcagggagag  1440
tacgggctca actactataa agtgaatcca tgtgaggacg taaatcaaca atttgttgtt  1500
tccggcggta aacttgtggg aatcctgaca agcagaaatg aaactggctc tcaacttctc  1560
```

-continued

```
gagaaccaat tctacatcaa aataacaaac ggtacgggtg gcggcgttcc aagcatcact  1620
gagaatgtgg cgaattgccc ttatgtctca tatggcaagt tctgtattaa acctgatgga  1680
tccatcgcca ctatcgtacc taagcagttg gaacaatttg tggcgccatt gtttaatgtg  1740
actgagaacg tactgattcc caattcattt aacctcacgg tgacagacga atatattcaa  1800
actcgtatgg ataaggtaca aattaactgc ctgcaatatg tgtgcggaag tagtttggat  1860
tgcagaaaac tgtttcaaca atatggacca gtatgtgata atattttgag cgtggttaat  1920
tccgtaggcc agaaagaaga tatggagctc ttgaactttt actcaagcac taagccagct  1980
ggatttaaca ccccggtact gagcaatgtc tctacagggg aatttaacat atcattgttg  2040
ttgaccaccc cgagctctag acgaaagcgt tccctgatcg aggacctctt gtttacgagc  2100
gtggagtctg tcggtctgcc aacgaacgac gcgtataaga actgcacggc agggcccttg  2160
gggttcttca aagatcttgc atgcgcacgg gaatacaacg ggctcctcgt cttgccgccc  2220
ataataaccg cggagatgca ggcgttgtat acttcatccc tggttgcttc aatggcattc  2280
ggtggaataa cagctgccgg agctatcccc tttgccacgc aactccaggc caggattaac  2340
catctcggta ttacccaatc cctgctgctc aagaaccaag agaaaatcgc ggcaagtttc  2400
aataaagcga taggtcatat gcaggaagga tttcgcagta cgtcattggc cttgcaacaa  2460
attcaagatg tcgtgtctaa gcaatctgcc atactcaccg aaaccatggc gagcctgaac  2520
aagaattttg gtgcaatttc atccgtaatt caggagattt atcaacaatt tgacgcaata  2580
caagcaaatg cacaagttga tagactgata actggacggc ttagcagtct ggctgtcctg  2640
gcatccgcca aacaagctga atatattaga gtatctcagc aaagggagct ggctacacaa  2700
aagattaacg agtgtgttaa aagtcaaagt atccgttaca gcttctgtgg caacggtcgc  2760
catgtcctta ccattcctca aaacgccccc aacggaattg ttttcataca ttttagttac  2820
accccgacga gtttcgtaaa tgtgaccgcc atcgtgggt tctgtgtcaa acctgcaaat  2880
gcatcccagt acgccatagt tcccgcgaat ggccggggta tatttattca agtcaatgga  2940
tcatactata tcacagcacg tgatatgtat atgccacggg caattaccgc tggcgacgtc  3000
gttacactta catcctgcca agccaactat gtatctgtta ataaaaccgt tattacaacc  3060
tttgtcgaca atgacgactt tgattttaac gacgagctca gtaaatggtg gaacgaaccg  3120
aagcatgagc tgcccgattt tgacaaattt aattataccg tacccattct cgacatagac  3180
tctgaaattg ataggataca aggggtgatt caaggactga atgattccct tatcgacctt  3240
gagaaactgt ccatcctcaa aacatacatt aaatggcccg gctctggata catcctgaa  3300
gcccacgcg atggacaagc ttatgtccgg aaggacggtg agtgggtcct gctgtcaacc  3360
ttcctcggca ggagcctgga agtactgttt caagggccag gtcaccatca tcatcatcac  3420
catcacagcg cttggtcaca tccacaattc gagaaaggag gaggctcagg cggcggtggt  3480
tcaggcggat cagcatggtc ccatccccaa ttcgaaaagt ag                      3522
```

SEQ ID NO: 2             moltype = DNA   length = 3543
FEATURE                 Location/Qualifiers
source                  1..3543
                        mol_type = other DNA
                        organism = Infectious Bronchitis Virus
SEQUENCE: 2

```
atgttggtca aaagtctgtt cctcgtcact attttgttcg cactctgctc tgccaacctg  60
tacgataacg agtcattcgt gtattactac cagtcagcat tcaggcccgg gcacggttgg  120
cacctctacg gtggcgccta cgccgtcgtg aatgtctcct cagagaataa caacgccggg  180
accgcaccaa gctgcactgc tggggcaatc ggatattcta aaaatctctc cgcagcctcc  240
gtggctatga ctgctccttt gagtggcatg agctggtctg caaattcttt ctgtactgca  300
cattgcaact tcacctccta tattgtgttc gtcacacact gttataagag cggaagcaat  360
tcctgccccc tgaccggact gatccccagt ggctatatca ggattgcagc tatgaagcac  420
ggatccgcca tgccgggaca cttgttttac aatttgacgg tctcagtcac caagtatccc  480
aaattcagaa gcctgcagtg cgtgaataac tataccagcg tctacctcaa tggagacctg  540
gtctttacct caaattacac cgaggatgtg gttgctgccg gggttcattt taaaagtggg  600
ggccctatta cctataaggt aatgcgggaa gtgaaagccc tggcctactt tgtgaacggg  660
accgcacacg acgtgattct gtgcgatgat acccctaggg gactgctcgc ctgtcagtac  720
aatacgggga atttcagtga tggtttctac cctttcacca cacttccat cgtgaaagac  780
aaatttatcg tgtacaggga gtcttccgtt aatactaccc tcacactgac aaacttcacg  840
tttagcaatg agagcggagc tccccccaat actggggag tggacagttt tatcctctac  900
cagactcaga cagcccagtc tggctactac aacttcaact tcagctttct gagttcattc  960
gtgtacagag agtcttacta tatgtatggg agctaccacc cccggtgtag ttttcgacca  1020
gagacactga ataatggtct gtggttcaac tcactgtcag tatctctcac ctacgggccg  1080
attcaggtg gatgcaagca gagtgtgttc aatggtaagg ctacttgttg ttatgcctat  1140
tcttacgtg gcccacgggc ttgcaaaggg gtgtacagag gagaactgac gcaacacttc  1200
gagtgtgggc tgctggtcta cgtgactaaa agcgatggaa gccggattca aacagcgacc  1260
cagcctcctg ttcttaccca gaacttctac aacaatatta atttaggaaa atgtgtggac  1320
tacaatatct acggccgcat aggccagggc ctcatcacca atgtgacgga tctggctgtg  1380
tcctataact atctctccga cgccggactt gcgatattgg acacgagcgg agccatcgac  1440
atattcgtcg tacaaggtga gtacggccca aactactata aagttaaccc ttgcgaagat  1500
gtcaatcaac agttcgtagt gtccggcgga aaattagtgg gcatattaac atccagaaac  1560
gagaccggct cacaattgct ggaaaaccag ttctacataa agatcaccaa cggcacaggc  1620
ggcggcgttc catccgtaac cgaaaacgtt acaaactgtc catacgtctc ctatgggaag  1680
ttttgtatta aacctgatgg atccatttca gtgatcgtgc ctaaagaact tgaccagttc  1740
gtggccccat tgttgaacgt gactgagtac gtgctcatcc ctaacagctt caacctgact  1800
gtcacggatg aatatataca aaccagaatg gacaaaattc agataaactg tcttcagtat  1860
gtgtgcggga actcccttgc gtgcaggaag ctctttcagc agtatggacc cgtttgtgac  1920
aacattttga gcgtggttaa ctccgtggga cagaaagaag acatggagct ccttaatttt  1980
tacagcagca caaagcctgc aaggttcaat actccggtat tcagtaacct tagtactggg  2040
gagtttaaca taagcctctt gctgacccct cctcctccc gcgcaggag gagtttcatt  2100
gaagatctgc tgtttactag tgtcgaatcc gtgggactgc caacgacga cgcctataaa  2160
atgcggacgg ctgcccact cggattctg aaggacctgg cttgtgccag agaatataat  2220
ggccttcttg ttctgccacc aatcatcaca gccgagatgc aaaccctgta cacctcttct  2280
ttggtagcta gtatggcctt cggtgggatt acggctgccg gggctatccc ctttgccacc  2340
```

```
cagctccagg ctaggattaa ccaccttggg atcacccagt ctctgctcct caagaaccag   2400
gagaagatcg ccgcaagctt caataaagca ataggccaca tgcaagaggg cttccggtca   2460
accagcctgg ctttgcaaca gattcaggac gtcgttaaca aacagtctgc gatcctcacc   2520
gagacaatgt tggccttgaa taaaaacttc ggtgccattt ctagcgttat acaagatatt   2580
tatcaacaac ttgacagtat ccaagctgac gcacaggtgg atcggctgat tactggacgt   2640
ctttcaagtc tcagcgtgct ggcatctgca aagcagtcag aatacatcag ggtgtctcag   2700
cagcgggagc tggccacaca gaagatcaat gagtgcgtga agtcacagtc aatcagatac   2760
tcttttgtg gcaacgggcg acacgtgttg acaatcccac aaaatgcccc aaacgggatc   2820
gtgttcattc atttcactta cactccggaa tcttttatca atgtcacggc ggtcgtgggc   2880
ttctgtgtgt ctcctgcgaa cgccagccag tacgccattg tcccagcaaa cggtagaggg   2940
atattcatcc aggtcaacgg atcatactac atcactgccc gtgatatgta catgccccgg   3000
gacatcaccg ctggagacat cgtgactctg actagttgtc aggctaatta cgtcagcgtc   3060
aataaaacag tgatcaccac cttcgtagac aacgacgact tcgacttcga cgatgagctc   3120
tccaagtggt ggaatgagac caaacatgag ttacccgatt ttgataagtt caactacact   3180
gtccccattc tggacattga tagcgagatc gatcgcatac aggggggtcat ccagggcctg   3240
aatgacagcc ttatcgacct ggagacactt tccatcctca agacatacat taagtggcca   3300
ggctctgggt atattccaga agcacctagg gacggccagg cctacgtgcg gaaggatgga   3360
gaatgggtgt tgctctctac cttcctcggt aggtcactcg aagtcctgct tcaaggacca   3420
ggccatcacc atcaccacca ccatcattct gcctggtccc accctcagtt cgagaaaggg   3480
ggcgggagtg gtggtggggg gtcaggcggc agcgcttgga gccatcctca gttcgagaaa   3540
tga                                                                 3543
```

SEQ ID NO: 3                moltype = DNA   length = 3552
FEATURE                     Location/Qualifiers
source                      1..3552
                            mol_type = other DNA
                            organism = Infectious Bronchitis Virus
SEQUENCE: 3

```
atgctggtga agtcaccatt tatcgtgacg ctgctgtgcg ctttgtgctc agcaagtctt   60
tatgataacg gcagctatgt gtattactac caatccgcat ttagaccttc aattgggtgg   120
catcttcacg gcggagccta cgcagtggtg aatgtgaccc aggaatacaa caatgccggc   180
agtgcctcag agtgcactgc gggagcgata gtttggtcca aaaatttcag tgcagcaagt   240
gtggccatga ccgcccccca ttccgggatg agctggagtg ttaaacagtt ttgcactgct   300
cattgcaact ttaccaattt tgtcgtgttt gtgacgcatt gttttaagga cggcctcaat   360
acatgcccc tcaccggccg cattgatcag gggtatatta ggattgcagc gatgaagaat   420
accggaactg gccctcggga cttattctac aactttacag tctccgtgac taaatacccct   480
tcttttaaat ctctgcagtg tgtaaacaac cagacaagtg tctaccttaa cggggacctc   540
gtcttcactt ccaatgagac tgttgatgtg tcaggcgcgg gcgtgcactt caaggcagga   600
ggccccatca cctataaagt catgagagaa gtaaaggccc tcgcctactt tgtgaatggg   660
actgcccagg acgtgattct gtgtgactca tcccccaggg ggctgttagc atgtcagtat   720
aacaccggga attttttccga cggttttttac cccttcacga atagctccgt ggtgaaggag   780
aagttcatcg tgtatagcga gaacagcgtg aacactacac tggtcctgca taattttacg   840
ttctacaacg agtctgatgc cccacccaat tctcagcaat cctcagccgg tgtaggggga   900
cttactacgt accagacaca gaccgcccag agtggctatt acaattttaa cttcagcttt   960
ctttctagtt ttgtctataa agagagcaac ttcatgtatg gttcatatca tccacaatgt   1020
aattttcgtc cagagaatat taataatggg ttgtggttta actcactgtc cgtgtccatc   1080
acttacgggc ctctgcaagg cggttgtaaa caatcagtgt tcagtcaccg cgcaacttgt   1140
tgctatgcct atagttacaa cggtccccac atttgcaagg gtgtgtattc tggacagctg   1200
cacaataatt tcgaatgtgg attgctggtc tacatcacca aaaccgatgg ctcaaggatc   1260
caaacagcca ccacacccc cgttcggaca caacattttt acaataatat taccctgcac   1320
aaatgcgtgg agtacaacat ttatggcaga gtggggcagg gatttataac caacgtgaca   1380
gactctgtag ctggttacaa ttaccttcag gatgggggggc tcgctatcct tgacaccagt   1440
ggagcaatag atatatttgc tgtgcagggc ggatacgggc tgaattttta caaggtcaac   1500
ccgtgcgaag acgtcaacca gcagtttgtg gtgtccggtg aaacctggt tggcatcctc   1560
accagccgaa acgaaacgga cagccaacct ctcgagaatc agttttttcgt gaagctgatc   1620
aacggcaccg gcgggggggt gccctccata tccgaaaatg tgaccagctg ttcctttgtg   1680
agctacggca agttttgcat caagccagac ggttccatct ctactattgt accgaaggag   1740
atggagcagt ttgtagcgcc actgctgaac gtcactgaac atgtgctgat tcccgatagt   1800
tttaacctga ccgttactga cgaatacatc cagacacgaa tggacaaggt ccagattaac   1860
tgcctgcagt acgtgtgtgg caatagtttt gagtgtagac agctttttca acagtatggg   1920
ccagtttgcg acaacatcct gtcagtggtg aacagcgttg gccaaaagga agacatggag   1980
cttctgtcct tttactccag tacaaaaccg gccggctata taccccagt gttcaacatc   2040
agcacaggag acttcaatat ctctttactg cttcctccaa gttcagcgcc aagtggtcgg   2100
tccttcatcg aggaccttct ctttacctcc gtcgaaagtg ttggtcttcc tacagatgag   2160
gcatataaaa aatgtacagc gggccctctg ggcttcctga aggaccttgc atgtgcccgg   2220
gagtataatg ggctcttggt tctccccccc ataattaccg ccgagatgca aactttatat   2280
acttcttcac tggtcgcctc catggccctc ggaggtatca ccgccgctgg agcgattccg   2340
tttgcaaccc aattgcaggc ccgcattaac cacctgggaa taacccaaac agtgctcctg   2400
aaaaaccagg agaagatagc tgcctcattt aacaaggtag tcggtcacat gcaggaaggt   2460
tttaaaagca ctagcctcgc cctgcaacag attcaggatg ttgtgaataa gcaaagcgct   2520
attcttaccg aaactatggc ctccctgaac aaaaatttcg gagctatcag tagcgttatt   2580
caggagatct atcaacagct ggatgctatc caggccaatg ctcaagtcga taggctcatc   2640
acgggccgcc tcagtagcct gtctgtgctg ccagctcca agcaggccga gtacttacgg   2700
gtttccaac acgtgagtt ggccacacag aaaatcaac aatgcgtcaa aagtcagagt   2760
acgcgggtact ccttcgtgg caacgggaga catgttctta caatacccca gaacgcccca   2820
aatggcatcg tgtttataca ctttacctat acacccgagt cctttgtgaa cgtcaccgcg   2880
attgttggat tctgtataaa tccagccaac gcctcccaat acgccatagt ccccgccaac   2940
ggcagaggca tcttcatcca ggtgaacggc acttactaca tcactgctcg agacatgttt   3000
atgcctcgcg acattacagc cggagatgtt gtgacgctca cctcttgcca ggccaactac   3060
```

-continued

```
gtgagtgtga ataagacggt catcacaacc ttcgtcgaaa gcgacgattt cgacttcgac    3120
gacgaactca gcaagtggtg gaacgagaca aagcacgagt tccctgactt tgatcaattc    3180
aattacacca tacctgtgct gaatatcaca tacgatatcg acaaaatcga agaggttatc    3240
aagggcttga acgacagttt gatcgacctg gaaactctgt ccattctcaa gacgtatatc    3300
aagtggcccg gatcaggata tatccctgag gcccctaggg acggacaggc ttatgttcgt    3360
aaggacggcg agtgggtgct ttttgagtact tttctgggcc gcagcctgga ggtactcttt    3420
cagggccccg gacaccacca tcatcaccac caccactcag catggagtca cccccagttc    3480
gaaaaaggcg gcgggagtgg cggcgggggg agcggcggaa gcgcatggtc ccaccctcag    3540
tttgaaaaat ga                                                          3552
```

SEQ ID NO: 4                moltype = DNA   length = 3534
FEATURE                     Location/Qualifiers
source                      1..3534
                            mol_type = other DNA
                            organism = Infectious Bronchitis Virus

SEQUENCE: 4

```
atgctggtga agtctctgtt cacagttata cctctgttcg ccctctgcag cgctacgctc    60
tacgactctg gctcctacgt gtattactac caaagcgcct tccggccgcc gaatggctgg    120
cagcttcatg gaggagccta cgctgtcgtt aatgtgtcta cggagactgg ctccgcaaac    180
cggtgcacgg cgggtgcaat ctcattttca aagaacttta gcgcggcatc cgtggcaatg    240
acggccccag caaacgggat gacctggtca gacgcacaat tttgtactgc tcactgtaat    300
tttactaaca tcgtcgtgtt cgtcacccac tgcttcaaca accggcccaa ttattgttcc    360
ttgacgggac ttataccca gaactatatc cgaattgctg caatgaagag caacggcaca    420
ggcccaagcg atttattcta taatttgacc gttccagtca caaagtatcc aaagtttagg    480
agccttcaat gtgtgaataa ccagaccagt gtgtatctta acggtgacct cgtgttcacc    540
agcaacgaga ccgtggacat tagcggagca ggagtgcact tcgccgccgg tggcccaatt    600
acatacaagg tgatgcgcga ggtgaaggcc ctcgcctact tcgtcaatgg gacagcgcag    660
gatgtgatcc tctgtgacgg cacgcctcgg ggctcctgg catgtcagta caatactggt    720
aatttttagc acgggttcta cccattcacc aatagctcac tcgtcaagga gagattcata    780
gtgtataggg agaattctgt taacaccaca ctcgtcctgc acaatgttac gttcttcaac    840
gaaacttcag ccccgaacgg cggggacctt aatgcgaact ttcagatcta tcagaccgtg    900
actgcccagt ccggctacta caactttaac ttttctttct tatccgggtt cgtgtataaa    960
gaaagtgact ttatgtacgg ctcataccac cccaactgta acttccggcc cgagaatata    1020
aacaatggcc tctggttcaa ctccttatcc atcagcctgg catacggccc tttgcaaggt    1080
ggttgcaagc agagcgtgtt caataggaga gccacatgtt gctacgcgta ttcatataac    1140
ggccctcatg cctgtaaggg agtctaccga ggccagttaa ctcaactctt cgaatgcggt    1200
cttctggtgt acattaccaa gtctgacggg agccgcatcc agactgctac gaaggcgttg    1260
gttgtcacca ccaacttta caataacatc accctggata gatgcgtcga atacaatatc    1320
tacgggcgcg tagggcaggg atttattact aatgtcacag atagtacagc tgattacaat    1380
tatctggccg acggtgggtt ggccatcctg gatacttccg gggctattga tatcttcgtg    1440
gttcaggggg tatatggcct gaattttac aaggtcaatc cctgcgagga tgtgaaccag    1500
caattcgttg ttagcggagg caagttggtg ggcatactga cttcccggaa tgagaccgac    1560
agccaatttc tcgagaacca gttctatatc aagctcacac atgagaccca tggggcggga    1620
gtcccagtgt cagaaaacgt gaccagctgc ccctatgtct cttatggcaa gttttgcata    1680
aaacccgatg ggtccatctc tactattgtt cctgaggagc tcaaacaatt tgtgtcaccc    1740
ctcctcaacg tcaccgaata cgtgctgatt cctgattctt ttaatttaac tgtgacagac    1800
gagtatattc aaacacgtat ggataaggta cagatcaatt gtctgcagta cgtctgtggg    1860
aatagcttcg agtgtagaaa cctgttccag caatatgggc ccgtttgtga taacatactc    1920
tcagtggtca acagcgtggg gcagaaggaa gatatggagc tcctcacctt ttattcctct    1980
acaaaacccg ccggttataa cactcccgtg ttcaacaata tttccactgg agattttaat    2040
atttcactgc tcctcactcc ccctagcacg ccctcaggga ggtcctttat tgaagatctg    2100
cttttttacca gcgtggagag tgtgggcctc ccaactgatg aggcctacaa aaagtgcacc    2160
gcggggccgc tgggggtttct taaggacctg gcttgcgcta gagaatataa cgggctgctc    2220
gtgttgcccc ccattataac agctgagatg cagacactct acacatcctc tctggttgcg    2280
agcatggcc ttggcggggat aactgctgca ggtgcaatac ctttcgcgac gcagctccag    2340
gcccgtatta atcatttggg tatcactcaa actattcttc tcaaaaacca ggagaaaatt    2400
gcggcttcct tcaataaggc aatcggcaca atgcaagagg gatttaaatc tacgtctttg    2460
gcacttcagc agattcaaga cgtggtcaac aaacaatcag caattctcac tgagaccatg    2520
gccagtctga ataagaattt cggcgcgatc cggcgcgtga tccaggagat ataccagcag    2580
ctggactcca ttcaagccaa cgcacaagtt gaccgtatta tcaccggtcg cctcagttct    2640
ctgagcgtgc tggccagttc taaacaggct gagtacttgc gcgtgtcaca gcagaggag    2700
ctggcaaccc agaagataaa cgaatgcgtc aaatcacaga gcacacgcta ttccttttgc    2760
ggcaacggca ggcatgtgct gaccatcccc cagaatgcac ctaacggtat cgtctttata    2820
cattttacat acacccccga gtccttcgtg aatgttaccg ccatccgtgg gttttgcgtt    2880
aaccctgcta atgcgagcca atatgccatt gttccggcca acggccgggg cattttcatt    2940
caggtgaacg gcagttacta tatcactgcc agggatatgt atatgccacg ggatattaca    3000
gccggcgaca ttgttacatt aactagttgc caggccaact acgtctccgt gaataaaacc    3060
gtgatcacga ccctggtcga caatgacgac ttcgatttcc acgacgaact gagcaaatgg    3120
tggaacgaga ctaaacacga gctgcctgat ttcgaccagt ttaattacac aatccccgtg    3180
ttaaacatta catatgacat agacaagata gaggaggtaa taaagggttt aaacgactct    3240
ctcattgatc ttgaaactct gagcatcctg aagacttata tcaaatggcc aggctccgga    3300
tatatcccgg aagcaccacg agacgggcaa gcttatgtca gaaaagatgg tgagtgggtg    3360
ctgctgtcta ccttttctggg aaggtccctg gaagtgttgt ttcaagggcc aggccatcat    3420
catcaccatc accaccacag tgcttggtct caccctcagt ttgagaaggg cggtggcagc    3480
ggtggggggcg ggtccggggg gagtcgcatgg tcacacccgc aattcgagaa ataa    3534
```

SEQ ID NO: 5                moltype = DNA   length = 3543
FEATURE                     Location/Qualifiers
source                      1..3543

-continued

```
                         mol_type = other DNA
                         organism = Infectious Bronchitis Virus
SEQUENCE: 5
atgtcagtat tgttaccgct gttagtgacg ctgttatgcg cgctgtgttc cgccgttttg    60
tacgacatca acagttacgt ttattattac caaagtgcct ttcggccaag caacggctgg   120
cacctttacg ggggcgctta tgccgtagtt aatgtgagca atgagaacaa taatgcaggg   180
tctgcctcca cttgctactgc gggcgccata ggttactcaa agaattttc cgccgcctcc   240
attgccatga ctgctccacc tagtggaatg gcctggagca ctgccgcctt ttgcactgcc   300
cactgtaact ttacgaatat agtggtgttt gtcacccact gttacaaag cggcagcgga   360
agctgtcccc ttactggctt tatacagagc ggctatatcc gcattagcgc tatgaagaaa   420
gaatgctcag gtccctcctg tctgtttat aatctcaccg agagtgtgag caagtacccc   480
acattcagaa gccttcaatg cgtgaacaat tacacatccg tgtaccttaa tggtgacctt   540
gtgttcactt ccaactacac tcaggacgtc gtggctgctg gcgtacattt taaaagcgga   600
gggcccatta cctacaaggt gatgagggag gtcaaggcac tggcttattt cgtgaatggg   660
actgcccagg acgttatcct gtgtgacgat accccgaggg gactgctggc ttgccaatac   720
aacacgggga acttctccga cggctttat cctttcacca cacctcaat cgtcaaagac   780
aaatttattg tgtaccggga gtcaagcgtc aacacaaccc tgcactgac caattttaca   840
tttagtaacg agtccggagc accaccaaat accggaggtg tgaattcatt tatactctat   900
cagacgcaga cggcccaatc tggatactac aattttaact ttagcttcct gtctggtttc   960
gtgtacgaag agagcaacta tatgtatggc tcttaccatc ccctttgcag tttcaggcct  1020
gagaacatca ataatggtct gtggttcaat tccttatctg tctccatcac atatggacca  1080
ttgcaggggg ggtgtaagca aagctttttt caggggcggg caacgtgctg ctacgcctac  1140
tcatacaacg gtcctcgcgc atgtaaagga gtgtattccg gcgagctcac gcagtctttt  1200
gagtgcggct tacttgtgta catcactaag tctgacgggt ctcgaataca gacagccact  1260
aaagcaccag tggtgaccac taacttttat aataacataa ctctggacaa gtgcgtcgag  1320
tacaacattt acgggcgtgt gggacagggc ttcatcacaa atgtgaccga ttccgctttt  1380
ggctataatt atttacagga tggcggcctg gcgattctgg atacatcagg agccatcgat  1440
attttttgtgg tgaaaggcgt atacgggctt aactattata aggttaaccc ctgcgaggac  1500
gtgaatcaac aattcgtagt aagcggcggt actctggttg gggtcttgac aagtaggaac  1560
gaaacagggt cacagttttt agaaaaccag ttctatatca agcttacaaa tggtactcat  1620
ggtggtggcg tgccggtgaa cgaaaacgtg accagttgcc catacgtgag ttacggaaag  1680
ttctgtatta agcctgacgg cagtacctcc gttattgtcc caaaggagct cgagcaattc  1740
gttactcctc tgctcaacgc tactgagtat gtccccattc cggactcttt caacctcacg  1800
gtgaccgatg agtacatcca gacccgcatg gataaagttc agatcaattg cctgcagtat  1860
gtgtgcggga actctttcga atgtaggaat ctgtttcaac agtatggccc tgtgtgtgat  1920
aatattctta gcatcgtaaa cagcgtatcc cagaaagagg atatggagct tctcacattt  1980
tatagcagca ccaaaccgtt tggttttaac acgcctattc tctctaactt gtctaccggt  2040
gatttcaata tcagccttct gctgactcct ccatccagta ccactgggag gagctttatt  2100
gaggacctttt tgttcacttc cgtggagtct gtgggactcc ccacctgacga tgcctacaaa  2160
aaatgtactg ccgggcctct ggggttcctg aaagacctgg cctgcgcacg ggagtacaat  2220
gggctgctgg tcctgccacc tatcattacc gccgaaatgc agactatgta tacctcctct  2280
ctggtcgcca gtatggcact tggggggatc accgccgcag gagctattcc tttcgcaact  2340
cagctgcaag ccaggatcaa ccacctcggg attactcaag ccgtactgtt aaagaatcag  2400
gaaaagattg ctgcctcatt caataaggca attgggcaga tgcaggaagg ttttagatca  2460
acttcactgg ccttacagca gatccaggac gttgtgaaca aacaatccgc catactcact  2520
gagaccatgg catcactcaa caagaacttc ggagctatct caagtgtgat ccaggacatc  2580
taccagcagt tggacgtgat ccaagccgat gctcaggtgg accggctgat taccggtaga  2640
cttagcagtc tgagtgtgct cgcatcagct aagcaatcag aacacattat cgcctcccaa  2700
cagagagagt tggcaacaca aaaaatcaac gaatgtgtga aatctcagtc aacccggtac  2760
tcattttgtg ggaatggccg acatgtcctt accatcccac agaacgcccc aaacggtatt  2820
gtgttcatcc acttcactta cacccccgag tcattcgtga acgtaacagc catcgtcgga  2880
ttttgtgtta agccagcaaa cgcgagccag tacgccatcg tgcctgccaa cggtcgggc  2940
attttcattc agttcaatgg ctcttactac atcactgcaa gagacatgta catgcctagg  3000
aatatcactg caggcgacat cgtaactctt acctcatgcc agtctaacta cgtgtccgtg  3060
aataagactg tcatcaccac ctttgtggac aacgacgatt tcgacttcga cgatgaactg  3120
tcaaagtggt ggaatgacac taagcacgag ctgcctgact tcgatgagtt caactatacc  3180
gcccctattc tggatattga tagcgagata gatagaatac agggtgtcat ccagggcctg  3240
aatgactcct taatcgacct cgagacattg tcaatactga aaacatacat caaatggcca  3300
ggatcagggt acattccgga agctcctaga gacgggcagg catacgtgcg gaaggacgga  3360
gagtgggtgc tcctttctac ttttctgggc cgctccctgg aggtgctgtt tcaaggccgc  3420
ggtcatcatc accaccatca ccatcattct gcttggtctc accccagtt tgagaagggg  3480
ggcggcagtg gtggaggtgg ctccggtgga tccgcctggt cccatccaca attcgaaaag  3540
taa                                                                3543

SEQ ID NO: 6           moltype = DNA   length = 3513
FEATURE                Location/Qualifiers
source                 1..3513
                       mol_type = other DNA
                       organism = Infectious Bronchitis Virus
SEQUENCE: 6
atgctcgtga cacccttct cctggtgaca ctcctcttcg ctctgtgcag cgccgcgtta    60
tatgataatt cttcctatgt ctactattac cagagcgcat ttcggccccc gaatggttgg   120
catctgcacg gtggcgcata tgctgtagtg aacacctcca tcgagtccaa taacctcaga   180
gagtgcagac tgggcatcat cgggggcgat cgtgtgggtga acgcctctag cattgcaatg   240
accgccccac aaccagggat ggactggtcc tctcggcagt tctgtaccgc ccattgcaac   300
ttttccgata ttacggtatt cgtaactcac tgttataagc ataatgggtg ccccatcaca   360
ggcagtatcc cccaacactc cataagggtg tccgccatga gaaggggtcg actgttctat   420
aacctcaccg tgtcagtgaa taagtaccct acattcaaga gcttccagtg cgttaataac   480
tttactagcg tgtaccttaa tggagacctt gtttacacga gcaacgaaac caccgatgtg   540
```

```
acaagcgccg gggtgtactt caatgccggg ggacctatca cttacaaggt gatgagagag    600
gtgaaggcct tggcctattt tgttaacgga accgcccagg atgtgatctt gtgcgatgga    660
tccccccggg ggttgctgag ttgccaatat aatactggga atttttcaga cgggtttat     720
cccttcacca acagtagttt ggtgaagcag aaattcatag tgtacaggga gaattccatc    780
aatacaacac tgaagctcca caatttcacg ttccataagt aaacaggagc caacccaaac    840
ctgagcgggg tgcagaacat tcagacttac caaacacaga ctgctcagtc aggttactat    900
aactttaact tttccttcct gtccggcttt gtgtacaaag agtcaaattt tatgtacggt    960
agctaccacc caagttgcaa cttccgccct gagaccatta caatggcct ctggttcaac    1020
tctcttagtg tttccattgc ttatggtccc ttgcaaggag gctgtaagca gagcgtcttt    1080
tccggaagag ccacctgctg ttatgcttat agctacggag gcccttccct gtgcaaaggt    1140
gtgtatctgg gagaattaaa gagtgacttc gaatgcggcc tgcttgtgta cgtgactaaa    1200
agcgatggtt caaggattca aaccgccaca gagcccccgg tgatcactca gcataattac    1260
aataacatta ccctgaacac ttgcgttgat tacaacattt acgggaggac aggccaggga    1320
ttcatcacta atgtgaccga tagcgccgtc tcttacaact atctggcaga tgctggtatg    1380
gcaatcctgg atacatcagg aagcattgat atcttcgtgg tgcaaggcga atatggcctc    1440
acctattaca aagttaaccc atgtgaggac gtgaatcaac agtttgtggt gtctggtggc    1500
aagctcgtcg gtattttgac cagtcggaat gaaacaggct cccagcttct ggagaatcaa    1560
ttctatatta agattacaaa cggcacaggc ggcggagtcc catccattac tgctaatgta    1620
actaattgtc cttacgtgtc atatggaaag ttctgcatca agcctgatgg gagcgtgagc    1680
gccatcgtgc caaaagaact tgaacaattc gtcgcacctc tgctgaacgt gactgaaaac    1740
gtgctcatac ccaactcctt taacttaacc gtgactgatg aatacataca aaccagaatg    1800
gacaaaatcc aaattaactg tatgcagtac gtctgcggga atagccttga ttgtcgcaag    1860
ctgttccagc aatacgggcc agtatgcgac aatattctgt cagtggtgaa tagtgtcggc    1920
caaaaagagg acatggaact tctgaacttt tacagttcca caaagccctc aggatttaac    1980
acaccagtct tctccaatct gtctactggt gatttcaata tctctctgct ccttacacca    2040
ccttcctcta cgaccggaag gagttttatc gaggatctgc tgtttacaag tgtggagtct    2100
gtggggctcc ccacagatga agcttataaa aagtgcaccg caggtcccct gggtttcctg    2160
aaggacttgg cctgcgcccg agaatacaac ggcctccttg tcctcccccc aattatcaca    2220
gccgaaatgc agacactgta cacaagctct ctcgtagcgt ccatggcttt tggcggtata    2280
accgcagccg gagctattcc tttcgccact cagctgcaag ctcggattaa tcatctgggg    2340
atcacccaaa gcctccttca gaagaatcag gagaagattg ccgcgtcttt taacaaggcc    2400
atcgccgtgg tgcaggaagg atttcggtcc actagtttgg ccctgcagca gtccaggac     2460
gtcgtgaaca agcagagtgc aattttgact gagaccatgg ctagccttaa caagaacttt    2520
ggcgcgatta gttctgtaat tcaagacata taccagcagc tcgacgctat ccaagccaac    2580
gcccaggtgg atagactgat cactggaagg ctgtcatctt tatccgtact ggccagtgcg    2640
aaacaggctg aatacattcg ggtttcacag caaagagagc tcgccaccca gaaaattaat    2700
gaatgtgtca aaagccagtc tattagatat tctttttgtg gtaatgggag acacgtttta    2760
accatcccgc aaaacgcacc taatgggatt gtgttcattc actttaccta tacaccagag    2820
tctttcgtca atgttaccgc cattgtgggc ttctgcgtga aacctgccaa cgcatccaag    2880
tacgccatcg ttcctgcgaa cgggcgcggg attttcattc aggtgaacgg ttcttactac    2940
attacagccc gggatatgta tatgccacga gatatcacag ctggcgatat tgtgacgttg    3000
acctcatgcc aagccaacta tgtctcagtg aacaaaacag tcatcaccac attcgtggat    3060
aacgatgact ttgatttcga tgatgagctc tctaagtggt ggaatgatac caaacacgaa    3120
ttacccgact tcgatgaatt taattacacc gtgcccatac ttgatatcgg ctcagagatt    3180
gacaggatcc aggggggtaat ccaggggctg aatgactctc ttatcgactt ggagaccctg    3240
tccattttga aaacatacat aaaagtggcc cggatctggg atattccgga agcgcccagg    3300
gacggccagg cgtatgtgcg taaagacggc gaatgggtgc tgctttctac gttcctgggg    3360
agaagtctgg aggtgctgtt ccagggacct ggccatcacc accaccatca tcatcatagc    3420
gcttggagcc atcctcagtt tgaaaaaggc gggggaagtg gcggcggtgg ctctggtggt    3480
tccgcttggt cacatccaca gttcgagaag taa                                3513
```

```
SEQ ID NO: 7               moltype = DNA   length = 3513
FEATURE                    Location/Qualifiers
source                     1..3513
                           mol_type = other DNA
                           organism = Infectious Bronchitis Virus
SEQUENCE: 7
atgctcggga aatcactgtt tatcgtgaca ctgctgctcg ccctctgtga aggcggattg    60
gttggcgtca attatactta ctactatcag tccagatata ggccaccaaa cggatggcat    120
atgcagggcg gcgcatataa ggtagttaat aagaccacaa ttagttacac ctcacaagaa    180
tgtaccatcg gcgtaatccg gggtggcgta acgattaacc aatcagccat tgcctttaca    240
agcgccactg gcagagttgg cgttaagaag ggcgtttgta ccgtctattg taattatacc    300
tcattttatg tatttgtgac acactgcggt ggcacggggc ataactgcat cgtcaatacc    360
aagaagctcg gtgtgttggt gtttggtgtg aagaactata acgatcaatt tatctataat    420
attaccctga acgccgccgg accttatgcg aatttcaaag cttggcagtg cttgagtaat    480
tacacaagtg tgttcctcaa cggaaacttg ctctatacta gcaattatac tgaagatgtg    540
aaagctgctg agtgtacgc taagcaggtc aacggactgg aaagacgagt catgcgggat     600
accccagtta tggcatattt cgtcaacgga acggtgcagg acgttatcct gtgcgatgat    660
agcccaaagg gacggctcgc gtgtcagtat aataccgata actttagtga cgggctgtat    720
cctgtgtatg aggaaccggt agcatcaaat tttacctttg ttcctttgca tacttcaagc    780
acatcctacg gagttctgca caactttacc tttaataatg tgacgggagt cgcaccaaac    840
caagaacata ttgcccggtt caacatttca actatcagcg aggggtatgt gaacttcaag    900
ttcaatttc ttaattcctt cacttatgtc gagagcgact tcgatcgggg cagctactat    960
ggtaaaccgg gttcaagatg taatttttgg ttggagagta caatagagg gctgagttt     1020
aattccctca cggtttctat tggatacggg ccaatttctg cgggctgcaa acagagcgta    1080
tggaagaatg aggccacatg ctgtttcgct tataagtaca atggcggatc taggaactgt    1140
aagggacttt acactttcga tcgggatgtc aattatgaat gcgtttttgct cgtgttcata    1200
agcaaaccag atggctctcg cattaggaca gctacctcac ccctgtctca ttcaaacaat    1260
aacgtaaaca tcaatctggg gctgtgtgta gattataacg tctatggtat tacaggccgg    1320
```

```
ggcttgatca ccaacattac cgaatccgtc catcccggtt atctggatca tggtgggctg   1380
gtcttgctcg acgctactgg ctcaattgac accttcgtac tgcatagtga caagctcacc   1440
agctactaca aggtgaaccc atgtagcgat attaacgaac agtacgtcgt gtctggcggc   1500
aacttggtgg ggaaattgac ttctaataat caaactgtgg cccagcaact gggcgatatg   1560
ttttatgtca agttttcaac aagcggtggc ggcggcgtgc tggctacttc cgagaatgtt   1620
accagctgcc cctatgtgac gtacggcaaa ttctgcatca aaccagacg ggatataagt   1680
aatattgttc cggaagaggt caaagactat acctctttgc tcctgaatcg cacggactac   1740
gtgttgatcc ccaacagctt taatcttaca gtcacagatg aattcatcca aacccaattc   1800
cagaaaatcc agataaactg tatccaatat gtctgtgggt catcaattca atgcaaacaa   1860
ttgttccagc aatatgggag cgtgtgcggg aacatccttt ctattgtcaa cggcatagct   1920
cttcaagaca atgccgagat gctgcacttt tatagttcca ctaagccaag aggattcgac   1980
accaactcat tcgttaattt taccgccggc gagttcaata tctccttggt cctgccaaag   2040
aatggacaac ctacaggaag atgtttgatc gaagatttgt tgttcgacaa agtcgaatcc   2100
ctgggtctcc ctggggatag tgcttaccag aaatgtacat caggacctct cggatttgtg   2160
aaagatctcg tgtgtgcgca gaattacaat ggtctgttgg tattgccgcc aatcattacg   2220
gcggaaatgc aaacattgta tacttcttcc ctggttgtta gtatggcttt tggcggtatt   2280
acagctgcta gggctatccc tttcgccacc caaatccaag cgcgcatcaa ccatctggga   2340
atcactcaaa cagttttgca aaagaatcag gagaaaattg ccgcctcttt taataaggcc   2400
atgaagcata tgcaagatgg tttctccgca acaagcttgg cattgcaaca agttcaagat   2460
gttgtaaatg aacaaggagc catcttgcag caaaccatgc acagcctgaa taagaacttt   2520
ggcgccattt cccacgttat ccaagatatt tacaagcaac ttgacgccct ggaagcaaat   2580
gcgcaagttg accggatcat taccggccgc ttgagtagcc tttctgtcct tgcatccgcc   2640
aagcaactgg aatatacaaa ggtttctcaa cagcgagagc tcgcaaaaga aaagattaat   2700
gagtgtgtta aaagtcagtc aaacaggcac ggcttttgtg gtgaaggaat gcatatcatg   2760
tcaatccccc agaatgcgcc taatgggatc gtgtttctgc actttacgta tacacctgag   2820
acgtatgcta acgtgactgc agtcgtcggc ttttgtgtca aacccggtaa tgggaccgaa   2880
tatggcttgg ttccagtagt tgggcgaggt atatttattg aggtgaacgg cacttattac   2940
atcactggga gagatatgta tagccctagg gccatcaccg ctggggacgt cgttaaactc   3000
actccatgcc aagccaatta tcagtccatc aatagaacag tcatcaccac attcgtggat   3060
gaggatgact tcgatttcga tcatgagctc agtaagtggt ggaacgagac ttcacgtgat   3120
ttcccaaatc tcgatgagtt caactacacg atacctgtgt tgaatatcag caacgaaatc   3180
gacaagattc aagaggttat tcaaggcctt aatgatagca tcattgactt ggagaccctg   3240
agcatcctga aaacatacat caaatggcca ggatctggtt atattcctga agctccaagg   3300
gatggccaag cttacgtcag aaaggatggc gaatgggtcc ttttgtccac atttcttggg   3360
cgctctctcg aggttttgtt tcaaggcccc ggccatcatc atcaccatca tcatcattcc   3420
gcttggagcc accctcaatt tgaaaagggt ggtggctctg gtggcggcgg ctcaggcggt   3480
tcagcctggt cccatcccca atttgaaaag taa                                3513
```

SEQ ID NO: 8          moltype = DNA   length = 1257
FEATURE               Location/Qualifiers
source                1..1257
                      mol_type = other DNA
                      organism = Infectious Bronchitis Virus
SEQUENCE: 8
```
atggcaagcg gtaaagcaac tggaaagaca gacgccccag cgccagtcat caaactagga   60
ggaccaaagc cacctaaagt tggttcttct ggaaatgcat cttggtttca agcaataaaa   120
gccaagaagc taaattcaca tccacctaag tttgaaggta gcggtgttcc tgataatgaa   180
aatcttaaaa caagtcagca acatggatac tggaggcgcc aagccaggtt taagccagtt   240
aaaggcggaa gaaaaccagt cccagatgct tggtacttct attatactgg aacaggacca   300
gccgctgacc tgaattgggg tgatagccaa gatggtatag tgtgggttgc tgcaaagggt   360
gctgatgtta aatctagatc tcaccagggt acaaggggacc ctgacaagtt tgaccaatat   420
ccactacgat tctcggacgg aggacctgat ggtaatttcc gttgggactt cattcctctg   480
aatcgtggta ggagtggaag atcaacagca gcttcatcag cagcatctag tagagcaccg   540
tcgcgtgacg gctcgcgtgg tcgtagaagt ggttctgaag atgatcttat tgctcgtgca   600
gcaaagataa tccaggatca gcagaagaag ggttctcgca ttactaaggt taaggctgat   660
gaaatggctc accgccggta ttgcaagcgc actattccac ctggttataa ggttgatcaa   720
gtctttggcc cccgtactaa aggtaaggag ggaaattttg gtgatgacaa gatgaatgag   780
gaaggtatta aggatgggcg tgttacagca atgctcaacc tagtccctag cagccatgct   840
tgtctttttg gaagtagagt gacgcccaaa ctacaaccag atgggctgca cttgaaattt   900
gaatttacta ctgtggtccc acgtgatgat ccgcagtttg ataattatgt taaaatttgt   960
gatcagtgtg ttgatggtgt aggaacacgt ccaaaagatg atgaaccgag accaaagtca   1020
cgctcaagtt caagacctgc tacaagaaca agttctccgg cgccaagaca acaacgccca   1080
aagaaggaga aaaagccaaa gaagcaggat gatgaagtag ataaagcatt gacctcaaat   1140
gaggagagga acaatgcaca gctggaattt gatgaggaac caaggtgat taactggggg   1200
gatgcagctc taggagagaa tgaacttgga ggaggtcatc atcaccatca ccactaa      1257
```

SEQ ID NO: 9          moltype = DNA   length = 1257
FEATURE               Location/Qualifiers
source                1..1257
                      mol_type = other DNA
                      organism = Infectious Bronchitis Virus
SEQUENCE: 9
```
atggcaagcg gtaaggcaac tggaaagaca gatgccccag ctccagtcat caaactagga   60
ggaccaaagc cacctaaagt tggttcttct ggaaatgtat cttggtttca agcaataaaa   120
gccaagaagt taaattcacc tccgcctaag tttgaaggta gcggtgttcc tgataatgaa   180
aatctaaaac caagtcagca gcatggatat tggagacgcc aagctaggtt taagccaggt   240
aaaggtggaa gaaaaccagt cccagatgct tggtattttt actatactgg aacaggacca   300
gccgctaacc tgaattgggg tgatagccaa gatggtatag tgtgggttgc tggtaagggt   360
gctgatacta aatttagatc taatcagggt actcgtgact ctgacaagtt tgaccaatat   420
```

-continued

```
ccgctacggt tttcagacgg aggacctgat ggtaatttcc gttgggattt cattcctctg   480
aatcgtggca ggagtgggag atcaacagca gcttcatcag cagcatctag tagagcacca   540
tcacgtgaag tttcgcgtgg tcgcaggagt ggttctgaag atgatcttat tgctcgtgca   600
gcaaggataa ttcaggatca gcagaagaag ggttctcgca ttacaaaggc taaggctgat   660
gaaatggctc accgccggta ttgcaagcgc actattccac ctaattataa ggttgatcaa   720
gtgtttggtc cccgtactaa aggtaaggag ggaaattttg gtgatgacaa gatgaatgag   780
gaaggtatta aggatgggcg cgttacagca atgctcaacc tagttcctag cagccatgct   840
tgtctttttcg gaagtagagt gacgcccaga cttcaaccag atgggctgca cttgaaattt   900
gaatttacta ctgtggtccc acgtgatgat ccgcagtttg ataattatgt aaaaatttgt   960
gatcagtgtg ttgatggtgt aggaacacgt ccaacagatg atgaaccaag accaaagtca  1020
cgctcaagtt caagacctgc aacaagagga aattctccag cgccaagaca gcagcgccct  1080
aagaaggaga aaaagccaaa gaagcaggat gatgaagtgg ataaagcatt gacctcagat  1140
gaggagagga acaatgcaca gctggaattt gatgatgaac caaggtaat taactggggg  1200
gattcagccc taggagagaa tgaacttgga ggaggtcatc atcaccatca ccactaa    1257
```

SEQ ID NO: 10          moltype = AA   length = 412
FEATURE                Location/Qualifiers
source                 1..412
                       mol_type = protein
                       organism = Infectious Bronchitis Virus
SEQUENCE: 10
MASGKATGKT DAPAPVIKLG GPKPPKVGSS GNVSWFQAIK AKKLNSPPPK FEGSGVPDNE   60
NLKPSQQHGY WRRQARFKPG KGGRKPVPDA WYFYYTGTGP AANLNWGDSQ DGIVWVAGKG  120
ADTKFRSNQG TRDSDKFDQY PLRFSDGGPD GNFRWDFIPL NRGRSGRSTA ASSAASSRAP  180
SREVSRGRRS GSEDDLIARA ARIIQDQQKK GSRITKAKAD EMAHRRYCKR TIPPNYKVDQ  240
VFGPRTKGKE GNFGDDKMNE EGIKDGRVTA MLNLVPSSHA CLFGSRVTPR LQPDGLHLKF  300
EFTTVVPRDD PQFDNYVKIC DQCVDGVGTR PTDDEPRPKS RSSSRPATRG NSPAPRQQRP  360
KKEKKPKKQD DEVDKALTSD EERNNAQLEF DDEPKVINWG DSALGENELG GG          412

SEQ ID NO: 11          moltype = AA   length = 1165
FEATURE                Location/Qualifiers
source                 1..1165
                       mol_type = protein
                       organism = Infectious Bronchitis Virus
SEQUENCE: 11
MLVTPLLLVT LLCALCSAVL YDSSSYVYYY QSAFRPPNGW HLQGGAYAVV NISSEFNNAG   60
SSSGCTVGII HGGRVVNASS IAMTAPSSGM AWSSSQFCTA HCNFSDTTVF VTHCYKHGGC  120
PITGMLQQNL IRVSAMKNGQ LFYNLTVSVA KYPTFRSFQC VNNLTSVYLN GDLVYTSNET  180
IDVTSAGVYF KAGGPITYKV MREVKALAYF VNGTAQDVIL CDGSPRGLLA CQYNTGNFSD  240
GFYPFTNSSL VKQKFIVYRE NSVNTTCTLH NFIFHNETGA NPNPSGVQNI QTYQTKTAQS  300
GYYNFNFSFL SSFVYKESNF MYGSYHPSCN FRLETINNGL WFNSLSVSIA YGPLQGGCKQ  360
SVFKGRATCC YAYSYGGPSL CKGVYSGELD HNFECGLLVY VTKSGGSRIQ TATEPPVITQ  420
NNYNNITLNT CVDYNIYGRT GQGFITNVTD SAVSYNYLAD AGLAILDTSG SIDIFVVQGE  480
YGLNYYKVNP CEDVNQQFVV SGGKLVGILT SRNETGSQLL ENQFYIKITN GTGGGVPSIT  540
ENVANCPYVS YGKFCIKPDG SIATIVPKQL EQFVAPLFNV TENVLIPNSF NLTVTDEYIQ  600
TRMDKVQINC LQYVCGSSLD CRKLFQQYGP VCDNILSVVN SVGQKEDMEL LNFYSSTKPA  660
GFNTPVLSNV STGEFNISLL LTTPSSRRKR SLIEDLLFTS VESVGLPTND AYKNCTAGPL  720
GFFKDLACAR EYNGLLVLPP IITAEMQALY TSSLVASMAF GGITAAGAIP FATQLQARIN  780
HLGITQSLLL KNQEKIAASF NKAIGHMQEG FRSTSLALQQ IQDVVSKQSA ILTETMASLN  840
KNFGAISSVI QEIYQQFDAI QANAQVDRLI TGRLSSLSVL ASAKQAEYIR VSQQRELATQ  900
KINECVKSQS IRYSFCGNGR HVLTIPQNAP NGIVFIHFSY TPDSFVNVTA IVGFCVKPAN  960
ASQYAIVPAN GRGIFIQVNG SYYITARDMY MPRAITAGDV VTLTSCQANY VSVNKTVITT 1020
FVDNDDFDFN DELSKWWNDT KHELPDFDKF NYTVPILDID SEIDRIQGVI QGLNDSLIDL 1080
EKLSILKTYI KWPGSGYIPE APRDGQAYVR KDGEWVLLST FLGRSLEVLF QGPGSAWSHP 1140
QFEKGGGSGG GGSGGSAWSH PQFEK                                       1165

SEQ ID NO: 12          moltype = AA   length = 1172
FEATURE                Location/Qualifiers
source                 1..1172
                       mol_type = protein
                       organism = Infectious Bronchitis Virus
SEQUENCE: 12
MLVKSLFLVT ILFALCSANL YDNESFVYYY QSAFRPGHGW HLYGGAYAVV NVSSENNNAG   60
TAPSCTAGAI GYSKNLSAAS VAMTAPLSGM SWSANSFCTA HCNFTSYIVF VTHCYKSGSN  120
SCPLTGLIPS GYIRIAAMKH GSAMPGHLFY NLTVSVTKYP KFRSLQCVNN YTSVYLNGDL  180
VFTSNYTEDV VAAGVHFKSG GPITYKVMRE VKALAYFVNG TAHDVILCDD TPRGLLACQY  240
NTGNFSDGFY PFTNTSIVKD KFIVYRESSV NTTLTLTNFT FSNESGAPPN TGGVDSFILY  300
QTQTAQSGYY NFNFSFLSSF VYRESYYMYG SYHPRCSFRP ETLNNGLWFN SLSVSLTYGP  360
IQGGCKQSVF NGKATCCYAY SYGGPRACKG VYRGELTQHF ECGLLVYVTK SDGSRIQTAT  420
QPPVLTQNFY NNINLGKCVD YNIYGRIGQG LITNVTDLAV SYNYLSDAGL AILDTSGAID  480
IFVVQGEYGP NYYKVNPCED VNQQFVVSGG KLVGILTSRN ETGSQLLENQ FYIKITNGTG  540
GGVPSVTENV TNCPYVSYGK FCIKPDGSIS VIVPKELDQF VAPLLNVTEY VLIPNSFNLT  600
VTDEYIQTRM DKIQINCLQY VCGNSLACRK LFQQYGPVCD NILSVVNSVG QKEDMELLNF  660
YSSTKPARFN TPVFSNLSTG EFNISLLLTP PSSPRRRSFI EDLLFTSVES VGLPTDDAYK  720
MRTAGPLGFL KDLACAREYN GLLVLPPIIT AEMQTLYTSS LVASMAFGGI TAAGAIPFAT  780
QLQARINHLG ITQSLLLKNQ EKIAASFNKA IGHMQEGFRS TSLALQQIQD VVNKQSAILT  840
ETMLALNKNF GAISSVIQDI YQQLDSIQAD AQVDRLITGR LSSLSVLASA KQSEYIRVSQ  900
QRELATQKIN ECVKSQSIRY SFCGNGRHVL TIPQNAPNGI VFIHFTYTPE SFINVTAVVG  960
FCVSPANASQ YAIVPANGRG IFIQVNGSYY ITARDMYMPR DITAGDIVTL TSCQANYVSV 1020
```

```
NKTVITTFVD NDDFDFDDEL SKWWNETKHE LPDFDKFNYT VPILDIDSEI DRIQGVIQGL    1080
NDSLIDLETL SILKTYIKWP GSGYIPEAPR DGQAYVRKDG EWVLLSTFLG RSLEVLFQGP    1140
GSAWSHPQFE KGGGSGGGGS GGSAWSHPQF EK                                   1172

SEQ ID NO: 13           moltype = AA   length = 1175
FEATURE                 Location/Qualifiers
source                  1..1175
                        mol_type = protein
                        organism = Infectious Bronchitis Virus
SEQUENCE: 13
MLVKSPFIVT LLCALCSASL YDNGSYVYYY QSAFRPSIGW HLHGGAYAVV NVTQEYNNAG    60
SASECTAGAI VWSKNFSAAS VAMTAPHSGM SWSVKQFCTA HCNFTNFVVF VTHCFKDGLN    120
TCPLTGRIDQ GYIRIAAMKN TGTGPRDLFY NFTVSVTKYP SFKSLQCVNN QTSVYLNGDL    180
VFTSNETVDV SGAGVHFKAG GPITYKVMRE VKALAYFVNG TAQDVILCDS SPRGLLACQY    240
NTGNFSDGFY PFTNSSVVKE KFIVYSENSV NTTLVLHNFT FYNESDAPPN SQQSSAGVGG    300
LTTYQTQTAQ SGYYNFNFSF LSSFVYKESN FMYGSYHPQC NFRPENINNG LWFNSLSVSI    360
TYGPLQGGCK QSVFSHRATC CYAYSYNGPH ICKGVYSGQL HNNFECGLLV YITKTDGSRI    420
QTATTPPVRT QHFYNNITLH KCVEYNIYGR VGQGFITNVT DSVAGYNYLQ DGGLAILDTS    480
GAIDIFAVQG GYGLNFYKVN PCEDVNQQFV SGGNLVGIL TSRNETDSQP LENQFFVKLI    540
NGTGGGVPSI SENVTSCSFV SYGKFCIKPD GSISTIVPKE MEQFVAPLLN VTEHVLIPDS    600
FNLTVTDEYI QTRMDKVQIN CLQYVCGNSF ECRQLFQQYG PVCDNILSVV NSVGQKEDME    660
LLSFYSSTKP AGYNTPVFNI STGDFNISLL LPPSSAPSGR SFIEDLLFTS VESVGLPTDE    720
AYKKCTAGPL GFLKDLACAR EYNGLLVLPP IITAEMQTLY TSSLVASMAL GGITAAGAIP    780
FATQLQARIN HLGITQTVLL KNQEKIAASF NKAIGHMQEG FKSTSLALQQ IQDVVNKQSA    840
ILTETMASLN KNFGAISSVI QEIYQQLDAI QANAQVDRLI TGRLSSLSVL ASSKQAEYLR    900
VSQQRELATQ KINECVKSQS TRYSFCGNGR HVLTIPQNGV FIHFTY TPESFVNVTA        960
IVGFCINPAN ASQYAIVPAN GRGIFIQVNG TYYITARDMF MPRDITAGDV VTLTSCQANY    1020
VSVNKTVITT FVESDDFDFD DELSKWWNET KHEFPDFDQF NYTIPVLNIT YDIDKIEEVI    1080
KGLNDSLIDL ETLSILKTYI KWPGSGYIPE APRDGQAYVR KDGEWVLLST FLGRSLEVLF    1140
QGPGSAWSHP QFEKGGGSGG GGSGGSAWSH PQFEK                                1175

SEQ ID NO: 14           moltype = AA   length = 1169
FEATURE                 Location/Qualifiers
source                  1..1169
                        mol_type = protein
                        organism = Infectious Bronchitis Virus
SEQUENCE: 14
MLVKSLFTVI PLFALCSATL YDSGSYVYYY QSAFRPPNGW QLHGGAYAVV NVSTETGSAN    60
RCTAGAISFS KNFSAASVAM TAPANGMTWS DAQFCTAHCN FTNIVVFVTH CFKNRPNYCS    120
LTGLIPQNYI RIAAMKSNGT GPSDLFYNLT VPVTKYPKFR SLQCVNNQTS VYLNGDLVFT    180
SNETVDISGA GVHFAAGGPI TYKVMREVKA LAYFVNGTAQ DVILCDGTPR GLLACQYNTG    240
NFSDGFYPFT NSSLVKERFI VYRENSVNTT LVLHNVTFNN ETSAPNGGDL NANFQIYQTV    300
TAQSGYYNFN FSFLSGFVYK ESDFMYGSYH PNCNFRPENI NNGLWFNSLS ISLAYGPLQG    360
GCKQSVFNRR ATCCYAYSYN GPHACKGVYR GQLTQLFECG LLVYITKSDG SRIQTATKAL    420
VVTTNFYNNI TLDRCVEYNI YGRVGQGFIT NVTDSTADYN YLADGGLAIL DTSGAIDIFV    480
VQGVYGLNFY KVNPCEDVNQ QFVVSGGKLV GILTSRNETD SQFLENQFYI KLTNETHGGG    540
VPVSENVTSC PYVSYGKFCI KPDGSISTIV PEELKQYEVL NTEYVLI PDSFNLTVTD        600
EYIQTRMDKV QINCLQYVCG NSFECRNLFQ QYGPVCDNIL SVVNSVGQKE DMELLTFYSS    660
TKPAGYNTPV FNNISTGDFN ISLLLTPPST PSGRSFIEDL LFTSVESVGL PTDEAYKKCT    720
AGPLGFLKDL ACAREYNGLL VLPPIITAEM QTLYTSSLVA SMALGGITAA GAIPFATQLQ    780
ARINHLGITQ TILLKNQEKI AASFNKAIGH MQEGFKSTSL ALQQIQDVVN KQSAILTETM    840
ASLNKNFGAI SSVIQEIYQQ LDSIQANAQV DRIITGRLSS LSVLASSKQA EYLRVSQQRE    900
LATQKINECV KSQSTRYSFC GNGRHVLTIP QNAPNGIVFI HFTYTPESFV NVTAIVGFCV    960
NPANASQYAI VPANGRGIFI QVNGSYYITA RDMYMPRDIT AGDIVTLTSC QANYVSVNKT    1020
VITTLVDNDD FDFHDELSKW WNETKHELPD FDQFNYTIPV LNITYDIDKI EEVIKGLNDS    1080
LIDLETLSIL KTYIKWPGSG YIPEAPRDGQ AYVRKDGEWV LLSTFLGRSL EVLFQGPGSA    1140
WSHPQFEKGG GSGGGGSGGG AWSHPQFEK                                       1169

SEQ ID NO: 15           moltype = AA   length = 1172
FEATURE                 Location/Qualifiers
source                  1..1172
                        mol_type = protein
                        organism = Infectious Bronchitis Virus
SEQUENCE: 15
MSVLLPLLVT LLCALCSAVL YDINSYVYYY QSAFRPSNGW HLYGGAYAVV NVSNENNNAG    60
SASTCTAGAI GYSKNFSAAS IAMTAPPSGM AWSTAAFCTA HCNFTNIVVF VTHCYKSGSG    120
SCPLTGFIQS GYIRISAMKK ECSGPSCLFY NLTESVSKYP TFRSLQCVNN YTSVYLNGDL    180
VFTSNYTQDV VAAGVHFKSG GPITYKVMRE VKALAYFVNG TAQDVILCDD TPRGLLACQY    240
NTGNFSDGFY PFTNTSIVKD KFIVYRESSV NTTLTLTNFT FSNESGAPPN TGGVNSFILY    300
QTQTAQSGYY NFNFSFLSGF VYEESNYMYG SYHPLCSFRP ENINNGLWFN SLSVSITYGP    360
LQGGCKQSFF QGRATCCYAY SYNGPRACKG VYSGELTQSF ECGLLVYITK SDGSRIQTAT    420
KAPVVTTNFY NNITLDKCVE YNIYGRVGQG FITNVTDSAF GYNYLQDGGL AILDTSGAID    480
IFVKGVYGL NYYKVNPCED VNQQFVVSGG TLVGVLTSRN ETGSQFLENQ FYIKLTNGTH    540
GGGVPVNENV TSCPYVSYGK FCIKPDGSTS VIVPKELEQF VTPLLNATEY VPIPDSFNLT    600
VTDEYIQTRM DKVQINCLQY VCGNSFECRN LFQQYGPVCD NILSIVNSVS QKEDMELLTF    660
YSSTKPGFN TPILSNLSTG DFNISLLLTP PSSTTGRSFI EDLLFTSVES VGLPTDDAYK    720
KCTAGPLGFL KDLACAREYN GLLVLPPIIT AEMQTMYTSS LVASMALGGI TAAGAIPFAT    780
QLQARINHLG ITQAVLLKNQ EKIAASFNKA IGQMQEGFRS TSLALQQIQD VVNKQSAILT    840
ETMASLNKNF GAISSVIQDI YQQLDVIQAD AQVDRLITGR LSSLSVLASA KQSEHIIASQ    900
```

```
QRELATQKIN ECVKSQSTRY SFCGNGRHVL TIPQNAPNGI VFIHFTYTPE SFVNVTAIVG  960
FCVKPANASQ YAIVPANGRG IFIQFNGSYY ITARDMYMPR NITAGDIVTL TSCQSNYVSV  1020
NKTVITTFVD NDDFDFDDEL SKWWNDTKHE LPDFDEFNYT APILDIDSEI DRIQGVIQGL  1080
NDSLIDLETL SILKTYIKWP GSGYIPEAPR DGQAYVRKDG EWVLLSTFLG RSLEVLFQGP  1140
GSAWSHPQFE KGGGSGGGGS GGSAWSHPQF EK                               1172
```

```
SEQ ID NO: 16              moltype = AA  length = 1162
FEATURE                    Location/Qualifiers
source                     1..1162
                           mol_type = protein
                           organism = Infectious Bronchitis Virus
SEQUENCE: 16
MLVTPLLLVT LLFALCSAAL YDNSSYVYYY QSAFRPPNGW HLHGGAYAVV NTSIESNNLR  60
ECIVGIIGGD RVVNASSIAM TAPQPGMDWS SRQFCTAHCN FSDITVFVTH CYKHNGCPIT  120
GSIPQHSIRV SAMKKGRLFY NLTVSVNKYP TFKSFQCVNN FTSVYLNGDL VYTSNETTDV  180
TSAGVYFNAG GPITYKVMRE VKALAYFVNG TAQDVILCDG SPRGLLSCQY NTGNFSDGFY  240
PFTNSSLVKQ KFIVYRENSI NTTLKLHNFT FHNETGANPN LSGVNQIQTY QTQTAQSGYY  300
NFNFSFLSGF VYKESNFMYG SYHPSCNFRP ETINNGLWFN SLSVSIAYGP LQGGCKQSVF  360
SGRATCCYAY SYGGPSLCKG VYLGELKSDF ECGLLVYVTK SDGSRIQTAT EPPVITQHNY  420
NNITLNTCVD YNIYGRTGQG FITNVTDSAV SYNYLADAGM AILDTSGSID IFVVQGEYGL  480
TYYKVNPCED VNQQFVVSGG KLVGILTSRN ETGSQLLENQ FYIKITNGTG GGVPSITANV  540
TNCPYVSYGK FCIKPDGSVS AIVPKELEQF VAPLLNVTEN VLIPNSFNLT VTDEYIQTRM  600
DKIQINCMQY VCGNSLDCRK LFQQYGPVCD NILSVVNSVG QKEDMELLNF YSSTKPSGFN  660
TPVFSNLSTG DFNISLLLTP PSSTTGRSFI EDLLFTSVES VGLPTDEAYK KCTAGPLGFL  720
KDLACAREYN GLLVLPPIIT AEMQTLYTSS LVASMAFGGI TAAGAIPFAT QLQARINHLG  780
ITQSLLQKNQ EKIAASFNKA IAVVQEGFRS TSLALQQVQD VVNKQSAILT ETMASLNKNF  840
GAISSVIQDI YQQLDAIQAN AQVDRLITGR LSSLSVLASA KQAEYIRVSQ QRELATQKIN  900
ECVKSQSIRY SFCGNGRHVL TIPQNAPNGI VFIHFTYTPE SFVNVTAIVG FCVKPANASQ  960
YAIVPANGRG IFIQVNGSYY ITARDMYMPR DITAGDIVTL TSCQANYVSV NKTVITTFVD  1020
NDDFDFDDEL SKWWNDTKHE LPDFDEFNYT VPILDIGSEI DRIQGVIQGL NDSLIDLETL  1080
SILKTYIKWP GSGYIPEAPR DGQAYVRKDG EWVLLSTFLG RSLEVLFQGP GSAWSHPQFE  1140
KGGGSGGGGS GGSAWSHPQF EK                                          1162
```

```
SEQ ID NO: 17              moltype = AA  length = 1162
FEATURE                    Location/Qualifiers
source                     1..1162
                           mol_type = protein
                           organism = Infectious Bronchitis Virus
SEQUENCE: 17
MLGKSLFIVT LLLALCEGGL VGVNYTYYYQ SRYRPPNGWH MQGGAYKVVN KTTISYTSQE  60
CTIGVIRGGV TINQSAIAFT SATGRVGVKK GVCTVYCNYT SFYVFVTHCG GTGHNCIVNT  120
KKLGVLVFGV KNYNDQFIYN ITLNAAGPYA NFKAWQCLSN YTSVFLNGNL LYTSNYTEDV  180
KAAGVYAKQV NGLERRVMRD TPVMAYFVNG TVQDVILCDD SPKGRLACQY NTGNFSDGLY  240
PVYEEPVASN FTFVPLHTSS TSYGVLHNFT FNNVTGVAPN QEHIARFNIS TISEGYVNFK  300
FNFLNSFTYV ESDFDRGSYY GKPGSRCNFG LESINRGLSF NSLTVSIGYG PISGGCKQSV  360
WKNEATCCFA YKYNGGSRNC KGLYTFDRDV NYECVLLVFI SKPDGSRIRT ATSPPVYSNN  420
NVNINLGLCV DYNVYGITGR GLIITNITESV HPGYLDHGGL VLLDATGSID TFVLHSDKLT  480
SYYKVNPCSD INEQYVVSGG NLVGKLTSNN QTVAQQLGDM FYVKFSTGGG GGVPATSENV  540
TSCPYVTYGK FCIKPDGDIS NIVPEEVKDY TSLLLNRTDY VLIPNSFNLT VTDEFIQTQF  600
QKIQINCIQY VCGSSIQCKQ LFQQYGSVCG NILSIVNGIA LQDNAEMLHF YSSTKPRGFD  660
TNSFVNFTAG EFNISLVLPK NGQPTGRCLI EDLLFDKVES LGLPGDSAYQ KCTSGPLGFV  720
KDLVCAQNYN GLLVLPPIIT AEMQTLYTSS LVVSMAFGGI TAARAIPFAT QIQARINHLG  780
ITQTVLQKNQ EKIAASFNKA MKHMQDGFSA TSLALQQVQD VVNEQGAILQ QTMHSLNKNF  840
GAISHVIQDI YKQLDALEAN AQVDRIITGR LSSLSVLASA KQLEYTKVSQ QRELAKEKIN  900
ECVKSQSNRH GFCGEGMHIM SIPQNAPNGI VFLHFTYTPE SFVNTAVVG FCVKPGNGTR  960
YGLVPVVGRG IFIEVNGTYY ITGRDMYSPR AITAGDVVKL TPCQANYQSI NRTVITTFVD  1020
EDDFDFDHEL SKWWNETSRD FPNLDEFNYT IPVLNISNEI DKIQEVIQGL NDSIIDLETL  1080
SILKTYIKWP GSGYIPEAPR DGQAYVRKDG EWVLLSTFLG RSLEVLFQGP GSAWSHPQFE  1140
KGGGSGGGGS GGSAWSHPQF EK                                          1162
```

```
SEQ ID NO: 18              moltype = AA  length = 412
FEATURE                    Location/Qualifiers
source                     1..412
                           mol_type = protein
                           organism = Infectious Bronchitis Virus
SEQUENCE: 18
MASGKATGKT DAPAPVIKLG GPKPPKVGSS GNASWFQAIK AKKLNSHPPK FEGSGVPDNE  60
NLKTSQQHGY WRRQARFKPV KGGRKPVPDA WYFYYTGTGP AADLNWGDSQ DGIVWVAAKG  120
ADVKSRSHQG TRDPDKFDQY PLRFSDGGPD GNFRWDFIPL NRGRSGRSTA ASSAASSRAP  180
SRDGSRGRRS GSEDDLIARA AKIIQDQQKK GSRITKVKAD EMAHRRYCKR TIPPGYKVDQ  240
VFGPRTKGKE GNFGDDKMNE EGIKDGRVTA MLNLVPSSHA CLFGSRVTPK LQPDGLHLKF  300
EFTTVVPRDD PQFDNYVKIC DQCVDGVGTR PKDDEPRPKS RSSSRPATRT SSPAPRQQRP  360
KKEKKPKKQD DEVDKALTSN EERNNAQLEF DEEPKVINWG DAALGENELG GG          412
```

```
SEQ ID NO: 19              moltype = DNA  length = 22
FEATURE                    Location/Qualifiers
source                     1..22
                           mol_type = other DNA
                           organism = synthetic construct
```

```
SEQUENCE: 19
atgctcaacc tagtccctag ca                                            22

SEQ ID NO: 20          moltype = DNA  length = 21
FEATURE                Location/Qualifiers
source                 1..21
                       mol_type = other DNA
                       organism = synthetic construct
SEQUENCE: 20
tcaaactgcg gatcatcacg t                                             21

SEQ ID NO: 21          moltype = AA  length = 1169
FEATURE                Location/Qualifiers
source                 1..1169
                       mol_type = protein
                       organism = Infectious Bronchitis Virus
SEQUENCE: 21
MLVKSLFLVT ILFALCSANL YDNESFVYYY QSAFRPGHGW HLYGGAYAVV NVSSENNNAG   60
TAPSCTAGAI GYSKNLSAAS VAMTAPLSGM SWSANSFCTA HCNFTSYIVF VTHCYKSGSN  120
SCPLTGLIPS GYIRIAAMKH GSAMPGHLFY NLTVSVTKYP KFRSLQCVNN YTSVYLNGDL  180
VFTSNYTEDV VAAGVHFKSG GPITYKVMRE VKALAYFVNG TAHDVILCDD TPRGLLACQY  240
NTGNFSDGFY PFTNTSIVKD KFIVYRESSV NTTLTLTNFT FSNESGAPPN TGGVDSFILY  300
QTQTAQSGYY NFNFSFLSSF VYRESYYMYG SYHPRCSFRP ETLNNGLWFN SLSVSLTYGP  360
IQGGCKQSVF NGKATCCYAY SYGGPRACKG VYRGELTQHF ECGLLVYVTK SDGSRIQTAT  420
QPPVLTQNFY NNINLGKCVD YNIYGRIGQG LITNVTDLAV SYNYLSDAGL AILDTSGAID  480
IFVVQGEYGP NYYKVNPCED VNQQFVVSGG KLVGILTSRN ETGSQLLENQ FYIKITNGTR  540
RSRRSVTENV TNCPYVSYGK FCIKPDGSIS VIVPKELDQF VAPLLNVTEY VLIPNSFNLT  600
VTDEYIQTRM DKIQINCLQY VCGNSLACRK LFQQYGPVCD NILSVVNSVG QKEDMELLNF  660
YSSTKPARFN TPVFSNLSTG EFNISLLLTP PSSPRRRSFI EDLLFTSVES VGLPTDDAYK  720
MRTAGPLGFL KDLACAREYN GLLVLPPIIT AEMQTLYTSS LVASMAFGGI TAAGAIPFAT  780
QLQARINHLG ITQSLLLLKNQ EKIAASFNKA IGHMQEGFRS TSLALQQIQD VVNKQSAILT  840
ETMLALNKNF GAISSVIQDI YQQLDSIQAD AQVDRLITGR LSSLSVLASA KQSEYIRVSQ  900
QRELATQKIN ECVKSQSIRY SFCGNGRHVL TIPQNAPNGI VFIHFTYTPE SFINVTAVVG  960
FCVSPANASQ YAIVPANGRG IFIQVNGSYY ITARDMYMPR DITAGDIVTL TSCQANYVSV  1020
NKTVITTFVD NDDFDFDDEL SKWWNETKHE LPDFDKFNYT VPILDIDSEI DRIQGVIQGL  1080
NDSLIDLETL SILKTYIKWP WYVWLAIAFA TIIFILILGW LFFMTGCCGC CCGCFGIIPL  1140
MSKCGKKSSY YTTFDNDVVT EQYRPKKSV                                    1169

SEQ ID NO: 22          moltype = AA  length = 3510
FEATURE                Location/Qualifiers
source                 1..3510
                       mol_type = protein
                       organism = Infectious Bronchitis Virus
SEQUENCE: 22
ATGCTTGTAA AATCCCTGTT TTTGGTGACT ATCCTTTTTG CACTGTGCTC CGCTAATCTT   60
TACGACAACG AGTCCTTTGT CTACTACTAC CAGTCCGCCT TCAGGCCAGG CCATGGATGG  120
CACCTCTACG GAGGCGCCTA TGCAGTGGTA AATGTGTCTA GTGAAAACAA TAACGCCGGG  180
ACCGCGCCGT CCTGCACAGC AGGGGCCATT GGCTATTCCA AAAACCTCAG TGCTGCCTCC  240
GTAGCCATGA CAGCTCCCCT CTCTGGGATG TCCTGGAGTG CCAATTCATT CTGCACCGCT  300
CATTGCAATT TCACATCATA TATTGTGTTT GTTACGCACT GCTACAAGAG CGGCTCTAAC  360
AGTTGCCCCC TCACAGGGTT GATACCTTCT GGATATATCC GAATTGCAGC AATGAAGCAC  420
GGTAGTGCTA TGCCTGGACA TCTTTTTTAC AATCTGACTG TGAGCGTGAC CAAGTATCCA  480
AAATTCCGTT CCCTGCAGTG TGTGAACAAC TACACTTCTG TTTACTTGAA CGGAGACCTA  540
GTCTTCACTA GCAATTATAC CGAAGATGTG GTCGCTGCTG GGGTGCACTT CAAATCAGGG  600
GGCCCAATTA CGTACAAGGT GATGAGAGAA GTGAAGGCAC TAGCCTATTT CGTAAACGGT  660
ACTGCACACG ATGTCATCCT ATGTGACGAC ACACCTCGCG GATTGTTAGC CTGCCAGTAT  720
AACACAGGAA ACTTCTCAGA TGGTTTTTAT CCATTTACGA ACACCTCCAT TGTGAAGGAC  780
AAATTTATTG TTTACCGGGA GAGTTCTGTC AACACAACAC TAACACTCAC AAATTTTACA  840
TTCTCTAATG AATCAGGAGC GCCACCAAAT ACGGGTGGAG TGGATTCTTT CATACTCTAT  900
CAGACACAAA CCGCTCAATC AGGGTATTAC AACTTTAATT TCAGCTTTCT CAGTTCATTT  960
GTTTACAGGG AGTCTTACTA CATGTATGGC TCCTACCACC CACGCTGCAG TTTCAGACCT  1020
GAGACATTGA ACAACGGCCT GTGGTTCAAC TCGCTATCGG TATCCCTAAC CTATGGGCCG  1080
ATTCAGGGCG GCTGCAAACA GTCTGTCTTC AACGGAAAAG CTACCTGCTG CTATGCTTAC  1140
TCGTATGGAG GGCCCAGAGC TTGCAAGGGA GTGTATCGAG GAGAACTCAC ACAGCACTTT  1200
GAGTGCGGCC TGTTGGTTTA CGTCACTAAA TCCGACGGCA GTAGGATTCA GACAGCAACA  1260
CAGCCACCAG TGTTAACCCA GAACTTTTAT AATAATATAA ACCTAGGGAA ATGTGTTGAC  1320
TACAACATTT ATGGAAGAAT CGGGCAGGGG CTGATCACCA ATGTCACAGA TCTTGCTGTT  1380
TCTTATAATT ACCTTTCAGA TGCTGGTCTG GCAATCCTAG ACACCAGTGG CGCTATCGAC  1440
ATCTTTGTCG TGCAAGGAGA GTATGGTCCC AATTATTACA AAGTGAACCC CTGTGAGGAC  1500
GTGAACCAGC AGTTTGTTGT TAGCGGGGGC AAGCTTGTTG GCATACTCAC CAGCAGAAAT  1560
GAAACTGGAT CCCAGTTACT TGAAAATCAG TTCTACATCA AAATCACTAA CGGTACACGA  1620
AGGAGCCGAA GGTCAGTCAC GGAGAACGTT ACTAACTGTC CTTATGTCAG TTACGGTAAG  1680
TTCTGCATTA AGCCAGATGG AAGCATTAGC GTGATCGTCC CCAAGGAACT GGATCAGTTT  1740
GTAGCTCCAT TGCTTAATGT TACAGAATAT GTGCTTATTC CAAACTCCTT CAACCTGACT  1800
GTGACTGATG AATACATTCA GACCAGGATG GACAAGATAC AAATAAACTG CCTGCAATAT  1860
GTTTGTGGGA ATAGTCTAGC ATGCAGGAAA CTGTTTCAGC AGTATGGCCC CGTGTGTGAT  1920
AATATCCTTA GTGTCGTTAA TAGTGTTGGA CAGAAGGAGG ATATGGAGCT GCTCAATTTC  1980
TACAGCAGTA CTAAACCAGC CCGGTTCAAT ACTCCTGTGT TTCCAACCT CTCTACAGGA  2040
GAATTTAATA TCTCTCTGCT GTTAACCCCG CCCTCCAGCC CTCGGCGGCG GTCATTTATC  2100
```

-continued

```
GAAGACCTCC TTTTCACCTC AGTGGAGTCA GTAGGTCTGC CCACGGATGA TGCATACAAG  2160
ATGAGAACCG CGGGGCCTCT GGGCTTCTTG AAAGATCTCG CGTGTGCTAG AGAGTACAAT  2220
GGTCTGCTGG TGTTGCCTCC GATTATTACC GCTGAGATGC AGACTCTGTA CACTAGCTCA  2280
CTGGTGGCAT CAATGGCGTT CGGAGGAATA ACCGCCGCCG GAGCAATTCC CTTCGCCACA  2340
CAACTGCAGG CCAGAATCAA CCATCTGGGG ATCACTCAGA GCTTATTGCT GAAGAACCAG  2400
GAGAAGATCG CTGCATCGTT CAACAAAGCG ATAGGCCACA TGCAGGAAGG TTTTCCGCTCC  2460
ACCTCTTTGG CTTTGCAACA GATACAGGAC GTAGTCAATA AGCAGTCTGC AATCTTGACG  2520
GAAACCATGC TGGCTCTGAA CAAAAATTTT GGAGCCATAT CTAGTGTGAT TCAAGATATT  2580
TACCAGCAGC TGGACAGCAT CCAGGCAGAT GCACAAGTCG ATCGTCTGAT TACCGGTCGG  2640
TTAAGCAGCC TATCTGTTTT GGCCAGCGCA AACAATCTG AATATATCCG GGTCTCCCAA  2700
CAGAGAGAAT TAGCAACGCA AAAAATAAAT GAATGTGTCA AGAGTCAATC CATCCGCTAC  2760
TCGTTCTGTG GGAACGGCAG GCATGTGCTG ACTATCCCCC AGAATGCTCC TAACGGTATC  2820
GTATTTATAC ATTTCACATA TACACCAGAA TCTTTTATTA ATGTGACGGC GGTAGTCGGT  2880
TTTTGTGTGT CACCTGCCAA TGCATCTCAG TACGCTATAG TGCCCGCAAA TGGGAGAGGG  2940
ATTTTCATTC AGGTGAACGG AAGCTATTAC ATCACGGCCC GCGACATGTA CATGCCTCGT  3000
GACATCACAG CTGGCGACAT AGTAACACTT ACTAGCTGTC AAGCGAACTA CGTGAGTGTC  3060
AATAAAACTG TTATCACGAC CTTCGTGGAC AATGATGATT TTGACTTCGA CGATGAGCTT  3120
TCTAAATGGT GGAATGAGAC TAAGCATGAG CTGCCCGACT TTGATAAGTT TAACTACACA  3180
GTACCCATTC TCGATATTGA TAGTGAGATC GATCGTATTC AGGGTGTTAT CCAAGGACTT  3240
AACGACAGCC TGATAGACCT GGAGACGCTG AGCATTCTGA AGACATACAT AAAGTGGCCA  3300
TGGTACGTCT GGCTGGCCAT TGCCTTTGCG ACAATAATTT TTATTTTGAT TCTGGGCTGG  3360
CTCTTCTTCA TGACTGGTTG CTGTGGCTGT TGTTGCGGGT GCTTCGGTAT CATCCCTCTG  3420
ATGAGCAAGT GTGGCAAAAA GTCAAGCTAT TATACTACCT TTGATAACGA TGTGGTAACA  3480
GAGCAGTACC GCCCGAAAAA GTCCGTGTGA                                   3510
```

SEQ ID NO: 23                moltype = AA   length = 1172
FEATURE                      Location/Qualifiers
source                       1..1172
                             mol_type = protein
                             organism = Infectious Bronchitis Virus
SEQUENCE: 23

```
MLVKSPFIVT LLCALCSASL YDNGSYVYYY QSAFRPSIGW HLHGGAYAVV NVTQEYNNAG   60
SASECTAGAI VWSKNFSAAS VAMTAPHSGM SWSVKQFCTA HCNFTNFVVF VTHCFKDGLN  120
TCPLTGRIDQ GYIRIAAMKN TGTGPRDLFY NFTVSVTKYP SFKSLQCVNN QTSVYLNGDL  180
VFTSNETVDV SGAGVHFKAG GPITYKVMRE VKALAYFVNG TAQDVILCDS SPRGLLACQY  240
NTGNFSDGFY PFTNSSVVKE KFIVYSENSV NTTLVLHNFT FYNESDAPPN SQQSSAGVGG  300
LTTYQTQTAQ SGYYNFNFSF LSSFVYKESN FMGSYHPQC NFRPENINNG LWFNSLSVSI  360
TYGPLQGGCK QSVFSHRATC CYAYSYNGPH ICKGVYSGQL HNNFECGLLV YITKTDGSRI  420
QTATTPPVRT QHFYNNITLH KCVEYNIYGR VGQGFITNVT DSVAGYNYLQ DGGLAILDTS  480
GAIDIFAVQG GYGLNFYKVN PCEDVNQQFV VSGGNLVGIL TSRNETDSQP LENQFFVKLI  540
NGTRRSRRSI SENVTSCSFV SYGKFCIKPD GSISTIVPKE MEQFVAPLLN VTEHVLIPDS  600
FNLTVTDEYI QTRMDKVQIN CLQYVCGNSF ECRQLFQQYG PVCDNILSVV NSVGQKEDME  660
LLSFYSSTKP AGYNTPVFNI STGDFNISLL LPPSSAPSGR SFIEDLLFTS VESVGLPTDE  720
AYKKCTAGPL GFLKDLACAR EYNGLLVLPP IITAEMQTLY TSSLVASMAL GGITAAGAIP  780
FATQLQARIN HLGITQTVLL KNQEKIAASF NKAIGHMQEG FKSTSLALQQ IQDVVNKQSA  840
ILTETMASLN KNFGAISSVI QEIYQQLDAI QANAQVDRLI TGRLSSLSVL ASSKQAEYLR  900
VSQQRELATQ KINECVKSQS TRYSFCGNGR HVLTIPQNGN NGIVFIHFTY TPESFVNVTA  960
IVGFCINPAN ASQYAIVPAN GRGIFIQVNG TYYITARDMF MPRDITAGDV VTLTSCQANY  1020
VSVNKTVITT FVESDDFDFD DELSKWWNET KHEFPDFDQF NYTIPVLNIT YDIDKIEEVI  1080
KGLNDSLIDL ETLSILKTYI KWPWYVWLAI FFAIIIFILV LGWIFFMTGC CGCCCGCFGI  1140
IPLMSKCGKK SSYYTTFDND VVTEQYRPKK SV                                1172
```

SEQ ID NO: 24                moltype = DNA   length = 3519
FEATURE                      Location/Qualifiers
source                       1..3519
                             mol_type = other DNA
                             organism = Infectious Bronchitis Virus
SEQUENCE: 24

```
atgctggtca agtcaccgtt catagttacg ctgttatgtg ctctgtgttc tgcctcatta   60
tatgacaacg gcagctacgt atattactac cagtctgcgt ttcgccctag tattgggtgg  120
cacctccatg gcggagcata cgccgtggtt aatgtcactc aggaatataa caacgctggc  180
agtgctagtg aatgcacggc aggcgcgatc gtttggagca agaactttag cgctgctagt  240
gttgctatga cggcacctca ctctggcatg agctggtctg taaagcagtt ctgcacggct  300
cactgcaact tcaccaattt tgttgtgttt gtgacacatt gcttcaagga tggccttaac  360
acctgccctt tgacgggtcg gattgaccaa gggtatatcc gcattgccgc catgaagaac  420
acagggacag gaccccggga cctattttac aactttaccg tatctgttac caaatatcca  480
tcgttcaaat cattgcagtg cgtgaacaac cagacttccg tgtacctaaa tggtgaccta  540
gttttcacct ctaatgaaac tgtggacgtt agcggagctg gagtgcactt taaggctggt  600
gggccgataa catataaagt gatgagagaa gtgaaagcgc ttgcatactt cgtaaacggt  660
acagcccagg atgtgattct ctgtgattcc tcgccgcggg ggctgctcgc ttgtcagtac  720
aataccggaa actttagtga tggcttctac ccattcacaa attcatcagt cgtaaaggaa  780
aagttcattg tctactctga aaacagtgtg aatacaacat tggtcctcca caatttcact  840
ttttataatg aatcagatgc tccacccaac tcacagcagt cttcagcagg ggtgggtggg  900
ctcaccacct accaaacaca gaccgcccaa tcagggtact acaacttcaa tttctctttc  960
ctttcttcct tcgtatacaa ggagtcaaac ttcatgtatg gtagctatca ccctcagtgt  1020
aatttccgcc ctgagaacat caacaacggt ctgtggttta cagcctgag cgtgagcatt  1080
acctacggcc ccttacaagg ggggtgcaaa cagtccgtct tcagccatag agccacgtgt  1140
tgttacgctt actcctacaa cgggccccac atctgcaagg gagtttacag cggccagctg  1200
cataacaatt ttgaatgtgg cctactggtg tatattacta aaacagatgg atccaggatc  1260
```

-continued

```
caaaccgcaa ctactccacc cgtgcgcact cagcacttct ataataacat aactctgcac   1320
aaatgcgtcg aatacaacat ttatggaaga gtcggacaag gtttcatcac aaacgtcact   1380
gacagcgtag cgggctacaa ctaccttcag gatggcggtt tagcaatcct tgacacatct   1440
ggtgccattg atattttgc tgtccaggga ggctatggat tgaattttta taggtcaac    1500
ccctgtgaag atgtgaacca gcaatttgta gttagtggag ggaatctcgt aggaatctta   1560
acgtcacgca atgagacgga cagtcagccg ctcgagaatc agttcttcgt caagctgata   1620
aatggtaccc gccgttctag gagaagcatc agcgaaatg tgacatcatg cagctttgtg   1680
tcctatggca agttttgcat caagcctgac gggtctatct ctactatcgt acccaaagag   1740
atggaacagt ttgttgcccc gctcttgaat gtcaccgaac atgtcctgat tccagatagc   1800
ttcaatctga cagtgactga tgagtacatt cagaccgaac tggataaggt gcagatcaac   1860
tgcttgcaat atgtgtgcgg gaactccttt gagtgtaggc agctcttcca gcaaatacggg   1920
ccagtctgtg acaatatcct ctctgtagtt aactccgtcg gacagaagga ggacatggag   1980
cttctcagct tttacagctc cacgaagcca gccggttata acactcccgt cttcaatatt   2040
tctacaggag actttaatat ctccctgctg ctccctccat cctccgcacc ctcaggtaga   2100
tcatttattg aggatctgct gtttaccagt gttgagtctg tgggcttgcc aactgatgaa   2160
gcctacaaaa agtgtaccgc tggcccactg ggattcctga aagatttggc ctgcgcgaga   2220
gagtataacg gactgctcgt tttacccccc attattaccg ctgaaatgca gacactgtac   2280
acgagctctt tggtggcctc catggcactg ggaggcatca ctgcggcggg tgcaatcccg   2340
tttgctacac aactgcaggc caggataaac cacctgggca taacacaaac agtgctgttg   2400
aaaaaccaag agaagattgc cgcatctttc aacaaagcta taggacacat gcaggaggga   2460
tttaagagta cttcacttgc tttacagcaa atacaggacg tggtgaataa acaatcagcc   2520
atattaactg agacaatggc ctcccttaac aaaaattttg gcgccattag ttccgttatc   2580
caagaaatat atcaacaact ggacgcaatt caagcaaatg cacaggtgga tcgtctaatc   2640
actgacggc taagctcgct gtccgtactg gcgtcgagca aacaggcaga gtatttgcga   2700
gtaagccagc agcgggagtt ggcaacccag aaaaataaacg agtgtgtgaa aagccagtct   2760
acgcgatatt cgttctgtgg taatggtagg catgtgctga ctatccctca gaatgcccct   2820
aacggcattg tgttcatcca tttcacttac acacctgaaa gttttgtgaa cgtaacagct   2880
attgtgggat tctgcattaa tccagcaaac gcttcgcagt acgcaattgt tcccgctaat   2940
ggccgtggaa tattcatcca ggtcaatgga acctactata taacagccag ggatatgttc   3000
atgcctaggg acatcacagc aggcgatgtt gtgacgctga ccagctgcca ggcaaactat   3060
gttagtgtca ataagacagt cattacaacc ttcgttgaat cagacgattt tgactttgat   3120
gacgagcttt caaaatggtg gaatgaaaca aaacatgaat ttccagattt tgatcagttc   3180
aattacacca tccccgttct aaatatcacg tatgatatag acaaaatcga ggaggtgatc   3240
aaagggctta atgactcgct catcgatctg gagactctaa gtattctgaa aacctacatt   3300
aagtggccct ggtacgtgtg gctggccata tttttgcaa tcataatctt catccttgtt   3360
ttaggctgga tcttctttat gaccggatgc tgtggctgtt gctgtgggtg ctttgggatt   3420
atccctctca tgtctaagtg cgggaagaaa tcttcctatt atacaacttt tgacaatgat   3480
gtggtgacag agcagtatcg acctaagaag agtgtttga                         3519
```

SEQ ID NO: 25          moltype = AA   length = 1166
FEATURE                Location/Qualifiers
source                 1..1166
                       mol_type = protein
                       organism = Infectious Bronchitis Virus
SEQUENCE: 25

```
MLVKSLFTVI PLFALCSATL YDSGSYVYYY QSAFRPPNGW QLHGGAYAVV NVSTETGSAN   60
RCTAGAISFS KNFSAASVAM TAPANGMTWS DAQFCTAHCN FTNIVVFVTH CFKNRPNYCS   120
LTGLIPQNYI RIAAMKSNGT GPSDLFYNLT VPVTKYPKFR SLQCVNNQTS VYLNGDLVFT   180
SNETVDISGA GVHFAAGGPI TYKVMREVKA LAYFVNGTAQ DVILCDGTPR GLLACQYNTG   240
NFSDGFYPFT NSSLVKERFI VYRENSVNTT LVLHNVTFFN ETSAPNGGDL NANFQIYQTV   300
TAQSGYYNFN FSFLSGFVYK ESDFMYGSYH PNCNFRPENI NNGLWFNSLS ISLAYGPLQG   360
GCKQSVFNRR ATCCYAYSYN GPHACKGVYR GQLTQLFECG LLVYITKSDG SRIQTATKAL   420
VVTTNFYNNI TLDRCVEYNI YGRVGQGFIT NVTDSTADYN YLADGGLAIL DTSGAIDIFV   480
VQGVYGLNFY KVNPCEDVNQ QFVVSGGKLV GILTSRNETD SQFLENQFYI KLTNETHRSR   540
RSVSENVTSC PYVSYGKFCI KPDGSISTIV PEELKQFVSI LLNVTEYVLI PDSFNLTVTD   600
EYIQTRMDKV QINCLQYVCG NSFECRNLFQ QYGPVCDNIL SVVNSVGQKE DMELLTFYSS   660
TKPAGYNTPV FNNISTGDFN ISLLLTPPST PSGRSFIEDL LFTSVESVGL PTDEAYKKCT   720
AGPLGFLKDL ACAREYNGLL VLPPIITAEM QTLYTSSLVA SMALGGITAA GAIPFATQLQ   780
ARINHLGITQ TILLKNQEKI AASFNKAIGH MQEGFKSTSL ALQQIQDVVN KQSAILTETM   840
ASLNKNFGAI SSVIQEIYQQ LDSIQANAQV DRIITGRLSS LSVLASSKQA EYLRVSQQRE   900
LATQKINECV KSQSTRYSFC GNGRHVLTIP QNAPNGIVFI HFTYTPESFV NVTAIVGFCV   960
NPANASQYAI VPANGRGIFI QVNGSYYITA RDMYMPRDIT AGDIVTLTSC QANYVSVNKT   1020
VITTLVDNDD FDFHDELSKW WNETKHELPD FDQFNYTIPV LNITYDIDKI EEVIKGLNDS   1080
LIDLETLSIL KTYIKWPWYV WLAIFFAIII FILILGWVFF MTGCCGCCCG CFGIIPLMSK   1140
CGKKSSYYTT FDNDVVTEQY RPKKSV                                       1166
```

SEQ ID NO: 26          moltype = DNA   length = 3501
FEATURE                Location/Qualifiers
source                 1..3501
                       mol_type = other DNA
                       organism = Infectious Bronchitis Virus
SEQUENCE: 26

```
atgctggtga agagcttgtt tacagtcatt cctctgtttg ctctgtgctc cgctactctg   60
tatgacagcg gtagttatgt ctattactac cagtcagcat tccgcccacc taatggttgg   120
cagctgcatg gaggcgccta tgcagtggtg aatgtctcaa ccgagacagg ttccgccaac   180
aggtgtactg cgggagccat aagtttcagc aaaaattttt ccgccgcgag cgtagctatg   240
accgctccag cgaacggtat gacgtggtca gatgcacagt tttgcacagc ccattgcaat   300
ttcactaata ttgtggtctt cgtgacacac tgcttcaaga cagacccaa ctactgtagc    360
ctcacggggc tcataccaca gaactatatc agaatagccg ccatgaaatc gaatgggacc   420
```

-continued

```
ggtccttccg acctctttta caacctcact gtgccggtta cgaaataccc caagttcagg   480
tctcttcagt gtgttaacaa ccagacttca gtatacctga atggtgattt agtatttact   540
tccaacgaaa cagtggatat ttctggggcc ggggttcact tcgcagccgg tggtcccatt   600
acgtacaagg tgatgagaga agttaaggct cttgcatatt ttgtcaatgg cacagcgcag   660
gacgtgattt tatgtgatgg aactccaaga gggctcttgg catgtcagta taacactggt   720
aacttttccg atgggttcta tccatttacc aacagcagcc tggtgaagga gaggtttatt   780
gtatatcggg agaactcagt caacaccacg cttgttctgc acaacgttac attctttaat   840
gaaacatcag cacctaatgg aggagatctc aatgccaatt ttcagatcta tcagaccgtg   900
acagcgcaaa gtggatatta taacttcaac ttttctttcc tgtctggatt cgtttataaa   960
gaaagcgatt ttatgtatgg atcctaccat ccaaactgca acttccgccc tgaaaatatt  1020
aataatgggc tgtggtttaa cagtctgagc atcagcctgg cttatggtcc cctgcaaggc  1080
ggttgcaagc aaagtgtctt taaccgaaga gcaacctgtt gctacgctta cagctacaac  1140
ggccctcatg cctgcaaagg ggtgtaccgg ggccagctca ctcagctatt tgaatgcggc  1200
ttgctcgtat acatcaccaa aagtgatggt agccgcattc gacggctac aaaagcactg  1260
gtcgttacaa caaacttcta taataacatc actctcgatc ggtgcgttga gtacaacatt  1320
tatgcccggg tgggacaagg cttcatcaca aatgtgacag actcaacagc agactacaat  1380
taccttgctg acggcgggct ggcgatactg gacacgtccg gggcaattga tatttttgtg  1440
gtgcaggggg tctacggatt gaacttctac aaggttaacc cctgtgaaga tgtgaaccaa  1500
cagtttgttg tttccggtgg caagctggtg gggattttga catcgaggaa cgagacagac  1560
agccagttcc tagagaatca attctatata aagcttacta atgaaaccca ccgtagcagg  1620
agatctgtga gcgaaaacgt aacatcttgt ccctatgtca gctatggtaa attctgcatc  1680
aagccagatg gatcaataag taccattgtt ccagaagatt gaagcagtt cgttagcccg  1740
ttgttaaatg tgacagagta gtgtgctcatt cctgatagtt tcaatctgac tgttacggat  1800
gagtatattc aaactcgcat ggacaaggtc cagataaact gcctgcagta tgtctgcgga  1860
aattcttttg agtgccgtaa cctcttccag caatacggcc cagtatgtga caacatcctt  1920
tctgtggtga actccgtagg acagaaggag gacatggagt tactcacctt ctactcttcg  1980
acaaagcccg cgggctacaa cacgccagta ttcaacaata tatctactgg ggattttaat  2040
atatctcttt tgctgacccc tccttcaaca ccatcaggga gaagttttat tgaggatctg  2100
ctattcacct ccgtggagtc tgttgggctg cccacagatg aagcttacaa aaagtgcacc  2160
gctggaccgc tgggatttct aaaggacttg gcttgtgctc agaatataaa tggcctgtta  2220
gtgttaccac ccatcatcac tgcagaaatg cagacacttt acacttcatc ccttgttgcc  2280
agcatggctt taggcgggat cactgctgca ggcgccatac ccttcgccac acagctgcag  2340
gctcggatca accacctggg catcacacaa acaattcttt tgaaaaatca ggagaaaatc  2400
gcggcatcgt tcaataaagc tattggacac atgcaagaag gctttaaatc cacttctcta  2460
gctttgcaac aaattcaaga tgttgtgaat aaacagtccg ccattttgac tgaaacaatg  2520
gcatcactca acaaaaactt cggggccatc tcaagtgtta tccaggagat ctaccagcag  2580
ctggatagta ttcaggctaa tgctcaagtt gaccgcatca ttacgggaag gctctcctcc  2640
ctcagtgttc ttgcctcttc caaacaagca gagtacctgc gtgtgtctca gcagagggag  2700
ctggccaccc aaaagatcaa tgagtgtgtc aagagtcaga gcaaccgcta ctcattctgt  2760
ggaaacgggc ggcacgtgct tacaataccg cagaatgccc caaatggcat tgtattcatt  2820
cactttacgt atacacctga gtcctttgta aatgtcaccg ctatcgtggg cttctgcgtc  2880
aacccggcta acgcatctca atacgccatc gtgcctgcca atggacgagg aatttttcata  2940
caggtcaacg gcagctacta catcactgct agagatatgt acatgcctag ggacatcact  3000
gcaggtgaca ttgtgactct tacaagctgc caggctaact acgtttctgt aaataagacg  3060
gtaataacta ccctggtgga caatgacgac tttgacttc atgatgaact atctaaatgg  3120
tggaatgaaa ctaaacatga actgcctgac ttcgaccagt tcaactatac catccctgtg  3180
ttgaacataa cctatgatat agataaaatc gaggaggtga tcaaaggact gaatgattcc  3240
ttgatcgacc tggagaccct aagcatctta aaaacataca ttaagtggcc ctggtacgtg  3300
tggctggcca tctttttgc aataatcatc ttcattctaa ttctgggctg ggtgttttc  3360
atgactggct gctgtggatg ctgttgtggc tgctttggaa ttatccccct gatgtctaag  3420
tgtggtaaga aatctagtta ctacaccacc tttgataatg acgtggttac cgagcagtac  3480
aggccaaaga agagtgtgtg a                                           3501
```

SEQ ID NO: 27          moltype = AA   length = 1169
FEATURE                Location/Qualifiers
source                 1..1169
                       mol_type = protein
                       organism = Infectious Bronchitis Virus
SEQUENCE: 27
MSVLLPLLVT LLCALCSAVL YDINSYVYYY QSAFRPSNGW HLYGGAYAVV NVSNENNNAG    60
SASTCTAGAI GYSKNFSAAS IAMTAPPSGM AWSTAAFCTA HCNFTNIVVF VTHCYKSGSG   120
SCPLTGFIQS GYIRISAMKK ECSGPSCLFY NLTESVSKYP TFRSLQCVNN YTSVYLNGDL   180
VFTSNYTQDV VAAGVHFKSG GPITYKVMRE VKALAYFVNG DVILCDD TPRGLLACQY      240
NTGNFSDGFY PFTNTSIVKD KFIVYRESSV NTTLTLTNFT FSNESGAPPN TGGVNSFILY   300
QTQTAQSGYY NFNFSFLSGF VYEESNYMYG SYHPLCSFRP ENINNGLWFN SLSVSITYGP   360
LQGGCKQSFF QGRATCCYAY SYNGPRACKG VYSGELTQSF ECGLLVYITK SDGSRIQTAT   420
KAPVVTTNFY NNITLDKCVE YNIYGRVGQG FITNVTDSAF GYNYLQDGGL AILDTSGAID   480
IFVVKGVYGL NYYKVNPCED VNQQFVVSGG TLVGVLTSRN ETGSQFLENQ FYIKLTNGTH   540
RSRRSVNENV TSCPYVSYGK FCIKPDGSTS VIVPKELEQF VTPLLNATEY VPIPDSFNLT   600
VTDEYIQTRM DKVQINCLQY VCGNSFECRN LFQQYGPVCD NILSIVNSVS QKEDMELLTF   660
YSSTKPGFN TPILSNLSTG DFNISLLLTP PSSTTGRSFI EDLLFTSVES VGLPTDDAYK    720
KCTAGPLGFL KDLACAREYN GLLVLPPIIT AEMQTMYTSS LVASMALGGI TAAGAIPFAT   780
QLQARINHLG ITQAVLLKNQ EKIAASFNKA IGQMQEGFRS TSLALQQIQD VVNKQSAILT   840
ETMASLNKNF GAISSVIQDI YQQLDVIQAD AQVDRLITGR LSSLSVLASA KQSEHIIASQ   900
QRELATQKIN ECVKSQSTRY SFCGNGRHVL TIPQNAPNGI VFIHFTYTPE SFVNVTAIVG   960
FCVKPANASQ YAIVPANGRG IFIQFNGSYY ITARDMYMPR NITAGDIVTL TSCQSNYVSV  1020
NKTVITTFVD NDDFDFDDEL SKWWNDTKHE LPDFDEFNYT APILDIDSEI DRIQGVIQGL  1080
NDSLIDLETL SILKTYIKWP WYVWLAIAFA TIIFILILGW VFFMTGCCGC CCGCFGIIPL  1140
MSKCGKKSSY YTTFDNDVVT EQYRPKKSV                                     1169

```
SEQ ID NO: 28            moltype = DNA  length = 3510
FEATURE                  Location/Qualifiers
source                   1..3510
                         mol_type = other DNA
                         organism = Infectious Bronchitis Virus
SEQUENCE: 28
atgagcgtcc tgctcccctt gctggttact ctcttgtgtg cgctttgctc ggctgtattg   60
tatgatatca attcatacgt atactactac caaagtgctt ttcgtccgag taacggctgg  120
cacttgtatg ggggagccta tgcagtggtt aatgtctcca atgtcaaata caatgccagc  180
tccgcttcca cttgcactgc tggagctatt ggctacagca aaaatttctc tgctgcatct  240
atagccatga ccgcaccacc ttcagggatg gcctggagta ctgctgcctt ctgcacggcg  300
cattgcaatt tcaccaacat cgttgttttt gttacacact gctataagtc cggaagtggt  360
agctgccctt taacggggtt tattcagtcc gggtacatcc gcatctcagc tatgaagaag  420
gagtgcagcg gcccatcctg cctgttctat aacctgacag aatctgtatc taaataccct  480
accttcagat cacttcagtg cgtgaacaat tacactagcg tgtatttgaa tggggactta  540
gtgtttacta gcaactatac tcaggatgta gtcgccgccg gggtgcactt caaatccgga  600
ggcccgataa cttacaaggt gatgagagag gtgaaggctc tcgcctactt cgtaaacggg  660
accgcgcagg acgtcatcct ctgtgatgat acgccacgcg gcctcctggc ttgccagtat  720
aatacaggaa actttcaga cgggttctac cccttcacta cacaagcat tgtgaaggat  780
aagttcattg tctacaggga gagctccgtg aatactactc tgaccttgac caacttcact  840
ttcagtaatg aaagcggtgc tccccccaaac accggcgggt tcaacagctt cattctgtac  900
caaactcaaa cggcccaatc aggttactac aactttaact tcagcttcct ttctggcttc  960
gtgtatgagg agtcaaacta tatgtatgga agctaccacc cactgtgctc tttcaggcct 1020
gagaatatta ataacggtct gtggttcaat agcctctctg tgtcgataac ctatggtcct 1080
ctgcagggtg ggtgcaaaca atcattcttc cagggaaggg caacctgctg ctacgcgtac 1140
tcttacaatg ggcccagggc ctgcaaaggc gtttattctg gagaactaac gcaatcattt 1200
gagtgtgggc tgttggttta tatcacaaag agtgatggaa gcaggatcca gactgcaacg 1260
aaagctccgg ttgtgacaac caacttctac aacaatatta ctttggacaa gtgtgtggag 1320
tacaacatat acggccgtgt tggtcaagga ttcattacca atgtaactga ctccgcattt 1380
ggttacaact acctgcagga tggtggtcta gcgatactgg acacgagtgg cgccatcgac 1440
attttcgttg tgaaaggagt gtatggactg aactattaca aagtcaatcc atgtgaagat 1500
gtgaatcagc aatttgtagt ttcagggggg acacttgtgg gcgtcttaac ttctcggaac 1560
gagactggat ctcagttcct ggaaaaccag tttacataa aattgacaaa cggaactcat 1620
cgttctaggc ggagtgtgaa tgaaaatgtg accagctgtc cttacgtttc ttacgggaag 1680
ttttgcatca agcctgacgg atctacttct gttatcgtgc cgaaggaact agagcagttt 1740
gtcaccccc tgttgaatgc aacagagtat gtgcctatcc ctgacagctt caaccttaca 1800
gtgaccgacg agtacatcca aaccaggatg gataaagtgc agatcaactg cctccagtac 1860
gtgtgtggga actcatttga atgcagaaat ttatttcagc agtatgggcc tgtgtgtgac 1920
aatattctga gcatcgtgaa cagtgtttca cagaaagaag atatggagct cttgacctttt 1980
tatagttcaa ccaagccatt cggcttcaac actcccatac tgtctaatct gagtactgga 2040
gattttaata tctcactgtt gctaacaccc cccagcagca ccactggaag atcctttatc 2100
gaagacctcc tttttacttc cgtcgagtct gttggacttc tcacagatga tgcatataag 2160
aaatgcacgg caggccctct gggcttctta aaagatctcg catcgctcg ggaatataac 2220
gggctgctgg tgctgccccc cattattact gcagagatgc agacaatgta tacgtcctcg 2280
cttgtggctt ccatggcatt aggcggcatt acagctgccg gggcaattcc atttgcaaca 2340
cagctgcagg caagaatcaa tcatctcggc atcaccacag ctgtgctttt gaagaatcaa 2400
gaaaagatag cagcctcctt taataaggcg atagggcaga tgcaggaagg gttccgatcc 2460
acaagtctcg cactgcaaca aattcaggac gtagtaaaca aacagtctgc gattctcacc 2520
gaaaccatgg ctagcctcaa caagaacttt ggggctatta gctcggtcat acaggacatc 2580
tatcagcaac tggatgttat tcaggctgat gcccaggtgg atagattgat cacaggcaga 2640
ctttccagcc tgtctgtctt agcctctgct aagcagagtg agcatattat agcaagccag 2700
cagcgcgagt tagccacaca gaaaattaac gaatgtgtta aaagtcagag tacaagatac 2760
agcttttgtg gaaatggccg acacgtgctt acaataccgc agaatgctcc aaatggaatc 2820
gtcttattc atttcacgta tacaccagaa tcatttgtta acgtcactgc aattgtgggc 2880
ttctgcgtta gcccgccaa cgccagccaa tatgccatcg taccagcgaa cggtcggga 2940
atatttatcc agttcaacgg ctcttattat atcaccgcac gggacatgta catgccacga 3000
aatattacag ctggtgacat cgtcacgcta acatcctgtc agagtaatta tgtgtcagta 3060
aacaaaacag tcatcaccac ctttgtggac aacgatgact ttgacttcga cgatgaactg 3120
tcgaagtggt ggaatgacac caagcacgag ctgccagact tcgatgagtt taactacacg 3180
gctcctatcc tggatattga ttccgagata gaccgcatcc agggtgtaat acaaggacta 3240
aatgattctc tcattgatct cgagacactg tccatcctaa aaacctacat taagtggcca 3300
tggtacgttt ggctggcaat agcttttgcc acaatcatct ttattcttat cctcggatgg 3360
gtcttttca tgacaggctg ttgtggatgt tgttgtggtt gctttgggat aataccctg 3420
atgagcaaat gtggcaaaaa atcatcttac tacacaacat ttgataatga tgtggtcact 3480
gagcagtacc gcccgaaaaa gtccgtttga                                    3510
```

```
SEQ ID NO: 29            moltype = AA  length = 1159
FEATURE                  Location/Qualifiers
source                   1..1159
                         mol_type = protein
                         organism = Infectious Bronchitis Virus
SEQUENCE: 29
MLVTPLLLVT LLFALCSAAL YDNSSYVYYY QSAFRPPNGW HLHGGAYAVV NTSIESNNLR   60
ECIVGIIGGD RVVNASSIAM TAPQPGMDWS SRQFCTAHCN FSDITVFVTH CYKHNGCPIT  120
GSIPQHSIRV SAMKKGRLFY NLTVSVNKYP TFKSFQCVNN FTSVYLNGDL VYTSNETTDV  180
TSAGVYFNAG GPITYKVMRE VKALAYFVNG TAQDVILCDG SPRGLLSCQY NTGNFSDGFY  240
PFTNSSLVKQ KFIVYRENSI NTTLKLHNFT FHNETGANPN LSGVQNIQTY QTQTAQSGYY  300
NFNFSFLSGF VYKESNFMYG SYHPSCNFRP ETINNGLWFN SLSVSIAYGP LQGGCKQSVF  360
```

```
SGRATCCYAY SYGGPSLCKG VYLGELKSDF ECGLLVYVTK SDGSRIQTAT EPPVITQHNY   420
NNITLNTCVD YNIYGRTGQG FITNVTDSAV SYNYLADAGM AILDTSGSID IFVVQGEYGL   480
TYYKVNPCED VNQQFVVSGG KLVGILTSRN ETGSQLLENQ FYIKITNGTR RSRRSITANV   540
TNCPYVSYGK FCIKPDGSVS AIVPKELEQF VAPLLNVTEN VLIPNSFNLT VTDEYIQTRM   600
DKIQINCMQY VCGNSLDCRK LFQQYGPVCD NILSVVNSVG QKEDMELLNF YSSTKPSGFN   660
TPVFSNLSTG DFNISLLLTP PSSTTGRSFI EDLLFTSVES VGLPTDEAYK KCTAGPLGFL   720
KDLACAREYN GLLVLPPIIT AEMQTLYTSS LVASMAFGGI TAAGAIPFAT QLQARINHLG   780
ITQSLLQKNQ EKIAASFNKA IAVVQEGFRS TSLALQQVQD VVNKQSAILT ETMASLNKNF   840
GAISSVIQDI YQQLDAIQAN AQVDRLITGR LSSLSVLASA KQAEYIRVSQ QRELATQKIN   900
ECVKSQSIRY SFCGNGRHVL TIPQNAPNGI VFIHFTYTPE SFVNVTAIVG FCVKPANASQ   960
YAIVPANGRG IFIQVNGSYY ITARDMYMPR DITAGDIVTL TSCQANYVSV NKTVITTFVD  1020
NDDFDFDDEL SKWWNDTKHE LPDFDEFNYT VPILDIGSEI DRIQGVIQGL NDSLIDLETL  1080
SILKTYIKWP WYVWLAIAFA TIIFILILGW VFFMTGCCGC CCGCFGIIPL MSKCGKKSSY  1140
YTTFDNDVVT EQYRPKKSV                                              1159

SEQ ID NO: 30          moltype = AA  length = 3480
FEATURE                Location/Qualifiers
source                 1..3480
                       mol_type = protein
                       organism = Infectious Bronchitis Virus
SEQUENCE: 30
ATGCTGGTGA CACCGTTGCT CCTCGTGACC CTGTTATTTG CACTGTGCAG CGCAGCACTG   60
TATGATAATA GCTCGTATGT CTATTATTAC CAATCAGCAT TTCGACCCCC AAATGGATGG   120
CACCTGCATG GCGGAGCCTA TGCTGTGGTA AACACTTCAA TCGAGTCAAA CAACCTGAGG   180
GAATGCATTG TAGGGATTAT AGGTGGTGAC AGAGTTGTGA ATGCTAGCAG CATCGCTATG   240
ACAGCTCCCC AGCCAGGAAT GGACTGGTCA AGCAGGCAAT TTTGCACCGC TCACTGTAAC   300
TTTTCGGATA TAACAGTTTT CGTAACTCAC TGCTACAAGC ACAACGGTTG CCCCATTACT   360
GGGAGTATCC CTCAGCACAG TATACGCGTA TCGGCTATGA AGAAAGGCCG GTTGTTCTAC   420
AATTTGACGG TCTCCGTAAA TAAGTATCCA ACATTCAAGA GTTTCCAGTG CGTGAACAAT   480
TTTACATCTG TGTACCTGAA CGGGGACTTT GTATACACTT CCAATGAAAC GACGGATGTT   540
ACAAGTGCTG GTGTTTATTT CAATGCAGGA GGGCCTATCA CATATAAAGT GATGAGGGAG   600
GTGAAAGCGC TGGCTTACTT CGTGAACGGG ACGGCCCAGG ATGTGATCCT GTGTGATGGC   660
TCTCCACGTG GCCTCTTGAG CTGTCAGTAC AACACCGGCA ATTTTAGTGA TGGATTTTAC   720
CCTTTCACAG ACTCTTCTTT AGTGAAACAA AAGTTTATAG TCTACAGGGA GAATTCTATT   780
AATACCACAT TGAAACTCCA TAATTTCACA TTTCACAATG AGACCGGAGC CAACCCCAAC   840
CTCTCAGGAG TTCAGAATAT CCAGACCTAC CAGACGCAGA CAGCTCAGAG CGGATACTAC   900
AACTTCAACT TCTCATTCCT GTCGGGTTTT GTTTATAAAG AGAGCAACTT CATGTATGGG   960
TCATACCATC CAAGCTGCAA CTTCCGGCCT GAGACGATCA ACAATGGCCT CTGGTTCAAT  1020
TCTTTATCCG TCTCCATTGC TTATGGACCC CTGCAGGGGG GGTGCAAGCA GTCTGTCTTT  1080
AGTGGCAGGG CAACTTGCTG CTATGCCTAC AGTTACGGGG GTCCGTCTCT GTGCAAAGGA  1140
GTATACCTTG GAGAACTGAA ATCAGATTTT GAGTGCGGTT TACTGGTATA TGTTACTAAG  1200
TCTGATGGCT CTCGCATCCA GACAGCGACA GAACCCCCTG TGATTACACA GCATAACTAT  1260
AACAACATCA CTTTGAACAC ATGTGTTGAT TATAACATTT ATGGACGGAC AGGCCAGGGC  1320
TTTATCACCA ATGTTACTGA CTCTGCAGTC TCCTACAATT ATCTTGCCGA TGCAGGGATG  1380
GCTATTTTGG ACACTTCAGG TTCCATCGAT ATCTTCGTGG TCCAAGGAGA GTATGGCCTC  1440
ACTTATTATA AAGTGAACCC TTGTGAGGAC GTTAATCAAC AGTTCGTGGT TAGCGGTGGG  1500
AAACTCGTGG GGATATTGAC TTCACGAAAC GAGACAGGTT CTCAGCTCCT GGAAAATCAG  1560
TTTTACATCA AAATCACAAA CGGCACACGC AGGAGCAGAC GGAGCATAAC AGCAAATGTG  1620
ACCAACTGTC CTTACGTCTC CTATGGGAAG TTCTGCATTA AGCCCGATGG AAGCGTGTCA  1680
GCCATTGTTC CGAAGGAACT GGAACAGTTT GTCGCTCCAC TGCTTAATGT GACTGAGAAC  1740
GTGCTGATCC CTAACTCTTT CAATCTAACA GTGACAGATG AGTACATTCA AACAAGGATG  1800
GATAAGATAC AGATAAACTG CATGCAGTAT GTTTGTGGAA ACAGCCTCGA CTGCCGTAAG  1860
CTGTTTCAGC AATATGGCCC CGTTTGTGAC AACATCCTTT CGGTGGTGAA CAGTGTCGGA  1920
CAGAAAGAAG ATATGGAGCT CCTGAATTTT TACTCCAGTA CGAAGCCCTC CGGGTTCAAC  1980
ACACCTGTTT TCAGCAACCT GAGCACAGGA GATTTTAACA TTTCTTTGCT ACTAACACCA  2040
CCCTCCTCCA CTACGGGCCG GTCATTCATT GAAGACTTAC TCTTCACTTC TGTTGAAAGT  2100
GTAGGTCTAC CGACTGATGA AGCTTATAAG AAGTGTACCG CCGGCCCTCT TGGCTTCCTC  2160
AAGGATCTGG CCTGCGCAAG AGAATACAAT GGCCTACTGG TGCTGCCGCC GATCATCACA  2220
GCCGAGATGC AAACCTTGTA TACTTCTTCC CTCGTCGCGT CCATGGCATT CGGGGGTATC  2280
ACCGCCGCTG GGGCTATTCC ATTCGCTACT CAGCTGCAAG CTAGAATTAA TCACCTTGGC  2340
ATTACGCAAT CACTTCTCCA AAAAAATCAG GAGAAGATTG CTGCCAGTTT TAACAAGGCA  2400
ATCGCCGTGG TGCAGGAAGG TTTTCGATCG ACCAGCCTGG CACTCCAGCA GGTACAGGAC  2460
GTTGTTAACA AACAGTCCGC CATACTTACC GAGACAATGG CCTCCCTCAA CAAGAACTTT  2520
GGAGCAATCA GCAGTGTCAT CCAAGACATT TATCAGCAAT TGGATGCCAT TCAGGCAAAC  2580
GCACAGGTGG ACCGCCTGAT CACCGGGCGT CTAAGTAGCC TGTCCGTGCT GGCCAGTGCC  2640
AAGCAAGCCG AGTACATCAG AGTGTCACAG CAGAGAGAAC TTGCCACGCA GAAGATTAAT  2700
GAGTGCGTTA AGAGCCAGTC TATTCGGTAC AGCTTTTGTG GGAATGGAAG ACATGTGCTG  2760
ACAATACCAC AGAACGCGCC AAATGGTATA GTGTTTATTC ACTTCACCTA CACCCCAGAA  2820
TCCTTCGTGA ATGTCACAGC AATCGTGGGT TTCTGTGTGA AGCCAGCTAA TGCAAGTCAA  2880
TACGCGATAG TACCCGCGAA CGGCCGCGGG ATCTTCATTC AGGTCAATGG TTCCTATTAC  2940
ATAACTGCAA GGGACATGTA CATGCCTCGA GATATCACCG CGGGAGACAT CGTCACGTTA  3000
ACTTCTTGTC AGGCCAATTA CGTAAGCGTT AATAAAACTG TGATAACGAC TTTTGTAGAT  3060
AACGATGACT TCGACTTTGA TGATGAATTA AGCAAATGGT GGAATGACAC AAAGCATGAA  3120
CTTCCTGACT TTGACGAATT TAATTACACT GTGCCTATAC TGGACATAGG GTCAGAGATT  3180
GACAGAATTC AAGGAGTCAT TCAAGGCCTT AATGACTCAT TGATAGACCT GGAGACCCTG  3240
TCTATTCTGA AGACCTACAT CAAATGGCCA TGGTACGTCT GGCTGGCGAT AGCCTTTGCT  3300
ACCATTATAT TCATCCTTAT CCTGGGGTGG GTGTTCTTCA TGACTGGCTG TTGCGGATGC  3360
TGCTGTGGAT GTTTTGGGAT CATTCCCCTA ATGAGCAAAT GTGGTAAAAA AAGTTCCTAT  3420
TACACGACCT TTGATAATGA CGTGGTAACC GAGCAGTACA GACCAAAAAA ATCTGTCTGA  3480
```

```
SEQ ID NO: 31          moltype = AA   length = 1159
FEATURE                Location/Qualifiers
source                 1..1159
                       mol_type = protein
                       organism = Infectious Bronchitis Virus
SEQUENCE: 31
MLGKSLFIVT LLLALCEGGL VGVNYTYYYQ SRYRPPNGWH MQGGAYKVVN KTTISYTSQE    60
CTIGVIRGGV TINQSAIAFT SATGRVGVKK GVCTVYCNYT SFYVFVTHCG GTGHNCIVNT   120
KKLGVLVFGV KNYNDQFIYN ITLNAAGPYA NFKAWQCLSN YTSVFLNGNL LYTSNYTEDV   180
KAAGVYAKQV NGLERRVMRD TPVMAYFVNG TVQDVILCDD SPKGRLACQY NTGNFSDGLY   240
PVYEEPVASN FTFVPLHTSS TSYGVLHNFT FNNVTGVAPN QEHIARFNIS TISEGYVNFK   300
FNFLNSFTYV ESDFDRGSYY GKPGSRCNFG LESINRGLSF NSLTVSIGYG PISGGCKQSV   360
WKNEATCCFA YKYNGGSRNC KGLYTFDRDV NYECVLLVFI SKPDGSRIRT ATSPPVYSNN   420
NVNINLGLCV DYNVYGITGR GLITNITESV HPGYLDHGGL VLLDATGSID TFVLHSDKLT   480
SYYKVNPCSD INEQYVVSGG NLVGKLTSNN QTVAQQLGDM FYVKFSTSGR RIRRATSENV   540
TSCPYVTYGK FCIKPDGDIS NIVPEEVKDY TSLLLNRTDY VLIPNSFNLT VTDEFIQTQF   600
QKIQINCIQY VCGSSIQCKQ LFQQYGSVCG NILSIVNGIA LQDNAEMLHF YSSTKPRGFD   660
TNSFVNFTAG EFNISLVLPK NGQPTGRCLI EDLLFDKVES LGLPGDSAYQ KCTSGPLGFV   720
KDLVCAQNYN GLLVLPPIIT AEMQTLYTSS LVVSMAFGGI TAARAIPFAT QIQARINHLG   780
ITQTVLQKNQ EKIAASFNKA MKHMQDGFSA TSLALQQVQD VVNEQGAILQ QTMHSLNKNF   840
GAISHVIQDI YKQLDALEAN AQVDRIITGR LSSLSVLASA KQLEYTKVSQ QRELAKEKIN   900
ECVKSQSNRH GFCGEGMHIM SIPQNAPNGI VFLHFTYTPE TYANVTAVVG FCVKPGNGTE   960
YGLVPVVGRG IFIEVNGTYY ITGRDMYSPR AITAGDVVKL TPCQANYQSI NRTVITTFVD  1020
EDDFDFDHEL SKWWNETSRD FPNLDEFNYT IPVLNISNEI DKIQEVIQGL NDSIIDLETL  1080
SILKTYIKWP WYVWLAIFFA IIIFILILGW VFFMTGCCGC CCGCFGIIPL MSKCGKKSSY  1140
YTTFDNDVVT EQYRPKKSV                                               1159

SEQ ID NO: 32          moltype = DNA   length = 3480
FEATURE                Location/Qualifiers
source                 1..3480
                       mol_type = other DNA
                       organism = Infectious Bronchitis Virus
SEQUENCE: 32
atgctgggca aatctctctt catcgttaca ctgctcctgg cactgtgtga agggggactg    60
gtcggtgtaa actacacata ttattaccag agcagatacc ggccgcccaa cggatggcat   120
atgcagggag gtgcgtataa agtggtgaat aagactacaa tctcctatac gagtcaagag   180
tgcaccatcg gcgtgatcag aggcggagtg accattaatc agtctgcaat cgccttcact   240
tcagcaactg gacgagttgg cgtgaaaaag ggggtttgta ctgtctactg caattatact   300
tcttttttacg ttttttgtgac tcactgcggg ggtactggtc acaactgcat tgttaacact   360
aagaagctcg gcgttttggt gtttggcgtc aagaactaca atgaccagtt catttacaac   420
attactctga atgccgctgg accctatgcc aactttaaag cctggcagtg tctgagtaac   480
tatacgagtg tttttcttaaa tggaaacctc ttatatacat cgaattacac agaagatgtt   540
aaggcagcgg gggtatatgc aaaagcaggtc aacggacttg agagaagagt gatgagggac   600
accccagtca tggcctactt tgtaaatggt accgtgcagg atgtcatctt gtgtgatgat   660
tctccaaaag ggaggctagc ctgccagtat aatacaggga actttagcga cggactatat   720
cctgtatatg aggaaccagt ggcttcgaac ttcaccttcg tccctctcca cacatcttct   780
acttcctatg gggtcctgca taattttacg ttcaacaatg tcacgggagt tgcacctaac   840
caggagcaca tcgcgcgctt caacataagt accatatccg aaggctacgt taatttcaag   900
tttaactttc ttaactcttt tacttacgtg gagtctgatt ttgacagagg gagctactat   960
ggcaaacctg gatcacgctg caacttcggc cttgagtcaa tcaataggg attgagcttt  1020
aattcactca ccgtttctat tggttatggt cctatctccg gcgggtgcaa acagtctgtg  1080
tggaagaatg aggccacctg ctgctttgcg tataaataca atggtggctc gcggaactgt  1140
aaaggcctgt acacctttga tcgtgatgtg aattatgaat gtgtgcttct ggtctttata  1200
agtaagcctg atggctcccg tatcaggact gctacctcac cgcccgtgta ctcaaataat  1260
aacgttaaca ttaacttagg gctgtgtgtt gattacaacg tgtacggcat tacaggccgg  1320
ggacttatta ctaacatcac tgaaagtgtc cacccggggt atcttgacca tggtggtctc  1380
gttctactgg atgcaacagg gagcattgac acatttgtgc tgcattccga caaactgacc  1440
agttactaca aagtgaatcc ttgctctgat attaatgaac aatatgtggt tagcggcggc  1500
aaccttgtag gaaaattgac atctaacaac caaacagttg cacaacagct gggtgatatg  1560
ttttatgtaa agttctccac gagtgggaga cgtattcggc gcgctacgtc agaaaatgtg  1620
acatcctgcc cctacgtgac gtatggtaaa ttctgtatca aaccagatgg agatatttca  1680
aatatcgtgc cggaggaggt gaaggactat acaagcttgc tgctgaaccg cacagactac  1740
gtgctcatcc caaactcctt caatttaaca gttactgatg agttcataca gactcagttt  1800
cagaaaatcc agattaattg tatccagtat gtgtgcggaa gctctataca gtgcaagcaa  1860
ctgttccagc agtacggcag tgtctgcgga aatatccttt caattgtcaa tgggatcgca  1920
cttcaagata tgcagaaat gcttcatttc tacagctcca ccaaacccg tggctttgac  1980
accaacagct ttgtgaactt cacagcaggg gagttcaata tttccctcgt actgcccaag  2040
aacggccgca actgggag gtgcctgatt gaggacctgc tgtttgacaa ggtagagtcc  2100
ttgggactcc ccgggatag tgcttatcag aagtgcacat ctggaccct aggattcgta  2160
aaagatctcg tctgtgccca gaactataac gggcttctcg ttctgccacc aatcatcacg  2220
gctgagatgc agacattata cacctctagc ttggtggtct ccatggcttt tggcggaatc  2280
acagcagcaa gggcaatacc ttttgccaca cagatccagg ctagaatcaa ccacttgggg  2340
ataacagaa ccgtactcca aaagaaccag gagaagatcg cgcaggttt caacaaggcc  2400
atgaagcaca tgcaagacgg ctttagtgcc acttcactcg ctctgcagca gttcaagat  2460
gtggtgaatg agcagggtgc gatcttgcag caaaccatgc acagcttgaa caaaaatttt  2520
ggcgccattt ctcatgtcat acaggacata tacaagcagc tcgatgcttt agaagcaaac  2580
gctcaggtgg atcgaataat tactggtaga ctgagcagcc tgtcggtgct ggcatcagcc  2640
aaacaacttg aatatacaaa ggtgagccag cagagggagt tagccaagga gaagatcaat  2700
```

-continued

```
gaatgcgtga aatcacaatc caaccggcac ggcttctgtg gtgaaggaat gcatattatg 2760
agcataccac agaatgctcc aaatggcatt gtcttcctgc acttcacgta cactccggag 2820
acttatgcaa atgtaacagc tgtggtaggc ttctgcgtga aacccggcaa tggaacagag 2880
tatggactag tcccagtcgt ggggcgcggc atatttattg aggtgaatgg gacatactac 2940
atcaccggcc gggacatgta cagtccgagg gctatcacag ctggtgacgt tgtgaagctg 3000
actccctgtc aggcgaatta ccaaagtatt aaccgaacag taattaccac tttcgttggac 3060
gaggatgact cgactttga tcatgaacta tccaaatggt ggaacgaaac gagtcgagac 3120
ttccctaacc tggatgaatt taattacacc attcctgtgt tgaatatttc caatgaaatt 3180
gataaaatac aagaagtaat tcaaggtttg aacgacagca taatcgacct ggaaaccctg 3240
agcatactga agacttacat caaatggccc tggtacgttt ggctggccat cttctttgct 3300
atcattattt ttattttgat tctggggtgg gtgttcttca tgaccggctg ttgtggatgc 3360
tgctgtggtt gcttcggtat cataccactc atgtcaaaat gtggaaagaa aagctcctat 3420
tacaccacct ttgacaacga tgtagtaact gaacagtaca gacctaagaa gtcagtgtga 3480
```

SEQ ID NO: 33                    moltype = AA   length = 1162
FEATURE                          Location/Qualifiers
source                           1..1162
                                 mol_type = protein
                                 organism = Infectious Bronchitis Virus
SEQUENCE: 33

```
MLVTPLLLVT LLCVLCSAAL YDSSSYVYYY QSAFRPPNGW HLHGGAYAVV NISSESNNAG   60
SSPGCIVGTI HGGRVVNASS IAMTAPSSGM AWSSSQFCTA HCNFSDTTVF VTHCYKYDGC  120
PITGMLQKNF LRVSAMKNGQ LFYNLTVSVA KYPTFKSFQC VNNLTSVYLN GDLVYTSNET  180
TDVTSAGVYF KAGGPITYKV MREVKALAYF VNGTAQDVIL CDGSPRGLLA CQYNTGNFSD  240
GFYPFINSSL VKQKFIVYRE NSVNTTFTLH NFTPHNETGA NPNPSGVQNI QTYQTQTAQS  300
GYYNFNFSFL SSFVYKESNF MYGSYHPSCN FRLETINNGL WFNSLSVSIA YGPLQGGCKQ  360
SVFSGRATCC YAYSYGGPSL CKGVYSGELD LNFECGLLVY VTKSGGSRIQ TATEPPVITR  420
HNYNNITLNT CVDYNIYGRT GQGFITNVTD SAVSYNYLAD AGLAILDTSG SIDIFVVQGE  480
YGLTYYKVNP CEDVNQQFVV SGGKLVGILT SRNETGSQLL ENQFYIKITN GTRRFRRSIT  540
ENVANCPYVS YGKFCIKPDG SIATIVPKQL EQFVAPLLNV TENVLIPNSF NLTVTDEYIQ  600
TRMDKVQINC LQYVCGNSLD CRDLFQQYGP VCDNILSVVN SIGQKEDMEL LNFYSSTKPA  660
GFNTPPLSNV STGEFNISLL LTTPSSPRRR SFIEDLLFTS VESVGLPTDD AYKNCTAGPL  720
GFLKDLACAR EYNGLLVLPP IITAEMQTLY TSSLVASMAF GGITAAGAIP FATQLQARIN  780
HLGITQSLLL KNQEKIAASF NKAIGRMQEG FRSTSLALQQ IQDVVNKQSA ILTETMASLN  840
KNFGAISSVI QEIYQQLDAI QANAQVDRLI TGRLSSLSVL ASAKQAEHIR VSQQRELATQ  900
KINECVKSQS IRYSFCGNGR HVLTIPQNAP NGIVFIHFSY TPDSFVNVTA IVGFCVKPAN  960
ASQYAIVPAN GRGIFIQVNG SYYITARDMY MPRAITAGDI VTLTSCQANY VSVNKTVITT 1020
FVDNDDFDFN DELSKWWNDT KHELPDFDKF NYTVPILDID SEIDRIQGVI QGLNDSLIDL 1080
EKLSILKTYI KWPWYVWLAI AFATIIFILI LGWVFFMTGC CGCCCGCFGI MPLMSKCGKK 1140
SSYYTTFDND VVTEQNRPKK SV                                          1162
```

SEQ ID NO: 34                    moltype = DNA   length = 3489
FEATURE                          Location/Qualifiers
source                           1..3489
                                 mol_type = other DNA
                                 organism = Infectious Bronchitis Virus
SEQUENCE: 34

```
atgctggtca cgcctctgct gcttgtcaca ctgttgtgcg tcttgtgtag cgcggctctg   60
tatgattcaa gtagctatgt ttactactac cagtccgcat ttaggccacc taacggctgg  120
cacttacacg gcggagctta tgccgtggtt aatatttcta gtgagagcaa caacgccggc  180
agctcgcccg gctgcattgt tggtacgatt catggaggcc gggtggttaa cgctagcagc  240
atagctatga cagctccatc cagcgggatg gcttggtcgt cttcacaatt ctgcactgca  300
cactgcaatt tctcagatac tactgtgttt gtgacacatt gttacaagta cgacggttgt  360
cctatcacgg gtatgctcca gaagaacttc ctgcgcgtca cgccatgaa aaatggccag  420
ttgttctata acctgaccgt gtctgtagct aaatacccta ccttcaagtc tttccagtgc  480
gtcaacaatc taacaagtgt gtatttgaac ggcgatctcg tatacacttc caatgaaacc  540
acagatgtaa catctgcagg tgtttatttc aaagccggtg gcccaattac atataaagtg  600
atgcgcgagg tgaaagccct cgcttacttc gtcaatggca ccgccaaga tgtgatactt  660
tgcgacgggt cacctcgtgg cttgttggcc tgccagtaca atacaggaaa ttttagcgat  720
ggatttttat ctttcatcaa ttcatccctg gtgaagcaaa aatttattgt atatagagaa  780
aacagtgtaa acaccacctt tacgctgcat aacttcactt ccacaacga aactggggca  840
aacccgaatc caagtggggt acagaatata caaacatacc agacccaaac tgcccagtct  900
ggctactaca actttaattt ctcttttttg agcagcttcg tttataagga gtccaacttc  960
atgtatggtt cctatcaccc cagctgtaat tttaggctgg agaccatcaa taacgggctg 1020
tggtttaact cccttagtgt gagcattgca tatgggcccc tccaggggg ctgtaaacaa 1080
tctgtcttca gcggcagagc aacatgttgt tacgcctatt cttatggagg cccgtccctc 1140
tgcaagggag tatactccgg tgagcttgat ctcaattttg aatgcggctt attagtatat 1200
gtgacaaagt caggaggatc tagaatccag accgctaccg aacctcctgt gatcacccgc 1260
cataattata taatatcac tttgaatact tgtgtcgatt acaacatcta cggcaggacg 1320
gggcaagggt ttataaccaa cgtgacagac agtgcagttt cctacaacta cctggctgac 1380
gccggcctcg caatcttga tacaagtggc tcgatagata tcttcgtcgt gcaggggag 1440
tatgggctga cttattataa ggtgaatcct tgtgaggacg tgaaccagca gtttgtggtc 1500
agtggcggca aactagtcgg aattctgaca tctcgtaatg aaacaggaag ccagcttcta 1560
gaaaatcaat tctacattaa aataacaaac gggaccagac gcttccgccg gagtataacc 1620
gaaaacgtag ccaactgccc ctacgtttcc tatggaaagt tctgcataaa acccgatggc 1680
agtattgcga ctatcgtccc aaagcagttg gagcagttcg ttgcaccact gctgaatgtg 1740
actgaaaacg ttctgattcc aaactcattt aatttaacag tgacagatga atacatacag 1800
actagaatgg acaaagtaca gattaactgt ctgcagtacg tttgtggcaa ctcactggac 1860
tgcagggact gtttcagca gtatgggccc gtgtgtgaca atattctttc tgtcgtgaat 1920
```

```
tcgatcggtc agaaggagga catggaactg ctcaacttct actctagcac taaaccggct   1980
ggctttaata cgccattcct gtcaaacgtt tccaccggtg aatttaacat ttcgcttctc   2040
ttgactactc catcttcccc acgtcggagg agctttattg aggatctgct gttcactagt   2100
gtagagtctg tgggtctccc aacggatgat gcatacaaaa attgcaccgc ggggcccctt   2160
gggttcctaa aggatcttgc atgcgcgagg gaatacaacg gtctgctcgt actgccgcca   2220
atcattactg cagagatgca aaccctctac acgagctcct tggtggcttc catggccttt   2280
ggaggtatca ctgctgctgg tgctataccg tttgcaacgc agctacaagc ccgaataaac   2340
catctcggca tcacacagtc tttactctta aaaaatcagg agaagatcgc tgcaagcttt   2400
aacaaggcca ttggtcgaat gcaggaaggc tttcgcaagc caagtctggc cctccagcag   2460
attcaggacg tagtcaacaa acagagcgca atcctgaccg aaaccatggc tagcctcaac   2520
aagaatttcg gagcaatctc ttctgtgatt caggagatct atcagcaatt ggatgccata   2580
caagccaacg cacaggtgga caggctaata acgggtagac tgtcatccct gagcgttctt   2640
gcttcagcca agcaggcgga acacattcgg gttagtcaac agagagagct ggccactcag   2700
aaaatcaatg agtgcgtgaa aagccagtca atccggtact cctttgtgg aaatgggcgg    2760
cacgtgctta ctattcctca aaatgcccct aatggaattg ttttcattca ctttagttac    2820
acacccgatt cattcgtcaa tgtcacagct atagtgggtt tctgtgttaa gccagcgaac    2880
gcctcacaat acgcaattgt gcccgcaaat ggacgtggaa tctttattca agtgaatggg    2940
tcttactata ttaccgcgcg agatatgtat atgccaagac caataaccgc aggagacatt    3000
gtcacattaa ccagctgcca ggctaattac gtaagcgtaa ataagacagt catcacaacc    3060
tttgttgaca cgatgacttt cgactttaac gatgagctat caaagtggtg gaacgatacc    3120
aagcatgagc tgcccgattt tgacaagttc aactacacag tgcctatctt agatatcgat    3180
tcagaaatcg acaggattca aggagtgatc cagggtctta acgactcgct tattgaccta    3240
gagaaactga gcatactgaa aacatacatt aaatggccct ggtacgtgtg gctggcgatc    3300
gcgttcgcta ccatcatctt tatactgatc ttggggtggg tgttcttcat gactggctgt    3360
tgtgggtgct gctgcggatg ttttggaatc atgcccctga tgtccaaatg cggaaagaag    3420
tcctcatatt atacaacatt tgacaacgat gttgtgacgg aacagaatag acccaagaaa    3480
tctgtttga                                                             3489
```

```
SEQ ID NO: 35          moltype = AA  length = 409
FEATURE                Location/Qualifiers
source                 1..409
                       mol_type = protein
                       organism = Infectious Bronchitis Virus
SEQUENCE: 35
MASGKATGKT DAPAPVIKLG GPKPPKVGSS GNVSWFQAIK AKKLNSPPPK FEGSGVPDNE   60
NLKPSQQHGY WRRQARFKPG KGGRKPVPDA WYFYYTGTGP AANLNWGDSQ DGIVWVAGKG   120
ADTKFRSNQG TRDSDKFDQY PLRFSDGGPD GNFRWDFIPL NRGRSGRSTA ASSAASSRAP   180
SREVSRGRRS GSEDDLIARA ARIIQDQQKK GSRITKAKAD TIPPNYKVDQ               240
VFGPRTKGKE GNFGDDKMNE EGIKDGRVTA MLNLVPSSHA CLFGSRVTPR LQPDGLHLKF   300
EFTTVVPRDD PQFDNYVKIC DQCVDGVGTR PTDDEPRPKS RSSSRPATRG NSPAPRQQRP   360
KKEKKPKKQD DEVDKALTSD EERNNAQLEF DDEPKVINWG DSALGENEL               409
```

```
SEQ ID NO: 36          moltype = DNA  length = 1230
FEATURE                Location/Qualifiers
source                 1..1230
                       mol_type = other DNA
                       organism = Infectious Bronchitis Virus
SEQUENCE: 36
atggcgtcgg gtaaagctac agggaagact gatgctccag ctcccgtaat aaagttagga   60
gggccaaagc caccaaaagt tggatccagt ggaaatgtta gctggttcca ggcaataaaa   120
gccaagaagc tgaattctcc accccccaag tttgaaggtt ccggggtccc tgataacgag   180
aaccttaaac ccagccagca gcatggctac tggcgcaggc aggcccgatt caagcctgga   240
aaaggtggaa ggaagcccgt cccagatgcc tggtacttct actacaccgg gactggcccc   300
gcggccaact gaactggggg agactcccaa gatggcattg tgtgggtggc aggcaaagga   360
gctgcacca agttcagaag caaccagggg accagggaca gtgacaaatt tgatcaatat   420
cctctgcgct tcagtgatgg gggtcctgac ggcaatttc gctgggactt catacctctc   480
aatagaggac gtagtggtag atctacagca gcatcttcag ctgcctcttc acgggcgccg   540
agtagagaag tttcacgggg cagacgtagc ggctctgaag atgacctcat tgcacgggct   600
gcaaggatca tccaggacca acagaagaaa ggcagccgca ttacaaaggc caaagcagat   660
gaaatggctc acagacgcta ctgcaagagg acgatccccc caaattataa agtagaccag   720
gtgtttggac ctagaacaaa agggaaagaa ggaaacttcg gtgatgataa aatgaatgaa   780
gagggcatta agatggacg tgttactgcc atgctaaatc ttgttccttc ctcccatgcc   840
tgcctctttg gtagcagagt cacacctcga ctgcagcccg acgggctgca cctgaagttt   900
gagttcacca ctgtggtgcc acggggtgac ccgcagttta caactatgt gaagatctgt   960
gatcaatgtg tggatggggt aggcactaga ccaacagacg atgaacctcg acctaaatca   1020
cggtctagtt cccggccagc cacccgcggc aactccccag caccgcggca gcaaaggccc   1080
aaaaaggaga agaaaccaaa gaagcaggat gatgaggtgg acaaggcatt gacgtcagat   1140
gaggagagga caatgctca ctggagtttt gatgacgagc ccaaagtcat caactggggg   1200
gacagcgctt tgggagaaaa tgagctgtga                                     1230
```

```
SEQ ID NO: 37          moltype = AA  length = 409
FEATURE                Location/Qualifiers
source                 1..409
                       mol_type = protein
                       organism = Infectious Bronchitis Virus
SEQUENCE: 37
MASGKATGKT DAPAPVIKLG GPKPPKVGSS GNASWFQAIK AKKLNSHPPK FEGSGVPDNE   60
NLKTSQQHGY WRRQARFKPV KGGRKPVPDA WYFYYTGTGP AADLNWGDSQ DGIVWVAAKG   120
ADVKSRSHQG TRDPDKFDQY PLRFSDGGPD GNFRWDFIPL NRGRSGRSTA ASSAASSRAP   180
```

-continued

```
SRDGSRGRRS GSEDDLIARA AKIIQDQQKK GSRITKVKAD EMAHRRYCKR TIPPGYKVDQ    240
VFGPRTKGKE GNFGDDKMNE EGIKDGRVTA MLNLVPSSHA CLFGSRVTPK LQPDGLHLKF    300
EFTTVVPRDD PQFDNYVKIC DQCVDGVGTR PKDDEPRPKS RSSSRPATRT SSPAPRQQRP    360
KKEKKPKKQD DEVDKALTSN EERNNAQLEF DEEPKVINWG DAALGENEL                409

SEQ ID NO: 38          moltype = DNA   length = 1230
FEATURE                Location/Qualifiers
source                 1..1230
                       mol_type = other DNA
                       organism = Infectious Bronchitis Virus
SEQUENCE: 38
atggccagtg ggaaggcgac aggtaaaact gacgcgccag ctccagtcat caaacttggt     60
ggaccgaagc ctccaaaggt gggctccagt ggaaatgctt cttggttcca ggccattaag    120
gcaaaaaaac tgaacagtca tccacctaaa tttgagggt ctggcgtccc cgacaatgaa     180
aatctcaaaa cgtctcagca acatggttac tggagaagac aggcacgctt caagcctgtc    240
aaaggcggta gaaagccagt tcctgatgct tggtacttct attatactgg caccggacca    300
gcagctgatt tgaactgggg ggatagccag gatggcattg tgtgggtggc agccaaagga    360
gccgacgtaa aatcccggag ccaccagggc accagagatc tgacaagtt tgaccagtat    420
cctctgcgtt tcagtgacgg gggtcctgac ggaaacttcc gctgggactt catccccctc    480
aacaggggac gctcaggacg ctcaacggct gccagtctg cagcgtccag ccgagcaccc     540
agccgcgacg gctcccgggg gaggagaagc ggttcggaag acgatctaat tgcaagagca    600
gccaagatca ttcaggacca acagaagaaa ggttctcgga tcaccaaggt taaagcagat    660
gagatggcac accggcggta ctgcaagagg actattcccc caggctataa agttgatcag    720
gtcttcgggc ccagaaccaa agggaaagaa ggcaattttg gagacgacaa gatgaatgag    780
gagggaataa aggatgggag agtaactgcc atgctgaatc tggtgccttc tagccatgct    840
tgcctcttcg gcagtcgagt tacacccaag cttcagccag atgggctgca cctgaagttt    900
gaatttacaa cagtggtgcc gagggatgac cctcagtttg ataactacgt caagatatgt    960
gaccagtgtg tggatggcgt gggaacacgg cctaaagatg acgagcctag gcccaaatcg    1020
cgaagcagtt cacgtcccgc tactagaaca tcatccccag cgccgcgtca gcaaaggcca    1080
aaaaaggaga agaagcccaa gaagcaagat gatgaagtgg acaaagctct tacctcaaat    1140
gaagagcgca acaacgctca attggagttt gatgaagaac caaagttat caattgggga     1200
gatgccgctt aggagagaa cgagctgtga                                      1230

SEQ ID NO: 39          moltype = AA    length = 1173
FEATURE                Location/Qualifiers
source                 1..1173
                       mol_type = protein
                       organism = Infectious Bronchitis Virus
SEQUENCE: 39
MLVTPLLLVT LLCALCSAVL YDSSSYVYYY QSAFRPPNGW HLQGGAYAVV NISSEFNNAG     60
SSSSGCTVGII HGGRVVNASS IAMTAPSSGM AWSSSQFCTA HCNFSDTTVF VTHCYKHGGC    120
PITGMLQQNL IRVSAMKNGQ LFYNLTVSVA KYPTFRSFQC VNNLTSVYLN GDLVYTSNET    180
IDVTSAGVYF KAGGPITYKV MREVKALAYF VNGTAQDVIL CDGSPRGLLA CQYNTGNFSD    240
GFYPFTNSSL VKQKFIVYRE NSVNTTCTLH NFIFHNETGA NPNPSGVQNI QTYQTKTAQS    300
GYYNFNFSFL SSFVYKESNF MYGSYHPSCN FRLETINNGL WFNSLSVSIA YGPLQGGCKQ    360
SVFKGRATCC YAYSYGGPSL CKGVYSGELD HNFECGLLVY VTKSGGSRIQ TATEPPVITQ    420
NNYNNITLNT CVDYNIYGRT GQGFITNVTD SAVSYNYLAD AGLAILDTSG SIDIFVVQGE    480
YGLNYYKVNP CEDVNQQFVV SGGKLVGILT SRNETGSQLL ENQFYIKITN GTGGGVPSIT    540
ENVANCPYVS YGKFCIKPDG SIATIVPKQL EQFVAPLFNV TENVLIPNSF NLTVTDEYIQ    600
TRMDKVQINC LQYVCGSSLD CRKLFQQYGP VCDNILSVVN SVGQKEDMEL LNFYSSTKPA    660
GFNTPVLSNV STGEFNISLL LTTPSSRRKR SLIEDLLFTS VESVGLPTND AYKNCTAGPL    720
GFFKDLACAR EYNGLLVLPP IITAEMQALY TSSLVASMAF GGITAAGAIP FATQLQARIN    780
HLGITQSLLL KNQEKIAASF NKAIGHMQEG FRSTSLALQQ IQDVVSKQSA ILTETMASLN    840
KNFGAISSVI QEIYQQFDAI QANAQVDRLI TGRLSSLSVL ASAKQAEYIR VSQQRELATQ    900
KINECVKSQS IRYSFCGNGR HVLTIPQNAP NGIVFIHFSY TPDSFVNVTA IVGFCVKPAN    960
ASQYAIVPAN GRGIFIQVNG SYYITARDMY MPRAITAGDV VTLTSCQANY VSVNKTVITT    1020
FVDNDDFDFN DELSKWWNDT KHELPDFDKF NYTVPILDID SEIDRIQGVI QGLNDSLIDL    1080
EKLSILKTYI KWPGSGYIPE APRDGQAYVR KDGEWVLLST FLGRSLEVLF QGPGHHHHHH    1140
HHSAWSHPQF EKGGGGSGGGG SGGSAWSHPQ FEK                                1173

SEQ ID NO: 40          moltype = AA    length = 1180
FEATURE                Location/Qualifiers
source                 1..1180
                       mol_type = protein
                       organism = Infectious Bronchitis Virus
SEQUENCE: 40
MLVKSLFLVT ILFALCSANL YDNESFVYYY QSAFRPGHGW HLYGGAYAVV NVSSENNNAG     60
TAPSCTAGAI GYSKNLSAAS VAMTAPLSGM SWSANSFCTA HCNFTSYIVF VTHCYKSGSN    120
SCPLTGLIPS GYIRIAAMKH GSAMPGHLFY NLTVSVTKYP KFRSLQCVNN YTSVYLNGDL    180
VFTSNYTEDV VAAGVHFKSG GPITYKVMRE VKALAYFVNG TAHDVILCDD TPRGLLACQY    240
NTGNFSDGFY PFTNTSIVKD KFIVYRESSV NTTLTLTNFT FSNESGAPPN TGGVDSFILY    300
QTQTAQSGYY NFNFSFLSSF VYRESYYMYG SYHPRCSFRP ETLNNGLWFN SLSVSLTYGP    360
IQGGCKQSVF NGKATCCYAY SYGGPRACKG VYRGELTQHF ECGLLVYVTK SDGSRIQTAT    420
QPPVLTQNFY NNINLGKCVD YNIYGRIGQG LITNVTDLAV SYNYLSDAGL AILDTSGAID    480
IFVVQGEYGP NYYKVNPCED VNQQFVVSGG KLVGILTSRN ETGSQLLENQ FYIKITNGTG    540
GGVPSVTENV TNCPYVSYGK FCIKPDGSIS VIVPKELDQF VAPLLNVTEY VLIPNSFNLT    600
VTDEYIQTRM DKIQINCLQY VCGNSLACRK LFQQYGPVCD NILSVVNSVG QKEDMELLNF    660
YSSTKPARFN TPVFSNLSTG EFNISLLLTP PSSPRRRSFI EDLLFTSVES VGLPTDDAYK    720
MRTAGPLGFL KDLACAREYN GLLVLPPIIT AEMQTLYTSS LVASMAFGGI TAAGAIPFAT    780
```

```
QLQARINHLG ITQSLLLKNQ EKIAASFNKA IGHMQEGFRS TSLALQQIQD VVNKQSAILT   840
ETMLALNKNF GAISSVIQDI YQQLDSIQAD AQVDRLITGR LSSLSVLASA KQSEYIRVSQ   900
QRELATQKIN ECVKSQSIRY SFCGNGRHVL TIPQNAPNGI VFIHFTYTPE SFINVTAVVG   960
FCVSPANASQ YAIVPANGRG IFIQVNGSYY ITARDMYMPR DITAGDIVTL TSCQANYVSV  1020
NKTVITTFVD NDDFDFDDEL SKWWNETKHE LPDFDKFNYT VPILDIDSEI DRIQGVIQGL  1080
NDSLIDLETL SILKTYIKWP GSGYIPEAPR DGQAYVRKDG EWVLLSTFLG RSLEVLFQGP  1140
GHHHHHHHHS AWSHPQFEKG GGSGGGGSGG SAWSHPQFEK                       1180

SEQ ID NO: 41           moltype = AA  length = 1183
FEATURE                 Location/Qualifiers
source                  1..1183
                        mol_type = protein
                        organism = Infectious Bronchitis Virus
SEQUENCE: 41
MLVKSPFIVT LLCALCSASL YDNGSYVYYY QSAFRPSIGW HLHGGAYAVV NVTQEYNNAG   60
SASECTAGAI VWSKNFSAAS VAMTAPHSGM SWSVKQFCTA HCNFTNFVVF VTHCFKDGLN  120
TCPLTGRIDQ GYIRIAAMKN TGTGPRDLFY NFTVSVTKYP SFKSLQCVNN QTSVYLNGDL  180
VFTSNETVDV SGAGVHFKAG GPITYKVMRE VKALAYFVNG TAQDVILCDS SPRGLLACQY  240
NTGNFSDGFY PFTNSSVVKE KFIVYSENSV NTTLVLHNFT FYNESDAPPN SQQSSAGVGG  300
LTTYQTQTAQ SGYYNFNFSF LSSFVYKESN FMYGSYHPQC NFRPENINNG LWFNSLSVSI  360
TYGPLQGGCK QSVFSHRATC CYAYSYNGPH ICKGVYSGQL HNNFECGLLV YITKTDGSRI  420
QTATTPPVRT QHFYNNITLH KCVEYNIYGR VGQGFITNVT DSVAGYNYLQ DGGLAILDTS  480
GAIDIFAVQG GYGLNPYKVN PCEDVNQQFV VSGGNLVGIL TSRNETDSQP LENQFFVKLI  540
NGTGGGVPSI SENVTSCSFV SYGKFCIKPD GSISTIVPKE MEQFVAPLLN VTEHVLIPDS  600
FNLTVTDEYI QTRMDKVQIN CLQYVCGNSF ECRQLFQQYG PVCDNILSVV NSVGQKEDME  660
LLSFYSSTKP AGYNTPVFNI STGDFNISLL LPPSSAPSGR SFIEDLLFTS VESVGLPTDE  720
AYKKCTAGPL GFLKDLACAR EYNGLLVLPP IITAEMQTLY TSSLVASMAL GGITAAGAIP  780
FATQLQARIN HLGITQTVLL KNQEKIAASF NKAIGHMQEG FKSTSLALQQ IQDVVNKQSA  840
ILTETMASLN KNFGAISSVI QEIYQQLDAI QANAQVDRLI TGRLSSLSVL ASSKQAEYLR  900
VSQQRELATQ KINECVKSQS TRYSFCGNGR HVLTIPQNAP NGIVFIHFTY TPESFVNVTA  960
IVGFCINPAN ASQYAIVPAN GRGIFIQVNG TYYITARDMF MPRDITAGDV VTLTSCQANY 1020
VSVNKTVITT FVESDDFDFD DELSKWWNET KHEFPDFDQF NYTIPVLNIT YDIDKIEEVI 1080
KGLNDSLIDL ETLSILKTYI KWPGSGYIPE APRDGQAYVR KDGEWVLLST FLGRSLEVLF 1140
QGPGHHHHHH HHSAWSHPQF EKGGGSGGGG SGGSAWSHPQ FEK                 1183

SEQ ID NO: 42           moltype = AA  length = 1177
FEATURE                 Location/Qualifiers
source                  1..1177
                        mol_type = protein
                        organism = Infectious Bronchitis Virus
SEQUENCE: 42
MLVKSLFTVI PLFALCSATL YDSGSYVYYY QSAFRPPNGW QLHGGAYAVV NVSTETGSAN   60
RCTAGAISFS KNFSAASVAM TAPANGMTWS DAQFCTAHCN FTNIVVFVTH CFKNRPNYCS  120
LTGLIPQNYI RIAAMKSNGT GPSDLFYNLT VPVTKYPKFR SLQCVNNQTS VYLNGDLVFT  180
SNETVDISGA GVHFAAGGPI TYKVMREVKA LAYFVNGTAQ DVILCDGTPR GLLACQYNTG  240
NFSDGFYPFT NSSLVKERFI VYRENSVNTT LVLHNVTFFN ETSAPNGGDL NANFQIYQTV  300
TAQSGYYNFN FSFLSGFVYK ESDFMYGSYH PNCNFRPENI NNGLWFNSLS ISLAYGPLQG  360
GCKQSVFNRR ATCCYAYSYN GPHACKGVYR GQLTQLFECG LLVYITKSDG SRIQTATKAL  420
VVTTNFYNNI TLDRCVEYNI YGRVGQGFIT NVTDSTADYN YLADGGLAIL DTSGAIDIFV  480
VQGVYGLNFY KVNPCEDVNQ QFVVSGGKLV GILTSRNETD SQFLENQFYI KLTNETHGGG  540
VPVSENVTSC PYVSYGKFCI KPDGSISTIV PEELKQFVSP LLNVTEYVLI PDSFNLTVTD  600
EYIQTRMDKV QINCLQYVCG NSFECRNLFQ QYGPVCDNIL SVVNSVGQKE DMELLTFYSS  660
TKPAGYNTPV FNNISTGDFN ISLLLTPPST PSGRSFIEDL LFTSVESVGL PTDEAYKKCT  720
AGPLGFLKDL ACAREYNGLL VLPPIITAEM QTLYTSSLVA SMALGGITAA GAIPFATQLQ  780
ARINHLGITQ TILLKNQEKI AASFNKAIGH MQEGFKSTSL ALQQIQDVVN KQSAILTETM  840
ASLNKNFGAI SSVIQEIYQQ LDSIQANAQV DRIITGRLSS LSVLASSKQA EYLRVSQQRE  900
LATQKINECV KSQSTRYSFC GNGRHVLTIP QNAPNGIVPI HFTYTPESFV NVTAIVGFCV  960
NPANASQYAI VPANGRGIFI QVNGSYYITA RDMYMPRDIT AGDIVTLTSC QANYVSVNKT 1020
VITTLVDNDD FDFHDELSKW WNETKHELPD FDQFNYTIPV LNITYDIDKI EEVIKGLNDS 1080
LIDLETLSIL KTYIKWPGSG YIPEAPRDGQ AYVRKDGEWV LLSTFLGRSL EVLFQGPGSA 1140
WSHPQFEKGG GSGGGGSGGH HHHHHHSAW SHPQFEK                        1177

SEQ ID NO: 43           moltype = AA  length = 1180
FEATURE                 Location/Qualifiers
source                  1..1180
                        mol_type = protein
                        organism = Infectious Bronchitis Virus
SEQUENCE: 43
MSVLLPLLVT LLCALCSAVL YDINSYVYYY QSAFRPSNGW HLYGGAYAVV NVSNENNNAG   60
SASTCTAGAI GYSKNFSAAS IAMTAPPSGM AWSTAAFCTA HCNFTNIVVF VTHCYKSGSG  120
SCPLTGFIQS GYIRISAMKK ECSGPSCLFY NLTESVSKYP TFRSLQCVNN YTSVYLNGDL  180
VFTSNYTQDV VAAGVHFKSG GPITYKVMRE VKALAYFVNG TAQDVILCDD TPRGLLACQY  240
NTGNFSDGFY PFTNTSIVKD KFIVYRESSV NTTLTLTNFT FSNESGAPPN TGGVNSFILY  300
QTQTAQSGYY NFNFSFLSGF VYEESNYMYG SYHPLCSFRP ENINNGLWFN SLSVSITYGP  360
LQGGCKQSFF QGRATCCYAY SYNGPRACKG VYSGELTQSF ECGLLVYITK SDGSRIQTAT  420
KAPVVTTNFY NNITLDKCVE YNIYGRVGQG FITNVTDSAF GYNYLQDGGL AILDTSGAID  480
IFVVKGVYGL NYYKVNPCED VNQQFVVSGG TLVGVLTSRN ETGSQFLENQ FYIKLTNGTH  540
GGGVPVNENV TSCPYVSYGK FCIKPDGSTS VIVPKELEQF VTPLLNATEY VPIPDSFNLT  600
VTDEYIQTRM DKVQINCLQY VCGNSFECRN LFQQYGPVCD NILSIVNSVS QKEDMELLTF  660
```

-continued

```
YSSTKPFGFN TPILSNLSTG DFNISLLLTP PSSTTGRSFI EDLLFTSVES VGLPTDDAYK    720
KCTAGPLGFL KDLACAREYN GLLVLPPIIT AEMQTMYTSS LVASMALGGI TAAGAIPFAT    780
QLQARINHLG ITQAVLLKNQ EKIAASFNKA IGQMQEGFRS TSLALQQIQD VVNKQSAILT    840
ETMASLNKNF GAISSVIQDI YQQLDVIQAD AQVDRLITGR LSSLSVLASA KQSEHIIASQ    900
QRELATQKIN ECVKSQSTRY SFCGNGRHVL TIPQNAPNGI VFIHFTYTPE SFVNVTAIVG    960
FCVKPANASQ YAIVPANGRG IFIQFNGSYY ITARDMYMPR NITAGDIVTL TSCQSNYVSV   1020
NKTVITTFVD NDDFDFDDEL SKWWNDTKHE LPDFDEFNYT APILDIDSEI DRIQGVIQGL   1080
NDSLIDLETL SILKTYIKWP GSGYIPEAPR DGQAYVRKDG EWVLLSTFLG RSLEVLFQGP   1140
GHHHHHHHHS AWSHPQFEKG GGSGGGGSGG SAWSHPQFEK                        1180
```

SEQ ID NO: 44          moltype = AA   length = 1170
FEATURE                Location/Qualifiers
source                 1..1170
                       mol_type = protein
                       organism = Infectious Bronchitis Virus
SEQUENCE: 44

```
MLVTPLLLVT LLFALCSAAL YDNSSYVYYY QSAFRPPNGW HLHGGAYAVV NTSIESNNLR    60
ECIVGIIGGD RVVNASSIAM TAPQPGMDWS SRQFCTAHCN FSDITVFVTH CYKHNGCPIT   120
GSIPQHSIRV SAMKKGRLFY NLTVSVNKYP TFKSFQCVNN FTSVYLNGDL VYTSNETTDV   180
TSAGVYFNAG GPITYKVMRE VKALAYFVNG TAQDVILCDG SPRGLLSCQY NTGNFSDGFY   240
PFTNSSLVKQ KFIVYRENSI NTTLKLHNFT FHNETGANPN LSGVQNIQTY QTQTAQSGYY   300
NFNFSFLSGF VYKESNFMYG SYHPSCNFRP ETINNGLWFN SLSVSIAYGP LQGGCKQSVF   360
SGRATCCYAY SYGGPSLCKG VYLGELKSDF ECGLLVYVTK SDGSRIQTAT EPPVITQHNY   420
NNITLNTCVD YNIYGRTGQG FITNVTDSAV SYNYLADAGM AILDTSGSID IFVVQGEYGL   480
TYYKVNPCED VNQQFVVSGG KLVGILTSRN ETGSQLLENQ FYIKITNGTG GGVPSITANV   540
TNCPYVSYGK FCIKPDGSVS AIVPKELEQF VAPLLNVTEN VLIPNSFNLT VTDEYIQTRM   600
DKIQINCMQY VCGNSLDCRK LFQQYGPVCD NILSVVNSVG QKEDMELLNF YSSTKPSGFN   660
TPVFSNLSTG DFNISLLLTP PSSTTGRSFI EDLLFTSVES VGLPTDEAYK KCTAGPLGFL   720
KDLACAREYN GLLVLPPIIT AEMQTLYTSS LVASMAFGGI TAAGAIPFAT QLQARINHLG   780
ITQSLLQKNQ EKIAASFNKA IAVVQEGFRS TSLALQQVQD VVNKQSAILT ETMASLNKNF   840
GAISSVIQDI YQQLDAIQAN AQVDRLITGR LSSLSVLASA KQAEYIRVSQ QRELATQKIN   900
ECVKSQSIRY SFCGNGRHVL TIPQNAPNGI VFIHFTYTPE SFVNVTAIVG FCVKPANASQ   960
YAIVPANGRG IFIQVNGSYY ITARDMYMPR DITAGDIVTL TSCQANYVSV NKTVITTFVD   1020
NDDFDFDDEL SKWWNDTKHE LPDFDEFNYT VPILDIGSEI DRIQGVIQGL NDSLIDLETL   1080
SILKTYIKWP GSGYIPEAPR DGQAYVRKDG EWVLLSTFLG RSLEVLFQGP GHHHHHHHHS   1140
AWSHPQFEKG GGSGGGGSGG SAWSHPQFEK                                   1170
```

SEQ ID NO: 45          moltype = AA   length = 1170
FEATURE                Location/Qualifiers
source                 1..1170
                       mol_type = protein
                       organism = Infectious Bronchitis Virus
SEQUENCE: 45

```
MLGKSLFIVT LLLALCEGGL VGVNYTYYYQ SRYRPPNGWH MQGGAYKVVN KTTISYTSQE    60
CTIGVIRGGV TINQSAIAFT SATGRVGVKK GVCTVYCNYT SFYVFVTHCG GTGHNCIVNT   120
KKLGVLVFGV KNYNDQFIYN ITLNAAGPYA NFKAWQCLSN YTSVFLNGNL LYTSNYTEDV   180
KAAGVYAKQV NGLERRVMRD TPVMAYFVNG TVQDVILCDD SPKGRLACQY NTGNFSDGLY   240
PVYEEPVASN FTFVPLHTSS TSYGVLHNFT FNNVTGVAPN QEHIARFNIS TISEGYVNFK   300
FNFLNSFTYV ESDFDRGSYY GKPGSRCNFG LESINRGLSF NSLTVSIGYG PISGGCKQSV   360
WKNEATCCFA YKYNGGSRNC KGLYTFDRDV NYECVLLVFI SKPDGSRIRT ATSPPVYSNN   420
NVNINLGLCV DYNVYGITGR GLITNITESV HPGYLDHGGL VLLDATGSID TFVLHSDKLT   480
SYYKVNPCSD INEQYVVSGG NLVGKLTSNN QTVAQQLGDM FYVKFSTGGG GGVPATSENV   540
TSCPYVTYGK FCIKPDGDIS NIVPEEVKDY TSLLLNRTDY VLIPNSFNLT VTDEFIQTQF   600
QKIQINCIQY VCGSSIQCKQ LFQQYGSVCG NILSIVNGIA LQDNAEMLHF YSSTKPRGFD   660
TNSFVNFTAG EFNISLVLPK NGQPTGRCLI EDLLFDKVES LGLPGDSAYQ KCTSGPLGFV   720
KDLVCAQNYN GLLVLPPIIT AEMQTLYTSS LVVSMAFGGI TAARAIPFAT QIQARINHLG   780
ITQTVLQKNQ EKIAASFNKA MKHMQDGFSA TSLALQQVQD VVNEQGAILQ QTMHSLNKNF   840
GAISHVIQDI YKQLDALEAN AQVDRIITGR LSSLSVLASA KQLEYTKVSQ QRELAKEKIN   900
ECVKSQSNRH GFCGEGMHIM SIPQNAPNGI VFLHFTYTPE TYANVTAVVG FCVKPGNGTE   960
YGLVPVVGRG IFIEVNGTYY ITGRDMYSPR AITAGDVVKL TPCQANYQSI NRTVITTFVD   1020
EDDFDFDHEL SKWWNETSRD FPNLDEFNYT IPVLNISNEI DKIQEVIQGL NDSIIDLETL   1080
SILKTYIKWP GSGYIPEAPR DGQAYVRKDG EWVLLSTFLG RSLEVLFQGP GHHHHHHHHS   1140
AWSHPQFEKG GGSGGGGSGG SAWSHPQFEK                                   1170
```

SEQ ID NO: 46          moltype = DNA   length = 22
FEATURE                Location/Qualifiers
source                 1..22
                       mol_type = other DNA
                       organism = synthetic construct
SEQUENCE: 46
atgctcaacc tagtccctag ca                                            22

-continued

```
SEQ ID NO: 47          moltype = DNA   length = 21
FEATURE                Location/Qualifiers
source                 1..21
                       mol_type = other DNA
                       organism = synthetic construct
SEQUENCE: 47
tcaaactgcg gatcatcacg t                                        21
```